US008541388B2

(12) United States Patent
Monia et al.

(10) Patent No.: US 8,541,388 B2
(45) Date of Patent: Sep. 24, 2013

(54) METHODS FOR MODULATING EXPRESSION OF RBP4

(75) Inventors: Brett P. Monia, Encinitas, CA (US); Xing-Xian Yu, San Diego, CA (US); Sanjay Bhanot, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 129 days.

(21) Appl. No.: 12/993,250

(22) PCT Filed: May 21, 2009

(86) PCT No.: PCT/US2009/044919
§ 371 (c)(1),
(2), (4) Date: Feb. 2, 2011

(87) PCT Pub. No.: WO2009/143390
PCT Pub. Date: Nov. 26, 2009

(65) Prior Publication Data
US 2011/0123521 A1 May 26, 2011

Related U.S. Application Data

(60) Provisional application No. 61/128,628, filed on May 22, 2008.

(51) Int. Cl.
*C12N 15/11* (2006.01)
*A61K 48/00* (2006.01)
*C07H 21/02* (2006.01)
*C07H 21/04* (2006.01)

(52) U.S. Cl.
USPC ........................................ 514/44 A; 536/24.5

(58) Field of Classification Search
USPC .............. 514/44; 536/23.1, 24.3, 24.33, 24.5
See application file for complete search history.

(56) References Cited

U.S. PATENT DOCUMENTS

| | | | |
|---|---|---|---|
| 5,770,713 A | 6/1998 | Imbach et al. | |
| 5,801,154 A | 9/1998 | Baracchini et al. | |
| 6,287,860 B1 | 9/2001 | Monia et al. | |
| 6,509,559 B1 | 1/2003 | Ulrich et al. | |
| 6,582,908 B2 | 6/2003 | Fodor et al. | |
| 2001/0053519 A1 | 12/2001 | Fodor et al. | |
| 2003/0228597 A1 | 12/2003 | Cowsert et al. | |
| 2004/0005292 A1* | 1/2004 | Bennett et al. | 424/93.2 |
| 2004/0053367 A1 | 3/2004 | Griffin et al. | |
| 2005/0208535 A1 | 9/2005 | Kahn et al. | |
| 2007/0031844 A1 | 2/2007 | Khvorova et al. | |

FOREIGN PATENT DOCUMENTS

| | | |
|---|---|---|
| EP | 2202223 | 6/2010 |
| WO | WO 93/24510 | 12/1993 |
| WO | WO 94/26764 | 11/1994 |
| WO | WO 99/14226 | 3/1999 |
| WO | WO 02/059621 | 8/2002 |
| WO | WO 03/004602 | 1/2003 |
| WO | WO 2005/059564 | 6/2005 |
| WO | WO 2005/113016 | 12/2005 |
| WO | WO/2007/143315 | 12/2007 |

OTHER PUBLICATIONS

Colantuoni et al. (Nucleic Acids Research, 1983 vol. 11, No. 22, pp. 7769-7776).*
Aeberli et al., "Serum Retinol-Binding Protein 4 Concentration and Its Ratio to Serum Retinol Are Associated with Obesity and Metabolic Syndrome Components in Children" J. Clin. Endocrinol. Metab. (2007) 92(11):4359-4365.
Bajzova et al., "Retinol-Binding Protein 4 Expression in Visceral and Subcutaneous Fat in Human Obesity" Physiol. Res. (2008) 57:927-934.
Balagopal et al., "Reduction of Elevated Serum Retinol Binding Protein in Obese Children by Lifestyle Intervention: Association with Subclinical Inflammation" J. Clin. Endocrinol. Metab. (2007) 92(5):1971-1974.
Barber et al., "Serum levels of retinol-binding protein 4 and adiponectin in women with polycystic overay syndrome: associations with visceral fat but no evidence for fat mass-independent effects on pathogenesis in this condition" J. Clin. Endocrinol. Metab. (2008) 93(7):2859-2865.
Berge et al., "Pharmaceutical Salts" J. Pharma Sci. (1977) 66:1-19.
Berndt et al., "Fatty acid synthase gene expression in human adipose tissue: association with obesity and type 2 diabetes" Diabetologia (2007) 50:1472-1480.
Branch et al., "A good antisense molecule is hard to find," TIBS (1998) 23:45-50.
Broch et al., "Circulating Retinol-Binding Protein-4, Insulin Sensitivity, Insulin Secretion, and Insulin Disposition Index in Obese and Nonobese Subjects" Diabetes Care (2007) 30(7):1802-1806.
Browning et al., "Molecular mediators of hepatic steatosis and liver injury" Clin. Invest. (2004) 114:147-152.
Bunn e tal., "The Glycosylation of Hemoglobin: Relevance to Diabetes Mellitus" Science (1978) 200:21-27.
Cabre et al., "Retinol-binding protein 4 as a plasma biomarker of renal dysfunction and cardiovascular disease in type 2 diabetes" J. Intern Med. (2007) 262(4):496-503.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Cho et al., "Plasma Retinol-Binding Protein-4 Concentrations are Elevated in Human Subjects with Impaired Glucose Tolerance and Type 2 Diabetes" Diabetes Care (2006) 29(11):2457-2461.

(Continued)

*Primary Examiner* — Terra Cotta Gibbs
(74) *Attorney, Agent, or Firm* — Isis Pharmaceuticals, Inc. Patent Dept.

(57) ABSTRACT

Methods are provided for modulating RBP4 by administering a RBP4-specific modulator. Also provided are methods for treating cardiovascular and metabolic disorders in a subject or delaying or preventing risk factors thereof through the modulation of RBP4. The present invention is also directed to methods of decreasing lipid levels in a subject or for preventing or delaying the onset of a rise in lipid levels in a subject, comprising administering to said subject a RBP4-specific inhibitor.

35 Claims, No Drawings

(56) References Cited

OTHER PUBLICATIONS

Choi et al., "Suppression of Diacylglycerol Acyltransferase-2 (DGAT2), but Not DGAT1, with Antisense Oligonucleotides Reverses Diet-induced Hepatic Steatosis and Insulin Resistance" J. Biol. Chem. (2007) 282:22678-22688.
Choi et al., "Retinol binding protein-4 elevation is associated with serum thyroid-stimulating hormone level independently of obesity in elderly subjects with normal glucose tolerance" J. Clin. Endocrinol. Metab. (2008) 93(6):2313-2318.
Choi et al., "High plasma retinol binding protein-4 and low plasma adiponectin concentrations are associated with severity of glucose intolerance in women with previous gestational diabetes mellitus" J. Clin. Endocrinol. Metab. (2008) 93(8):3142-3148.
Craig et al., "Retinol binding protein 4 as a candidate gene for type 2 diabetes and prediabetic intermediate traits" Molecular Genetics and Metabolism (2007) 90:338-344.
Crooke et al., "Basic Principles of Antisense Therapeutics" Antisense Research and Application (1998) Chapter 1:1-50.
Elbashir et al., "Duplexes of 21-nucleotide RNAs mediate RNA interference in cultured mammalian cells" Nature (2001) 411:494-498.
Executive Summary of the Third Report of the National Cholesterol Education Program (NCEP) Expert Panel on Detection, Evaluation, and Treatment of High Blood Cholesterol in Adults (Adult Treatment Panel III), JAMA (2001) 285(19):2486-2497.
Fernandez-Real et al., "Circulating retinol-binding protein-4 concentration might reflect insulin resistance-associated iron overload" Diabetes (2008) 57(7):1918-1925.
Gallou-Kabani et al., "C57BL/6J and A/J Mice Fed a High-Fat Diet Delineate Components of Metabolic Syndrome" Obesity (2007) 15(8):1996-2005.
Gautschi et al., "Activity of a Novel bcl-2/bcl-xL-Bispecific Antisense Oligonucleotide Against Tumors of Diverse Histologic Origins" J. Natl. Cancer Inst. (2001) 93:463-471.
Gavi et al., "Retinol-Binding Protein 4 Is Associated with Insulin Resistance and Body Fat Distribution in Nonobese Subjects without Type 2 Diabetes" J. Clin. Endocrinol. Metab. (2007) 92(5):1886-1890.
Gavi et al., "Influence of Age on the Association of Retinol-binding Protein 4 With Metabolic Syndrome" Obesity (2008) 16(4):893-895.
Gomez-Ambrosi et al., "Serum retinol-binding protein 4 is not increased in obesity or obesity-associated type 2 diabetes mellitus, but is reduced after relevant reductions in body fat following gastric bypass" Clin. Endocrinol. (2008) 69(2):208-215.
Graham et al., "Retinol-Binding Protein-4 and Insulin Resistance in Lean, Obese, and Diabetic Subjects" N. Engl. J. Med. (2006) 354(24):2552-2563.
Graham et al., "Shortcomings in methodology complicate measurements of serum retinol binding protein (RBP4) in insulin-resistant human subjects" Diabetologia (2007) 50:814-823.
Grundy et al., "Implications of Recent Clinical Trials for the National Cholesterol Education Program Adult Treatment Panel III Guidelines" Circulation (2004) 110:227-239.
Gutierrez-Juarez et al., "5-Heteroaryl-2'-deoxyuridine Analogs. Synthesis and Incorporation into High-Affinity Oligonucleotides" J. Clin. Invest. (2006) 116:1686-1695.
Hahn et al., "Retinol-binding protein 4 levels are elevated in polycystic ovary syndrome women with obesity and impaired glucose metabolism" European Journal of Endocrinology (2007) 157:201-207.
Hammarstedt et al., "High circulating levels of RBP4 and mRNA levels of aP2, PGC-1alpha and UCP-2 predict improvement in insulin selectivity following pioglitazone treatment of drug-naïve type 2 diabetic subjects" J. Intern. Med. (2008) 263(4):440-449.
Haseloff et al., "Simple RNA enzymes with new and highly specific endoribonuclease activities" Nature (1988) 334:585-591.
Herzig et al., "CREB controls hepatic lipid metabolism through nuclear hormone receptor PPAR-gamma" Nature (2003) 426:190-193.
Heymsfield, "Effects of Weight Loss With Orlistat on Glucose Tolerance and Progression to Type 2 Diabetes in Obese Adults" Archives of Internal Medicine (2000) 160:1321-1326.
Hylemon et al., "Hormonal Regulation of Cholesterol 7alpha-Hydroxylase mRNA Levels and Transcriptional Activity in Primary Rat Hepatocyte Cultures" J. Biol. Chem. (1992) 267(24):16866-16871.
Isken et al., "RBP4 Disrupts Vitamin A Uptake Homeostasis in a STRA6-Deficient Animal Model for Matthew-Wood Syndrome" Cell Metabolism (2008) 7:258-268.
Jones et al., "RNA Quantitation by Fluorescence-Based Solution Assay: RiboGreen Reagent Characterization" Analytical Biochemistry (1998) 265:368-374.
Kahn et al., "The Metabolic Syndrome: Time for a Critical Appraisal: Joint statement from the American Diabetes Association and the European Association for the Study of Diabetes" Diabetes Care (2005) 28(9:):2289-2304.
Kanaka-Gantenbein et al., "Retinol-binding protein 4 and lipocalin-2 in childhood and adolescent obesity: when children are not just "small adults"" Clin. Chem. (2008) 54(7):1176-1182.
Kempin et al., "Targeted disruption in *Arabidopsis*" Nature (2007) 389:802-803.
Kloting et al., "Serum retinol-binding protein is more highly expressed in visceral than in subcutaneous adipose tissue and is a marker of intra-abdominal fat mass" Cell. Metab. (2007) 6(1):79-87.
Kovacs et al., "Effects of Genetic Variation in the Human Retinol Binding Protein-4 Gene (RBP4) on Insulin Resistance and Fat Depot-Specific mRNA Expression" Diabetes (2007) 56:3095-3100.
Kowalska et al., "Serum retinol binding protein 4 is related to insulin resistance and nonoxidative glucose metabolism in lean and obese women with normal glucose tolerance" J. Clin. Endocrinol. Metab. (2008) 93(7):2786-2789.
Krzyzanowska et al., "Serum concentrations of retinol-binding protein 4 in women with and without gestational diabetes" Diabetologia (2008) 51(7):1115-1122.
Lee et al., "Association of serum retinol binding protein 4 and insulin resistance in apparently healthy adolescents" Metabolism Clinical and Experimental (2007) 56:327-331.
Lee et al., "ssDNA aptamer-based surface plasmon resonance biosensor for the detection of retinol binding protein 4 for the early diagnosis of type 2 diabetes" Anal. Chem. (2008) 80(8):2867-2873.
Lee et al., "Abdominal Visceral Fat Reduction is Associated with Favorable Changes of Serum Retinol Binding Protein-4 in Nondiabetic Subjects" Endocrine Journal (2008) 55(5):811-818.
Lee et al., "Visceral Adiposity Is Associated with Serum Retinol Binding Protein-4 Levels in Healthy Women" Obesity (2007) 15(9):2225-2232.
Lim et al., "Insulin-sensitizing effects of exercise on adiponectin and retinol-binding protein-4 concentrations in young and middle-aged women" J. Clin. Endocrinol. Metab. (2008) 93(6):2263-2268.
Maher et al., "Comparative hybrid arrest by tandem antisense oligodeoxyribonucleotides or oligodeoxy-ribonucleoside methylphosphonates in a cell-free system" Nuc. Acid. Res. (1988) 16(8):3341-3358.
Mercader et al., "Retinol-binding protein 4 and nicotinamide phosphoribosyltransferase/visfatin in rat obesity models" Horm. Metab. Res. (2008) 40(7):467-472.
Mody et al., "Decreased clearance of serum retinol-binding protein and elevated levels of transthyretin in unsulin-resistant ob/ob mice" Am. J. Physiol. Endocrinol. Metab. (2008) 294(4):E785-E793.
Mohlig et al., "Retinol-binding protein 4 is associated with insulin resistance, but appears unsuited for metabolic screening in women with polycystic ovary syndrome" Eur. J. Endocrinol. (2008) 158(4):517-523.
Munkhtulga et al., "Identification of a regulatory SNP in the retinol binding protein 4 gene associated with type 2 diabetes in Mongolia" Hum. Genet. (2007) 120(6):879-888.
Nawano et al., "Hyperglycemia contributes insulin resistance in hepatic and adipose tissue but not skeletal muscle of ZDF rats" Am. J. Physiol. Endocrinol. Metab. (2000) 278:E535-543.
Naylor e tal., "The structure of human retinol-binding protein (RBP) with its carrier protein transthyretin reveals an interaction with the carboxy terminus of RBP." Biochemistry (1999) 38:2647-2653.

Neschen et al., "Prevention of hepatic steatosis and hepatic insulin resistance in mitochondrial acyl-CoA:glycerol-sn-3-phosphate acyltransferase 1 knockout mice" Cell Metab. (2005) 2:55-65.

New England Biolabs 1998/99 Catalog (cover page and pp. 121 and 284).

Ost et al., "Retinol-binding protein-4 attenuates insulin-induced phosphorylation of IRS1 and ERK1/2 in primary human adipocytes" The FASEB Journal (2007) 21:3696-3704.

Petersen et al., "Reversal of Nonalcoholic Hepatic Steatosis, Hepatic Insulin Resistance, and Hyperglycemia by Moderate Weight Reduction in Patients With Type 2 Diabetes " Diabetes (2005) 54:603-608.

Petersen et al., "Leptin reverses insulin resistance and hepatic steatosis in patients with severe lipodystrophy" J. Clin. Invest. (2002) 109(10):1345-1350.

Pittner et al., "Effects of PYY[3-36] in rodent models of diabetes and obesity" Int. J. Obes. Relat. Metabl Disord. (2004) 28:963-971.

Qi et al., "Elevated Retinol-Binding Protein 4 Levels are Associated with Metabolic Syndrome in Chinese People" J. Clin. Endocrinol. Metab. (2007) 92(12):4827-4834.

Raila et al., "Microalbuminuria is a major determinant of elevated plasma retinol-binding protein 4 in type 2 diabetic patients" Kidney International (2007) 72: 505-511.

Reinehr et al., "Retinol-binding protein 4 and its relation to insulin resistance in obese children before and after weight loss" J. Clin. Endocrinol. Metab. (2008) 93(6):2287-2293.

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Savage et al., "Reversal of diet-induced hepatic steatosis and hepatic insulin resistance by antisense oligonucleotide inhibitors of acetyl-CoA carboxylases 1 and 2" J. Clin. Invest. (2006) 116(3):817-824.

Schiffelers et al., "Cancer siRNA therapy by tumor selective delivery with ligand-targeted sterically stabilized nanoparticle" Nucleic Acids Research (2004) 32(19):e149.

Seo et al., "Serum retinol-binding protein 4 levels are elevated in non-alcoholic fatty liver disease" Clinical Endocrinology (2008) 68:555-560.

Shea et al., "Serum retinol-binding protein 4 concentrations in response to short-term overfeeding in normal-weight, overweight, and obese men" Am. J. Clin. Nutr. (2007) 86:1310-1315.

Shimamura et al., "Leptin and insulin down-regulate angiopoietin-like protein 3, a plasma triglyceride-increasing factor" Biochem. Biophys. Res. Commun. (2004) 322:1080-1085.

Sindelka et al., "Association of Obesity, Diabetes, Serum Lipids and Blood Pressure Regulates Insulin Action" Physiol. Res. (2002) 51:85-91.

Stefan et al., "High Circulating Retinol-Binding Protein 4 Is Associated With Elevated Liver Fat but Not With Total, Subcutaneous, Visceral, or Intramyocellular Fat in Humans" Diabetes Care (2007) 30(5):1173-1806.

Takebayashi et al., "Retinol Binding Protein-4 Levels and Clinical Features of Type 2 Diabetes Patients" J. Clin. Endocrinol. Metab. (2007) 92(7):2712-2719.

Tamori et al., "RBP4, an unexpected adipokine" Nature Medicine (2006) 12(1):30-31.

Tan et al., "Raised Serum, Adipocyte, and Adipose Tissue Retinol-Binding Protein 4 in Overweight Women with Polycystic Ovary Syndrome: Effects on Gonadal and Adrenal Steroids" J. Clin. Endocrinol. Metab. (2007) 92(7):2764-2772.

Ueland et al., "Retinol-binding protein-4 is not strongly associated with insulin sensitivity in normal pregnancies" Eur. J. Endocrinol. (2008) 159(1):49-54.

Van Hock et al., "An RBP4 promoter polymorphism increases risk of type 2 diabetes" Diabetologia (2008) 51:1423-1428.

Vitkova et al., "Plasma Levels and Adipose Tissue Messenger Ribonucleic Acid Expression of Retinol-Binding Protein 4 Are Reduced during Calorie Restriction in Obese Subjects but are Not Related to Diet-Induced Changes in Insulin Sensitivity" J. Clin. Endocrinol. Metab. (2007) 92(6):2330-2335.

Von Eynatten et al., "Retinol-binding protein-4 in experimental and clinical metabolic disease" Expert Rev Mol Diagn (2008) 8(3):289-299.

Von Eynatten et al., "Retinol-binding protein-4 is associated with components of the matbolic syndrome, but not with insulin resistance, in men with type 2 diabetes or coronary artery disease" Diabetologia (2007) 50:1930-1937.

Wolf, "Serum retinol-binding protein: a link between obesity, insulin resistance, and type 2 diabetes" Nutr. Rev. (2007) 65(5):251-256.

Woolf et al., "Specificity of antisense oligonucleotides in vivo" PNAS (1992) 89:7305-7309.

Yamamoto et al., "Overexpression of PACAP in Transgenic Mouse Pancreatic β-Cells Enhances Insulin Secretion and Ameliorates Streptozotocin-induced Diabetes " Diabetes (2003) 52:1155-1162.

Yang et al., "Serum retinol binding protein 4 contributes to insulin resistance in obesity and type 2 diabetes" Nature (2005) 436:356-361.

Yao-Borengasser et al., "Retinol Binding Protein 4 Expression in Humans: Relationship to Insulin Resistance, Inflammation, and Response to Pioglitazone" J. Clin. Endocrinol. Metab. (2007) 92(7):2590-2597.

Yki-Jarvinen et al., "Insulin inhibition of overnight glucose production and gluconeogenesis from lactate in NIDDM" Am. J. Physiol. (1989) 256:E732-739.

Wu et al., "Serum retinol binding protein 4 and nonalcoholic fatty liver disease in patients with type 2 diabetes mellitus" Diabetes Research and Clinical Practice (2008) 79:185-190.

Zugaro et al., "Retinol binding protein 4, low birth weight-related insulin resistance and hormonal contraception" Endocrine (2007) 32(2):166-169.

International Search Report for application No. PCT/US2009/044919 dated Aug. 24, 2009.

Cabre et al., "Adipose Tissue-Derived Lipocalins RBP4 and FABP4 Induce Atherogenic Dyslipidemia in Diabetes" Atherosclerosis Supplements (2008) 9(1):19.

Steinmetz, "Lipid-lowering therapy in patients with type 2 diabetes: the case for early intervention" Diabetes/Metabolism Research and Reviews (2008) 24(4):286-293.

Wu et al., "Fenofibrate reduces serum retinol-binding protein-4 by suppressing its expression in adipose tissue" Endocrinology and Metabolism (2008) 296(4):E628-E634.

European Search Report for application EP 09751618.1 dated Apr. 27, 2012.

* cited by examiner

SEQUENCE LISTING

```
<160> NUMBER OF SEQ ID NOS: 86

<210> SEQ ID NO 1
<211> LENGTH: 1176
<212> TYPE: DNA
<213> ORGANISM: Mus musculus

<400> SEQUENCE: 1
tgggaaagcc agggcctgga cgctaatgtt ccaggctaca tcataggtcc cttttcgctc      60
agtgaggcca ccatcaccac accatggcca cgtaggcctc cagccagggc aacaggacct     120
ggaggccacc caagactgca gctggctgcc gctgggtccc cgggccagct cttggccccg     180
atggatcctc tgggctggag agtttggctc caccgagacc accctgagcg gagctcggag     240
cataggcgac gtgggacggc aaggctgacg gagggcccc gcgtgcgttc aggaggcaga      300
ctccggggtg agatggagtg ggtgtgggcg ctcgtgctgc tggcggctct gggaggcggc     360
agcgccgagc gcgactgcag ggtgagcagc ttccgagtca aggagaactt cgacaaggct     420
cgtttctctg ggctctggta tgccatcgcc aaaaaggacc ccgagggtct cttttttgcaa    480 gacaacatca tcgctgagtt ttctgtggac gagaagggtc atatgagcgc cacagccaag     540
ggacgagtcc gtcttctgag caactgggaa gtgtgtgcag acatggtggg cactttcaca     600
gacactgaag atcctgccaa gttcaagatg aagtactggg gtgtagcctc ctttctccag     660
cgaggaaacg atgaccactg gatcatcgac acggactacg acaccttcgc tctgcagtac     720
tcctgccgcc tgcagaatct ggatggcacc tgtgcagaca gctactcctt tgtgttttct     780
```

| | |
|---|---|
| cgtgacccca atggcctgag cccagagaca cggaggctgg tgaggcaacg gcaggaggag | 840 |
| ctgtgcctag agaggcagta cagatggatc gaacacaatg gttactgtca aagcaggccc | 900 |
| tccagaaaca gtttgtagca acgtctagga tgtgaagttt gaagatttct gattagcttt | 960 |
| catccggtct tcatctctat ttatcttaga agtttagttt cccccacctc ccctaccttc | 1020 |
| tctaggtgga cattaaacca tcgtccaaag tacatgagag tcactgactc tgttcacaca | 1080 |
| actgtatgtc ttactgaagg tccctgaaag acgtttgagg cttgggattc caaacttggt | 1140 |
| ttattaaaca tatagtcacc aaaaaaaaaa aaaaaa | 1176 |

<210> SEQ ID NO 2
<211> LENGTH: 11001
<212> TYPE: DNA
<213> ORGANISM: Mus musculus

<400> SEQUENCE: 2

| | |
|---|---|
| aaaaaagttt gcataacaac acacaacact tgtgtctaca ctgaactcat agttctttgt | 60 |
| ttacagtaca atagttattt atataacatg tacattgtat taaacattat aatccagaga | 120 |
| agactaaaat acacacaagg gtgtatatag attatattca aatgcatcct tttctacaaa | 180 |
| ggatttgtgg ggcataaggt actggaatca atgccccagt tgaaactgag aggcaagaaa | 240 |
| tgcatccttt ggtaaaacta gtccagtcaa atttccagt tagcctcctg gccagaaaca | 300 |
| ctcttcccta gttgtagagt cctatggaaa taaaacatgg tctctggtgc cacagagact | 360 |
| acaaggagca caatgggtgc aggggtggag agagaaccag gcaggtgaat gtccaaaagc | 420 |
| tcacaggaag ctgaaggagg ccgcaggtat ctctgcaagg ttgccaggca tggctaaggt | 480 |
| gcttgttgaa agaaatggca acttagttct ttctgtggcg tctctgtctc tcctcctttc | 540 |
| cccatctcct cttatatagc tatggcagag tggtcaatgt actctcatat gctcagactt | 600 |
| tgggcaatgg agacacaaat actttctcgt caaaaaaaat tttttttttt cccactaaat | 660 |
| ctcatttggt cgaaatcttc ctccttttaa ctgctaggtt cagtttgaca gatcgcaaac | 720 |
| tccaaataca gagggaaatg tagagttata tcgtgcccata ggcaaaaaaa aaaaaaaaa | 780 |
| aaaaaaaaaa aaaaaaaaaa aaaaaaaaaa atcaaccctt caacagcttt ttttggctac | 840 |
| taccattaag gttatggaat tctttccctc tccttttct cttcctgagc cagttttcct | 900 |
| cgctgttctg gaaataaata aatcctaata tggcttagaa ataaaaatgc atggtaaaca | 960 |
| cttggcaatt atgttttca gtgtggtttc aggggagtgt ggcaagagaa gtggacgatc | 1020 |
| aaccactcgg ccattggcgc tgagaaaata tttcctgtcc tgaccaggtt gcgtttctag | 1080 |
| agaatatttta acagggagcg gtttagtcct tctaaagatg atgaaatgaa agaataaata | 1140 |
| ttgacccaaa cagcaccaca actcatcaaa gagtaaaata tgcccttct caaaggggga | 1200 |
| aaaaaaaaca gccaaaatat gccaaaaagc ttctcacaac agctcctcag tagaagcagg | 1260 |
| ggccacttgg gaaagccagg gcctggacgc taatgttcca ggctacatca taggtccctt | 1320 |
| ttcgctcagt gaggccacca tcaccacacc atggccacgt aggcctccag ccagggcaac | 1380 |
| aggacctgga ggccacccaa gactgcagct ggctgccgct gggtcccgg gccagctctt | 1440 |
| ggccccgatg gatcctctgg gctggagagt ttggctccac cgagaccacc ctgagcggag | 1500 |
| ctcggagcat aggcgacgtg ggacggcaag gctgacggag gggccccgcg tgcgttcagg | 1560 |
| agtgagtcag ggagcgttat gcaagctcgg ccgccccccc ccctcccgcc ccggcacct | 1620 |
| ccccgcggtc tttcaccccg cgcggttacg aaagcgcgac cccctccccc cggagctata | 1680 |
| aaggaccgac ggccgctcgg ctccgtcgct ccacgcgcgc gcgaacgcgg cggccaggct | 1740 |

```
tgcacgcggc tcctgctggt gagccgccgc gcgctccccc ggggacctgc agggcggggt    1800
ggggcgggag ggggcgacgg gcggcctcgg tcctccggcc ccgcgtttac cctgcgcctg    1860
tcccgcaggg cagactccgg ggtgagatgg agtgggtgtg ggcgctcgtg ctgctggcgg    1920
ctctggggag cggcagcgcc gagcgcgact gcagggtgag cagcttccga gtcaaggaga    1980
acttcgacaa ggctcgtgta ggtatcagcc cgggttcccc gattcctgcg ggtcagaggt    2040
ggagcccaga ctccagtccc tagctctctc atctctttct cagttctctg gctctggta    2100 tgccatcgcc aaaaaggacc ccgagggtct cttttttgcaa gacaacatca tcgctgagtt    2160
ttctgtggac gagaagggtc atatgagcgc cacagccaag ggacgagtcc gtcttctgag    2220
gtcagtggcc tctggtgggc tgtgtgcggc gttccaaagt gcctcccacc ttgcctttgg    2280
ctccctggga gcccaacccct cactgggatg ggaaaagagt accttggatg aggtagaagc    2340 ccttttcctgg cttggctcag gattctcttg gcttttgcag caactgggaa gtgtgtgcag    2400
acatggtggg cactttcaca gacactgaag atcctgccaa gttcaagatg aagtactggg    2460
gtgtagcctc ctttctccag cgaggaagtg agtagtgggg catacatggc caaatcactg    2520
cgtttctgtt cagcggcacc gttgggaagg gcttcgagag gcagaaccct cagccctgtc    2580
tgaatttagg ggatgtggga ttagaagcga ctggattctc agcctaaaat acctaatcca    2640
agttcggaag ggccttttggg cttatcgggt accatttccc tgatcatcca ctgtgactta    2700
cttcacgctg tctcacacat taccactcca ctctgtctct tggagtggaa tctctgagac    2760
agtaggacaa tctggaacat cggcagagct agagaccgat atccaagagg agggaactat    2820
gtgtctgagc tgggtcacag cccaggcccc tcccggtgga ctcccagcca ggcagtgttc    2880
tggaagcaat agtctccttt ccttaaatac tcatatgcaa ggcaggattt tgagaactcc    2940
caacaaagtt ccctaaagtt tgggattctt ctcaggacac acaattgaca tgttctttga    3000
ctcccccagc ccatttcact taaattatag atccgaaagc tacttgataa ctaaggaata    3060
atttagggtg ggaagaagta ttgtgagatc tcagaaagaa ggaactaatc tcagccctaa    3120
ggcaatggct ctagacctgc gttctgagac ccttgggggt caaatgacct tttcacggga    3180
gccagctcaa gctgtctaaa aacacagacg tttacttaca ttatgattca tagcagtagc    3240
aaaaattaca gttatgaagt agcaacaaaa ataattctat ggttggtggt tattgcaaca    3300
tgaggagctg tattaaagga tggcgggatt aggaagggtg agaatcactc tcctagggtg    3360
aaggggggtg tccgggataa atttctcctt attttaacct tttcagaaag accgtgtgca    3420
gggtaatagt taagtatgcc acgttaaagt tagactgact gagtgctgga gatgtagctc    3480
attggcagaa caattgtcgc acattcacga ggttctggaa tctatctcca aacatatggg    3540
tgcagggcgt tgtgcataca cacttgtgtg tgtgcgcgtg tgtgcgcgcc cggcttgtgc    3600
atgcacactt tgtgtgtgtg tgtgtgtgtg tgtgtgtgca cgcgcgtgtg ctccagagtg    3660
cgtgctcacg aactcctgtg cacacacaca cacacacgtt catcccaca cacccacaac    3720 ctaagttcaa atcctaacta aactattacc cgtgggaccc tgagttgtta cctaactttt    3780
ctgtgcccca gtttcctcct tgtgcaaagt agacagaatc acaacatgca gatcgtggga    3840
ctgtgaagat ataatgcatg ggtgtgcaga aagcgccagg aagagtgtct gaggcataaa    3900
ttctgtgttg gatagcattt cttcttagta aagaaatctt actcttaggt aaagaaatca    3960 tagtttata ttctggctct cgagtgggag aactcagata tcttcaggta caagtttact    4020
actatttaag ttaagaaatg agtgcaccag gggcacacac acagctaact gttgggacct    4080
ggtgacacct cttagcccaa atgatgtaaa gaaacatttc ccctgccttt accctgtttt    4140
```

```
tctgagtcta ccaactcact tgaggtgtct gccttccact gtttaatatg cttgtctggg    4200
ggcctccttc acaaactcca aattcattcc ttgtgctaat ttccttcctt gaccttgacc    4260
ttacattaag cgtgaatttg dacaggaggt tgcaggccac tcagagaggt ctctctcctt    4320
gtcacaattt acaccttacc agatggatac atttgtaata aggcaggctg attggaaata    4380
actcaaggca agttaaatat aataaacatc tatagctgat gctggagttc aagaaaatt     4440 ctggccatcc tgaatcccca ttgtagtaga ttagagagct aaaggcatag tggccatgac    4500
catgagcttg tcagctgggt ggaatgagga gctgactcct tggcccttt ttgactttt      4560 cttttccccca taaatggcct gggaatcgac cccagaccat gttaggcaag agctctaata   4620
ccatgctccc tccttcagtg caagcagact gctctggtct gctgcccct ccttgagcat     4680 gctctgtact gatctctttc tcttctcatt ctatgcacgg agtgagacat ctcaaaagta    4740
aaggtcattg ctatcagcct gtattggtca aatatagaca tagttgcaga ctaggttctc    4800
taaaatctga tttcctctgc tctcaactta agttaaggaa tagttcctat ttaaaagatt    4860
gtcgaaagaa ctagtcatgg taacacatga acgagtttag cttggtgcct aataagagct    4920
tcttaaatat tggctacgat cattattttg ttatgccctc ccggaaaaac atgaactaag    4980
acttctttct tccttgtctc aaataaatgt tgccactctc ttggccaaag gatccttgtt    5040
aatagaggaa caattattta atgtgaggct tgaacatcta catcagtgtt tctccaagtc    5100
actgccctct ggccaacttc cattagatca gctgcagtac ttttttcaaag tgcagattta   5160 tgggtccgaa ccccagactt tctgaatcag aaactcttgg gagtagaaca ctgttatctc    5220
cattttcaat acattcctct ggtgagttcc ttctgcactg tgaagtttga gaaccagcgg    5280
gctagataat tcaaaccatg ggaggtctca gacttcattc ctttaccaag gttattgcta    5340
tgactgtttg gaagtggact ggaatctgta ccctggctgg tttaggtctt aggtccttct    5400
gcctgcgaat cataggaagc ccctcccctg gaagacacag gtttcgggag ccaagggaac    5460
cttttcgagg gtcacagcaa gtgagagcag tgaatggcag atcttttaag aaagctaatc    5520
accaagaccc tctgttgaac atttgaaacc aggcatttct aagctctcca cctatcagtt    5580
ccgttcactg tagacacggc cgcagtgtaa tgttatattc tggattttgg aggggagtca    5640
gggactgcca gacattatag tctctgcctc aggcactctc gccacagtcc attgtgtgca    5700
gttaggtgat gtcggggaag acttggcatg tctctttcag aggaacccta cccagaggca    5760
ggagggctaa gttcattctt tcaagctgtg ccctggcaga tcttctcttg caaatactgt    5820
taggagggag tgtctggtga agtttgttag gactcttcat gattgaacta ttctgccaaa    5880
aagaacctgg agacaaacca aaccaattca ggccttcttt taagttaaaa gcagtagcca    5940
agtgcactac aaccagacat tgaaagttag ctcttaggtc gtattttata ttccagcaac    6000
catttgggga taaaaattgt taagctgccg gtgtgtcagg ctaagtgcgt agacaatgag    6060
ctgagatact agttgaaaca tgagtgcctt tttgtctaag acaggctcct gggatgccct    6120
ttatgccacc gtgatcccat gacaccatcc agagatggga agactctgcc ccatactcag    6180
gagcctgggg aggagggtgg agcctgggga ggagggtgga gcctgggagg agggtggagc    6240
ctgggaggag ggtggagcct gggaggaggg tggagcctgg ggaggagggt ggagcctgag    6300
gaggaggagg gtggagcctg aggtggccc agctgcagcc atgtggctcc cctctattcc     6360
tggtccgtct actgaggaac ttcatggtca ctgcctagca gatgaattgt tgggcaggga    6420 catttcaag ccagggctct gaaagcctgg aagataaggg agtggctcat tcctcttctt      6480
gtgaggcaga ggctgaggca gaggggggctg catatcctct cctgagcagt gatcctgtgg    6540
```

```
gtctgggcgc agggggctgag ccagacccta ggctggtatc tcaagtatcc agagagagcc    6600
acacacactg ttgacttaca gtggggacat gagtggcctc acgtgatgtc atgtttggac    6660
atctgggttg ctctgtcttc ctccaatatg aacccttaca taggtagatg gttccttgct    6720
ttagacctgg gtgtgagaag gaaaaaaaaa tttaaaaaca aactgtttgt tcttgtcccc    6780 tttgaccccca atttacctag tgtctggaga cactggcaga ggttaggtgt gcaagctctg    6840
gttaggtgtc cagctctgcc cagcgccctg gtcctttggg aattacttct cttttctgtg    6900
tctctgtctg ctcatctgta atatggagta atagtgtatg gttttgaaag atacaagaaa    6960 tacccccgcgc gcgtgcgtgc gtgcatgcgt gcgtgcgcgt gcgcgtgcgt gcgtgcgtgc    7020
gtgcgtgcgt gcgtgcgtgt gtgtgtgtgt gtgtgtgtgt gtgtgtgtgt gtgtgtgtgt    7080
acatgcatcc attgtatgca tgtgagtgtg aaggtgtatg aacctgccca gagcagagca    7140
ctgggtatca gaacacttgc tgacagcctc attcctttga agcagtcttt cactgcaccg    7200
gaagcttgct gtttctgcta ggctgacttg ccagtaacct cccaggatct gcctgtcccc    7260
gcctcccaga gctaggtttt caggcccaca tagcagtctg gcattttaca tgggaatttg    7320
aattcaggtc cttatgcttg cagagtaaac acaattaccc actgggctat atctccttaa    7380
caaccctgcc cactccaaat acaaattcta atgagtattt gaagctggat agtgagcatc    7440 ttttgccccct aggcatccca gctgtcaacc ggaggaagtg aataggatgc ctaagcgtga    7500
atcagggtag agcctgaaaa actattacca tctgattggc atcctctagc ccacccaata    7560
ggaaaacagt ggggctaaga gagcggggg gtggggtaga ttctgtggag cattgataag    7620
tcgtgacctc aagttgttgg tggcataagt tgagggcgat agacattaga cagagacaca    7680
tgttattgga gggtgtagta gtgaagacag tagtacagct gcagggggtcc tttagaaaag    7740 cattgtgcta tcagttatca agaagctgac gacgagaatg aggtgccctc tataccagga    7800
caagatttgt gtcttctgct accaaggaaa cactgacatg aaggacatgc cttctgtgcc    7860
aggacacctt tccgggaaga gagcaagatc ctttctcgct tgcccagttg tccagaagct    7920
gtcaggaatc tctgcagcct cctttcacta aggaaaggct gcgagttcca tggcagcagt    7980
ggtagcaagt tggtcaggtc tctggggcca ctgtgtctct ctgacttaca gacgatgacc    8040
actggatcat cgacacggac tacgacacct tcgctctgca gtactcctgc cgcctgcaga    8100
atctggatgg cacctgtgca gacagctact cctttgtgtt ttctcgtgac cccaatggcc    8160
tgagcccaga gacacggagg ctggtgaggc agcggcagga ggagctgtgc ctagagaggc    8220
agtacagatg gattgaacac aatggtgagc aagtcttcct ggggaacttg gcagggctgg    8280
gtcagtaaga gggtgcaaca tcgatctttg caagtgggtt gcctgaggag cctccttttgg    8340 gccaaggctt ggcccttctt gattaaattt ttcctagggc tttgccatca gccatacgga    8400
gaagggccca aaggttcttt tccccaaacc ctagcacttt caataaccaa agctgtgggg    8460
tcactctctt ctccttatat tttactcccc acatttgctt atgatgccac aaccctgaga    8520
aactattctg caggaattag agtttggtgg agaagtgtcc ctagtaaaga actggctggg    8580
gcatgcagcc attttatgta aaaccataaa caaaggcatc aatatagcag gtctttaaag    8640
actggtgcct tgaaatgttc tttattcgtc acaaaaccaa acaccactta attagctcac    8700
ggggtctcca cttgagtttc ctaggggaag tctccaggat aatcgtggga tactttaata    8760
tctattgtcc ttaacggatc ctaacttgaa actcagaaac atggtgggga agtgggctac    8820
ctattttgaa ttgacctgca ctcatatgta tgggcaattg agcctcaaaa ttccaaaaag    8880
ggtcctgctg gggtgtagaa aaagaacatt tttcttaggc atctcagtga tccaatatac    8940
```

```
caacaacgtg agctcagacg tatatagatt tgaaagtgcc accaggggtg gactggggga      9000
gggagctgaa agtagggcca gtgaaggatt gtgtcacccc gggcaccaca gaagctttca      9060
cctaactcac cccagttaac ccttggagac actttatagc tatacatact ccaccagtga      9120
gaaagttgga agctaaggaa agttaaatac attgccttcg atctccaata gatggataag      9180
ttgaatgcaa actcagatgt ctgtcaccat ggagttcctt gtggggcctc ctggtgaccc      9240
gggcaagaca gggacatcat gtaggctatg aagctatagc agtgaagcgg aggtcaggta      9300
ggtgtggccc tcatgtctca aggcaggagg gtgggcttca aaggcacttg gagatgcaat      9360
gggtgggaat caattgtggg ataaatggat agtgactcat gccgcaggtc ctgtgccctc      9420
agccatgctg ctccctggag gatttagaga gcttgagcat caactgtcag ggaacttgtg      9480
aagtaagcca taccgatgcc tatgagtggc cacttgctct atggctgccc aggtgttcat      9540
taatctacga aagcactgaa ctaacgatcc atctctctca ttatggtctt attttctgta      9600
tttcaggtta ctgtcaaagc aggccctcca gaaacagttt gtagcaacgt ctaggatgtg      9660
aagtttgaag atttctgatt agctttcatc cggtcttcat ctctatttat cttagaagtt      9720
tagtttcccc cacctcccct accttctcta ggtggacatt aaaccatcgt ccaaagtaca      9780
tgagagtcac tgactctgtt cacacaactg tatgtcttac tgaaggtccc tgaaagatgt      9840
ttgaggcttg ggattccaaa cttggtttat taaacatata gtcaccatct tcctatgagt      9900
tgaagactta tttgtggcgg ggttgcactt ttagaggtca agaccagatt aaagactggt      9960
ttttaacttc ctaagaaagg gttttaagat ccaagaagat cttttaaaaat ggcctaccaa     10020 ggcactggca gccagagagg aagtgaatgg ccacaccatc aaaccaatgg ctgtcagccc     10080
agggcccgtg aggtgagcag ggcagaaggc tcacctctgg aaagagttgg gtcagagaga     10140
actctgggaa gccactctgt tcttcattgc ttctagtgtg actcacgttg tttttcagtt     10200
gggtgcagaa cgttgaagag caagctgcct tggtgttccc ttggggaagt ttagggatgg     10260
ggctctggaa gccagcaccc ctaacaagac tgtgcaggaa ataacgaggt gggagaggaa     10320
gcagccagga ccataccatc agcagtaatt gtctcggttc cccaggggtt cctgggagcc     10380 tgttttagc aaggccgtgg tgccagagga tctgggtttt aaatctaatc tagtttggag      10440
ctgtgagact ggggctggt tttgtggctt ctctcatgaa acttgggaag caattgctcc       10500
ctgcttgatg gataaataga cagtccatac aatgtctgca agcatgcgaa ggagctgtga     10560
gaaacacttc ggacaggagg acatctgtga agtgtgttgg cgttgttttg ctgatgttt       10620 taaggaccgt ggggagctca caccaagcgc ctgtgagcct cgttgtctag caagggcaga     10680
ggaaacagcc atgcacgaga aaactcagct ttccactctt agagcaagct gacggtctgg     10740
ctcctcagct ccggtttgac accacagcca taagatattc acatacccat tcaaaacagc     10800
atcaaatcca ttaagtccac aggaacaaag gcgccttatt atttcgtact tactgtcatg     10860
gtcaccatga atcagacctc agacctacac attggcattt cctggggctc agcggttgaa     10920
tgtggtttct ttcctttctt caccttctcc caggctattt cataaaacca tgggttccta     10980
aacaccatct ctattcccca a                                               11001
```

<210> SEQ ID NO 3
<211> LENGTH: 920
<212> TYPE: DNA
<213> ORGANISM: Mus musculus

```
<400> SEQUENCE: 3
ggctccacgc gcgcggcgaa cgcgggcggc caggcttgca cgcggctcct gctgggcaga    60
ctccggggtg agatggagtg ggtgtgggcg ctcgtgctgc tggcggctct gggaggcggc   120
acgcgagcgc gactgcaggg tgagcagctt ccgagtcaag gagaacttcg acaaggctcg   180
tttctctggg ctctggtatg ccatcgccaa aaaggacccc gagggtctct ttttgcaaga   240
caacatcatc gctgagtttt ctgtggacga aagggtcat atgagcgcca cagccaaggg    300
acgagtccgt cttctgagca actgggaagt gtgtgcagac atggtgggca cttttcacaga   360 cactgaagat cctgccaagt tcaagatgaa gtactgggt gtagcctcct ttctccagcg    420
aggaaacgat gaccactgga tcatcgacac ggactacgac accttcgctc tgcagtactc   480
ctgccgcctg cagaatctgg atggcacctg tgcagacagc tactcctttg tgttttctcg   540
tgaccccaat ggcctgagcc agagacacg gaggctggtg aggcagcggc aggaggagct    600
gtgcctagag aggcagtaca gatggattga acacaatggt tactgtcaaa gcaggccctc   660
cagaaacagt ttgtagcaac gtctaggatg tgaagtttga agatttctga ttagctttca   720
tccggtcttc atctctattt atcttagaag tttagtttcc cccacctccc ctaccttctc   780
taggtggaca ttaaaccatc gtccaaggta catgagagtc actgactctg ttcacacaac   840
tgtatgtctt actgaaggtc cctgaaggat gtttgaggct ggggtatcc aaacttgggt    900 tattaacata tagtgacatc                                                920

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
ccttccctga aggttcctcc                                                 20

<210> SEQ ID NO 5
<211> LENGTH: 941
<212> TYPE: DNA
<213> ORGANISM: H. sapiens

<400> SEQUENCE: 5
cgcctccctc gctccacgcg cgcccggact cggcggccag gcttgcgcgc ggttcccctc    60
ccggtgggcg gattcctggg caagatgaag tgggtgtggg cgctcttgct gttggcggcg   120
ctgggcagcg gccgcgcgga gcgcgactgc cgagtgagca gcttccgagt caaggagaac   180
ttcgacaagg ctcgcttctc tgggacctgg tacgccatgg ccaagaagga ccccgagggc   240
ctctttctgc aggacaacat cgtcgcggag ttctccgtgg acgagaccgg ccagatgagc   300
gccacagcca agggccgagt ccgtcttttg aataactggg acgtgtgcgc agacatggtg   360
ggcaccttca cagacaccga ggaccctgcc aagttcaaga tgaagtactg gggcgtagcc   420
tcctttctcc agaaaggaaa tgatgaccac tggatcgtcg acacagacta cgacacgtat   480
gccgtgcagt actcctgccg cctcctgaac ctcgatggca cctgtgctga cagctactcc   540
ttcgtgtttt cccgggaccc caacggcctg cccccagaag cgcagaagat tgtaaggcag   600
cggcaggagg agctgtgcct ggccaggcag tacaggctga tcgtccacaa cggttactgc   660
gatggcagat cagaaagaaa ccttttgtag caatatcaag aatctagttt catctgagaa   720
cttctgatta gctctcagtc ttcagctcta tttatcttag gagtttaatt tgcccttctc   780
```

```
tccccatctt ccctcagttc ccataaaacc ttcattacac ataaagatac acgtgggggt    840
cagtgaatct gcttgccttt cctgaaagtt tctggggctt aagattccag actctgattc    900
attaaactat agtcacccgt gtcctgtgaa aaaaaaaaa a                          941
```

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6

```
agccagctgc agtcttgggt                                                 20
```

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7

```
ccagcggcag ccagctgcag                                                 20
```

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8

```
ggaatcccaa gcctcaaacg                                                 20
```

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9

```
caagtttgga atcccaagcc                                                 20
```

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10

```
tcccagagcc gccagcagca                                                 20
```

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11

```
tgctcaccct gcagtcgcgc                                                 20
```

```
<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
cgagccttgt cgaagttctc                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
agaaacgagc cttgtcgaag                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
cccagagaaa cgagccttgt                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
taccagagcc cagagaaacg                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
tggcatacca gagcccagag                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
ggcgatggca taccagagcc                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 18
tcctttttgg cgatggcata                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
tgcaaaaaga gaccctcggg                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
tgtcttgcaa aaagagaccc                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
gatgttgtct tgcaaaaaga                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
gcgatgatgt tgtcttgcaa                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
actcagcgat gatgttgtct                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
agaaaactca gcgatgatgt                                              20
```

```
<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
tccacagaaa actcagcgat                                          20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
gttgctcaga agacggactc                                          20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
tcccagttgc tcagaagacg                                          20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
acacttccca gttgctcaga                                          20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
tgcacacact tcccagttgc                                          20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
atgtctgcac acacttccca                                          20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide
```

-continued

<400> SEQUENCE: 31
ccaccatgtc tgcacacact                                          20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
agtgcccacc atgtctgcac                                          20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
tgtgaaagtg cccaccatgt                                          20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
ttgaacttgg caggatcttc                                          20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
ttcatcttga acttggcagg                                          20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
cccagtactt catcttgaac                                          20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
ctacacccca gtacttcatc                                          20

```
<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
ggaggctaca ccccagtact                                           20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
agaaaggagg ctacacccca                                           20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
gctggagaaa ggaggctaca                                           20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
cgtttcctcg ctggagaaag                                           20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
cgatgatcca gtggtcatcg                                           20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
actgcagagc gaaggtgtcg                                           20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 44
agattctgca ggcggcagga                                                        20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
ccatccagat tctgcaggcg                                                        20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
gcacaggtgc catccagatt                                                        20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
tgtctgcaca ggtgccatcc                                                        20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
ctttgacagt aaccattgtg                                                        20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
caaacttcac atcctagacg                                                        20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
cagaaatctt caaacttcac                                                        20
```

-continued

```
<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
gaaagctaat cagaaatctt                                             20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
gaccggatga aagctaatca                                             20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
taaatagaga tgaagaccgg                                             20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
ttctaagata aatagagatg                                             20

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
ttaatgtcca cctagagaag                                             20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
tggacgatgg tttaatgtcc                                             20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 57
tctcatgtac cttggacgat                                               20

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
gtcagtgact ctcatgtacc                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
tacagttgtg tgaacagagt                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
ttcagtaaga catacagttg                                               20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
tccttcaggg accttcagta                                               20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
ccaagcctca aacatccttc                                               20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
ccaagtttgg ataccccaag                                               20
```

```
<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 64
ctatatgtta ataacccaag                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
gatgtcacta tatgttaata                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 66
gagaagcttt ttggcatatt                                              20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
ttcccaagtg gcccctgctt                                              20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
tgtagcctgg aacattagcg                                              20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
gcgaaaaggg acctatgatg                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 70
tgatggtggc ctcactgagc					20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
gtcagctgca gtcttgggtg					20

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 72
agcccagagg atccatcggg					20

<210> SEQ ID NO 73
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 73
gtcagccttg ccgtcccacg					20

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 74
ggcggctcac cagcaggagc					20

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
ggccactgac ctcagaagac					20

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 76
tagctttcgg atctataatt					20

```
<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 77
tggtttcaaa tgttcaacag                                               20

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 78
gtgcctgagg cagagactat                                               20

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 79
gtgggctaga ggatgccaat                                               20

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 80
acttgctcac cattgtgttc                                               20

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81
ctcactggtg gagtatgtat                                               20

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
atgagtcact atccatttat                                               20

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 83
tgacagtaac ctgaaataca                                                    20

<210> SEQ ID NO 84
<211> LENGTH: 904
<212> TYPE: DNA
<213> ORGANISM: Rattus norvegicus

<400> SEQUENCE: 84
gcggcggcca ggcttgcacg cggcttctgc tgggcagact ccggtgtgaa atggagtggg        60
tgtgggcgct cgtgctgctg gcggctctgg gaggcggcag cgccgagcgc gactgcaggg       120
tgagcagctt cagagtcaag gagaacttcg acaaggctcg tttctctggg ctctggtatg       180
ccatcgccaa aaaggatccc gagggtctct ttttgcaaga caacatcatc gctgagtttt       240
ctgtggacga agggtcat atgagcgcta cagccaaggg acgagtccgt cttctgagca        300
actgggaagt gtgtgcagac atggtgggca ctttcacaga cacagaagat cctgccaagt       360
tcaagatgaa gtactggggt gtagcctcct ttctccagcg aggaaacgat gaccactgga       420
tcatcgatac ggactacgac accttcgctc tgcagtattc ctgccgcctg cagaatctgg       480
atggcacctg tgcagacagc tactcctttg tgttttctcg tgaccccaat ggcctgaccc       540
cggagacacg gaggctggtg aggcagcgac aggaggagct gtgcctagag aggcagtaca       600
gatggatcga gcacaatggt tactgtcaaa gcagaccctc aagaaacagt tgtagcaac        660 gtcaaggatg tataaagttg gaaaacttct gattagctct catccagtct tcatctctat       720
ttatcttaga gtttagtttt ccccacctcc cctcccttct ctaggtggac attaaaacca       780
tcgtccaaat acatgggaat gcctgaatcc attcacacaa acgtgtatct tactgagaag       840
ttccccgaga gacgtttgag gcttgggatt ccaaacttga tttattaaac gtatagtcac       900
catc                                                                    904

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 85
tacaaatggg atgctactgc                                                    20

<210> SEQ ID NO 86
<211> LENGTH: 1052
<212> TYPE: DNA
<213> ORGANISM: mus musculus

<400> SEQUENCE: 86
acacagatcc acaagctcct gacaggatgg cttcccttcg actcttcctc ctttgcctcg        60
ctggactggt atttgtgtct gaagctggcc ccgcgggtgc tggagaatcc aaatgtcctc       120
tgatggtcaa agtcctggat gctgtccgag gcagccctgc tgtagacgtg gctgtaaaag       180
tgttcaaaaa gacctctgag ggatcctggg agccctttgc ctctgggaag accgcggagt       240
ctggagagct gcacgggctc accacagatg agaagtttgt agaaggagtg tacagagtag       300
aactggacac caaatcgtac tggaagacac ttggcatttc cccgttccat gaattcgcgg       360
atgtggtttt cacagccaac gactctgccc atcgccacta caccatcgca gccctgctca       420
gcccatactc ctacagcacc acggctgtcg tcagcaaccc ccagaattga gagactcagc       480
```

```
ccaggaggac caggatcttg ccaaagcagt agcatcccat ttgtaccaaa acagtgttct    540
tgctctataa accgtgttag cagctcagga agatgccgtg aagcattctt attaaaccac    600
ctgctatttc attcaaactg tgtttctttt ttatttcctc atttttctcc cctgctccta    660
aaacccaaaa tttttaaag  aattctagaa ggtatgcgat caaacttttt aaagaaagaa    720
aatacttttt gactcatggt ttaaaggcat cctttccatc ttggggaggt catgggtgct    780
cctggcaact tgcttgagga agataggtca gaaagcagag tggaccaacc gttcaatgtt    840
ttacaagcaa aacatacact aacatggtct gtagctatta aaagcacaca atctgaaggg    900
ctgtagatgc acagtagtgt tttcccagag catgttcaaa agccctgggt tcaatcacaa    960
tactgaaaag taggccaaaa aacattctga aaatgaaata tttgggtttt tttttataac   1020
ctttagtgac taaataaagc caaatctagg ct                                 1052
```

METHODS FOR MODULATING EXPRESSION OF RBP4

CROSS REFERENCE TO RELATED APPLICATIONS

This application is a 371 National Stage of International Application No. PCT/US2009/044919, filed on May 21, 2009, which claims benefit under 35 USC 119(e) to U.S. Provisional Application No. 61/128,628, filed May 22, 2008, which are incorporated herein by reference.

SEQUENCE LISTING

The present application is being filed along with a Sequence Listing in electronic format. The Sequence Listing is provided as a file entitled BIOL0103WOSEQ.txt, created on May 21, 2009, which is 36 Kb in size. The information in the electronic format of the sequence listing is incorporated herein by reference in its entirety.

FIELD OF THE INVENTION

This invention is related generally to methods and agents for modulating Retinol-Binding Protein 4 (RBP4). More particularly, the present invention includes and can relate to methods of inhibiting RBP4 with a RBP4-specific inhibitor to treat or prevent metabolic-related and cardiovascular-related disorders, particularly including disorders associated with dyslipidemia, diabetes, and obesity.

BACKGROUND OF THE INVENTION

Insulin, the major metabolic hormone for the regulation of glucose homeostasis, mediates its action by reducing hepatic glucose output and by increasing the rate of glucose uptake by skeletal muscle and adipose tissue (M. Bliss, Univ. of Chicago Press, 1982). Glucose uptake into muscle cells and adipocytes by insulin is carried out by the glucose transporter GLUT4. Some insulin-related metabolic disorders are insulin resistance, diabetes mellitus and metabolic syndrome.

Insulin resistance is the condition in which insulin, even though present in normal amounts, is unable to produce a normal insulin response from fat, muscle and liver cells. Insulin resistance in fat cells leads to increased hydrolysis of stored triglycerides and increased mobilization of stored lipids, which in turn, elevates free fatty acids in the blood plasma. Insulin resistance in muscle cells reduces glucose uptake and local storage of glucose as glycogen, whereas insulin resistance in liver cells reduces storage of glycogen, making it unavailable for release into the blood when blood insulin levels fall. High plasma levels of insulin and glucose due to insulin resistance often lead to metabolic syndrome and type 2 diabetes, including its complications.

Diabetes affects over 18.2 million people in the United States, representing over 6% of the population. Diabetes is characterized by the inability to produce or properly use insulin. Diabetes type 2 (also called non-insulin-dependent diabetes or NIDDM) accounts for 80-90% of the diagnosed cases of diabetes and is caused by insulin resistance. Insulin resistance in diabetes type 2 prevents maintenance of blood glucose within desirable ranges, despite normal to elevated plasma levels of insulin. Additionally, glucotoxicity, which results from long-term hyperglycemia, induces tissue-dependent insulin resistance (Nawano et al., Am. J. Physiol. Endocrinol. Metab., 2000, 278, E535-543) exacerbating the disease. Chronic hyperglycemia is also a major risk factor for diabetes-associated complications, including heart disease, retinopathy, nephropathy and neuropathy.

Diabetes and obesity (sometimes collectively referred to as "diabesity") are interrelated in that obesity is known to exacerbate the pathology of diabetes and greater than 60% of diabetics are obese. Most human obesity is associated with insulin resistance and leptin resistance. In fact, it has been suggested that obesity may have an even greater impact on insulin action than diabetes itself (Sindelka et al., Physiol Res., 2002, 51, 85-91). Additionally, several compounds on the market for the treatment of diabetes are known to induce weight gain, a very undesirable side effect to the treatment of this disease.

Cardiovascular disease is also interrelated to obesity and diabetes. Cardiovascular disease encompasses a wide variety of etiologies and has an equally wide variety of causative agents and interrelated players. Many causative agents contribute to symptoms such as elevated plasma levels of cholesterol, including non-HDL cholesterol, as well as other lipid-related disorders. Such lipid-related disorders, generally referred to as dyslipidemia, include hypercholesterolemia and hypertriglyceridemia among other indications. Non-HDL cholesterol is firmly associated with atherogenesis and its sequalea, including cardiovascular diseases such as arteriosclerosis, coronary artery disease, myocardial infarction, ischemic stroke, and other forms of heart disease. These rank as the most prevalent types of illnesses in industrialized countries. Indeed, an estimated 12 million people in the United States suffer with coronary artery disease and about 36 million require treatment for elevated cholesterol levels.

Metabolic syndrome is a combination of medical disorders that increase one's risk for cardiovascular disease and diabetes. The symptoms, including high blood pressure, high triglycerides, decreased HDL and obesity, tend to appear together in some individuals. It affects a large number of people in a clustered fashion. In some studies, the prevalence in the USA is calculated as being up to 25% of the population. Metabolic syndrome is known under various other names, such as (metabolic) syndrome X, insulin resistance syndrome, Reaven's syndrome or CHAOS.

With the high prevalence of cardiovascular disorders and metabolic disorders there remains a need for improved approaches to treat these conditions; including reducing unwanted side-effects.

SUMMARY OF THE INVENTION

Provided herein are methods, agents and compositions for modulating RBP4. The agents and compositions include RBP4-specific modulators. RBP4-specific modulators include proteins, peptides, polypeptides, antibodies, antisense compounds, including oligonucleotides and antisense oligonucleotides, ssRNA, dsRNA molecules, ribozymes, triple helix molecules, siRNA and other RNAi compounds, and small molecule modulators. Any of the listed RBP4-specific modulators can be RBP4-specific inhibitors. As shown here, modulating the expression of RBP4 is a useful method for treating cardiovascular disorders and metabolic disorders, such as dyslipidemia, insulin resistance, type 2 diabetes, and metabolic syndrome. Therefore, among the objectives herein, it is an object to provide methods for the treatment of such diseases and conditions.

Also provided are methods of treating diseases and disorders. Included are methods of treating cardiovascular and metabolic diseases and disorders. The diseases and disorders include, but are not limited to, those associated with lipid dysregulation, fat dysregulation, adipocyte dysregulation, and glucose dysregulation.

Also provided are methods of treating multiple disease or disorders. The multiple diseases or disorders can include any of the disease and disorders provided herein. The multiple diseases and disorder can have one or more risk factors, causes or outcomes in common.

The present invention is also directed to methods of reducing risk factors associated with disease and causes of disease. Such diseases include cardiovascular and metabolic diseases such as, but not limited to diabetes, metabolic syndrome and atherosclerosis. Risk factors include, but are not limited to, lipid level, adiposity, and glucose level and insulin responsiveness.

In particular embodiments, methods of treatment include administering to a subject a RBP4-specific modulator, as described herein. In particular embodiments, a RBP4-specific inhibitor is administered, as described herein.

Methods of modulating RBP4 include methods of modulating levels of RBP4. The levels can include but are not limited to RBP4 mRNA levels and RBP4 protein levels. Modulation can occur in a cell or tissue. In a certain embodiment, the cell or tissue is in an animal, as described herein. In certain embodiments, the subject or animal is a human. In certain embodiments, RBP4 levels are reduced, as described herein. Such reduction can occur in a time-dependent manner or in a dose-dependent manner or both.

DETAILED DESCRIPTION OF THE PREFERRED EMBODIMENTS

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"Active pharmaceutical ingredient" means the substance in a pharmaceutical composition that provides a desired effect.

"Adipogenesis" means the development of fat cells from preadipocytes. "Lipogenesis" means the production or formation of fat, either fatty degeneration or fatty infiltration.

"Adiposity" or "Obesity" refers to the state of being obese or an excessively high amount of body fat or adipose tissue in relation to lean body mass. The amount of body fat includes concern for both the distribution of fat throughout the body and the size and mass of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese. The term "Obesity" as used herein includes conditions where there is an increase in body fat beyond the physical requirement as a result of excess accumulation of adipose tissue in the body. The term "obesity" includes, but is not limited to, the following conditions: adult-onset obesity; alimentary obesity; endogenous or metabolic obesity; endocrine obesity; familial obesity; hyperinsulinar obesity; hyperplastic-hypertrophic obesity; hypogonadal obesity; hypothyroid obesity; lifelong obesity; morbid obesity and exogenous obesity.

"Administering" means providing a pharmaceutical agent to an individual, and includes, but is not limited to administering by a medical professional and self-administering.

"Amelioration" refers to a lessening of at least one indicator, sign or symptom of an associated condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to an immunoglobulin molecule or immunologically active portion thereof characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region. The antibody can be a polyclonal, monoclonal, recombinant; e.g., a chimeric or humanized; fully human, non-human; e.g., murine; or single chain antibody.

"Antisense compound" refers to an oligomeric compound that is at least partially complementary to a target nucleic acid molecule to which it hybridizes. For example, "antisense compound targeted to RBP4" refers to an oligomeric compound at least partially complementary to the RBP4 nucleic acid molecule. In certain embodiments, an antisense compound modulates (increases or decreases) levels and/or expression of a target nucleic acid, as described herein. Antisense compounds include, but are not limited to, compounds that are oligonucleotides, oligonucleosides, oligonucleotide analogs, oligonucleotide mimetics, and chimeric combinations of these. Consequently, while all antisense compounds are oligomeric compounds, not all oligomeric compounds are antisense compounds.

"Antisense inhibition" means reduction of target nucleic acid levels, in the presence of an antisense compound complementary to a target nucleic acid, compared to target nucleic acid levels in the absence of the antisense compound.

"Antisense oligonucleotide" means a single-stranded oligonucleotide having a nucleobase sequence that will permits hybridization to a corresponding region of a target nucleic acid.

"ApoB-containing lipoprotein" means any lipoprotein that has apolipoprotein B as its protein component, and is understood to include LDL, VLDL, IDL, and lipoprotein(a) and can be generally targeted by lipid lowering agent and therapies.

"Atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

"Bicyclic nucleic acid sugar moiety" means a furanosyl ring modified by the bridging of two non-geminal ring atoms. A bicyclic sugar is a modified sugar.

"Body weight" refers to an animal's total weight, inclusive of all tissues including adipose tissue.

"Body fat content" refers to an animal's total amount of adipose tissue mass or weight.

"Cap structure" or "terminal cap moiety" means chemical modifications, which have been incorporated at either terminus of an antisense compound.

"Cardiovascular disease" or "cardiovascular disorder" refers to a group of conditions related to the heart, blood vessels, or the circulation. Examples of cardiovascular diseases include, but are not limited to, aneurysm, angina, arrhythmia, atherosclerosis, cerebrovascular disease (stroke), coronary heart disease, hypertension, dyslipidemia, hyperlipidemia, and hypercholesterolemia.

"Chimeric antisense compounds" means antisense compounds that have at least 2 chemically distinct regions, each region having a plurality of subunits.

"Cholesterol" is a sterol molecule found in the cell membranes of all animal tissues. Cholesterol may be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to cholesterol present in the plasma.

"Cholesterol absorption inhibitor" means an agent that inhibits the absorption of exogenous cholesterol obtained from diet.

"Co-administration" refers to administration of two or more agents to an animal. The two or more agents may be in a single pharmaceutical composition, or may be in separate pharmaceutical compositions. Both agents may be administered through the same or different routes of administration. Co-administration encompasses administration in parallel or sequentially. "Administered concomitantly" refers to the administration of two agents within the same therapeutic time frame; which means, in any manner in which the pharmacological effects of both are manifest in the patient at the same time or during the same time period. Concomitant administration does not require that both agents be administered in a single pharmaceutical composition, in the same dosage form, or by the same route of administration "Complementarity" means the capacity for pairing between nucleobases of a first nucleic acid and a second nucleic acid.

"Contiguous nucleobases" means nucleobases immediately adjacent to each other.

"Coronary heart disease (CHD)" means a narrowing of the small blood vessels that supply blood and oxygen to the heart, which is often a result of atherosclerosis.

"Deoxyribonucleotide" means a nucleotide having a hydrogen at the 2' position of the sugar portion of the nucleotide. Deoxyribonucleotides may be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type 2 diabetes with dyslipidemia" means a condition characterized by Type 2 diabetes, reduced HDL-C, elevated triglycerides, and elevated small, dense LDL particles.

"Diluent" means an ingredient in a composition that lacks pharmacological activity, but is pharmaceutically necessary or desirable. For example, in agents that are injected, the diluent may be a liquid, e.g. saline solution.

"Dose" means a specified quantity of a RBP4-specific modulator or agent provided in a single administration. In certain embodiments, a dose may be administered in two or more boluses, tablets, or injections, as described herein. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in a subject.

"Dyslipidemia" refers to a disorder of lipid and/or lipoprotein metabolism, including lipid and/or lipoprotein overproduction or deficiency. Dyslipidemias may be manifested by elevation of lipids such as cholesterol and triglycerides as well as lipoproteins such as low-density lipoprotein (LDL) cholesterol.

"Effective amount" in the context of modulating an activity or of treating or preventing a condition means the administration of that amount of active ingredient to a subject in need of such modulation, treatment or prophylaxis, either in a single dose or as part of a series, that is effective for modulation of that effect, or for treatment or prophylaxis or improvement of that condition. The effective amount will vary depending upon the health and physical condition of the subject to be treated, the taxonomic group of subjects to be treated, the formulation of the composition, the assessment of the medical situation, and other relevant factors.

"Elevated apoB-levels" means a subject who has been identified as having apoB levels near or above the level at which therapeutic intervention is recommended, according to guidelines recognized by medical professionals. Such a subject may also be considered "in need of treatment" to decrease apoB levels.

"Elevated cholesterol" means total cholesterol at a concentration in a subject at which lipid-lowering therapy is recommended, and includes, without limitation, elevated LDL-C", "elevated VLDL-C," "elevated IDL-C" and "elevated non-HDL-C." In certain embodiments, total cholesterol concentrations of less than 200 mg/dL, 200-239 mg/dL, and greater than 240 mg/dL are considered desirable, borderline high, and high, respectively. In certain embodiments, LDL-C concentrations of 100 mg/dL, 100-129 mg/dL, 130-159 mg/dL, 160-189 mg/dL, and greater than 190 mg/dL are considered optimal, near optimal/above optimal, borderline high, high, and very high, respectively.

"Elevated lipoprotein" means a concentration of lipoprotein in a subject at which lipid-lowering therapy is recommended.

"Elevated triglyceride" means a concentration of triglyceride in the blood or liver at which lipid-lowering therapy is recommended, and includes "elevated triglyceride" and "elevated liver triglyceride." In certain embodiments, triglyceride concentration of 150-199 mg/dL, 200-499 mg/dL, and greater than or equal to 500 mg/dL is considered borderline high, high, and very high, respectively.

"Fully complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" refers to a chimeric oligomeric compound comprising a central region ("gap") and a region on either side of the central region (the "wings"), wherein, the gap comprises at least one modification that is different from that of each wing. Such modifications include nucleobase, monomeric linkage, and sugar modifications, as well as the absence of modification (unmodified). The gap region generally supports RNaseH cleavage.

"Gap-widened" means an antisense compound having a gap segment of 12 or more contiguous 2'-deoxyribonucleotides positioned between 5' and 3' wing segments having from one to six nucleotides having modified sugar moieties.

"Glucose" is a monosaccharide used by cells as a source of energy and metabolic intermediate. "Plasma glucose" refers to glucose present in the plasma.

"High density lipoprotein-C (HDL-C)" means cholesterol associated with high density lipoprotein particles. Concentration of HDL-C in serum (or plasma) is typically quantified in mg/dL or nmol/L. "HDL-C" and "plasma HDL-C" mean HDL-C in serum and plasma, respectively.

"HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

"Hybridization" means the annealing of complementary nucleic acid molecules. In certain embodiments, complementary nucleic acid molecules include, but are not limited to, an antisense compound and a nucleic acid target. In certain such embodiments, complementary nucleic acid molecules include, but are not limited to, an antisense oligonucleotide and a nucleic acid target.

"Hypercholesterolemia" means a condition characterized by elevated cholesterol or circulating(plasma) cholesterol, LDL-cholesterol and VLDL-cholesterol, as per the guidelines of the Expert Panel Report of the National Cholesterol Educational Program (NCEP) of Detection, Evaluation of Treatment of high cholesterol in adults (see, Arch. Int. Med. (1988) 148, 36-39).

"Hyperlipidemia" or "hyperlipemia" is a condition characterized by elevated lipids or circulating(plasma) lipids. This condition manifests an abnormally high concentration of fats. The lipid fractions in the circulating blood are total cholesterol, low density lipoproteins, very low density lipoproteins and triglycerides.

"Hypertriglyceridemia" means a condition characterized by elevated triglyceride or circulating (plasma) triglyceride levels.

"Identifying" or "selecting a subject having a metabolic or cardiovascular disease" means identifying or selecting a subject having been diagnosed with a metabolic disease, a cardiovascular disease, or a metabolic syndrome; or, identifying or selecting a subject having any symptom of a metabolic disease, cardiovascular disease, or metabolic syndrome including, but not limited to, hypercholesterolemia, hyperglycemia, hyperlipidemia, hypertriglyceridemia, hypertension increased insulin resistance, decreased insulin sensitivity, above normal body weight, and/or above normal body fat content or any combination thereof. Such identification may be accomplished by any method, including but not limited to, standard clinical tests or assessments, such as measuring serum or circulating (plasma) cholesterol, measuring serum or circulating (plasma) blood-glucose, measuring serum or circulating (plasma) triglycerides, measuring blood-pressure, measuring body fat content, measuring body weight, and the like.

"Identifying" or "selecting a diabetic subject" means identifying or selecting a subject having been identified as diabetic or identifying or selecting a subject having any symptom of diabetes (type 1 or type 2) such as, but not limited to, having a fasting glucose of at least 110 mg/dL, glycosuria, polyuria, polydipsia, increased insulin resistance, and/or decreased insulin sensitivity.

"Identifying" or "selecting an obese subject" means identifying or selecting a subject having been diagnosed as obese or identifying or selecting a subject with a BMI over 30 and/or a waist circumference of greater than 102 cm in men or greater than 88 cm in women.

"Identifying" or "selecting a subject having dyslipidemia" means identifying or selecting a subject diagnosed with a disorder of lipid and/or lipoprotein metabolism, including lipid and/or lipoprotein overproduction or deficiency. Dyslipidemias may be manifested by elevation of lipids such as cholesterol and triglycerides as well as lipoproteins such as low-density lipoprotein (LDL) cholesterol.

"Identifying" or "selecting" a subject having increased adiposity" means identifying or selecting a subject having an increased amount of body fat (or adiposity) that includes concern for one or both the distribution of fat throughout the body and the size and mass of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese.

"Improved cardiovascular outcome" means a reduction in the occurrence of adverse cardiovascular events, or the risk thereof. Examples of adverse cardiovascular events include, without limitation, death, reinfarction, stroke, cardiogenic shock, pulmonary edema, cardiac arrest, and atrial dysrhythmia.

"Individual" or "subject" or "animal" means a human or non-human animal selected for treatment or therapy.

"Inhibiting the expression or activity" refers to a reduction or blockade of the expression or activity and does not necessarily indicate a total elimination of expression or activity.

"Insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Intermediate low density lipoprotein-cholesterol (IDL-C)" means cholesterol associated with intermediate density lipoprotein. Concentration of IDL-C in serum (or plasma) is typically quantified in mg/mL or nmol/L. "IDL-C" and "plasma IDL-C" mean IDL-C in the serum or plasma, respectively.

"Internucleoside linkage" means a covalent linkage between adjacent nucleosides.

"Intravenous administration" means administration into a vein.

"Linked nucleosides" means adjacent nucleosides which are bonded together.

"Lipid-lowering" means a reduction in one or more lipids in a subject. Lipid-lowering can occur with one or more doses over time.

"Lipid-lowering agent" means an agent; for example, a RBP4-specific modulator; provided to a subject to achieve a lowering of lipids in the subject. For example, in certain embodiments, a lipid-lowering agent is provided to a subject to reduce one or more of ApoB, LDL-C, total cholesterol, and triglycerides.

"Lipid-lowering therapy" means a therapeutic regimen provided to a subject to reduce one or more lipids in a subject. In certain embodiments, a lipid-lowering therapy is provided to reduce one or more of ApoB, total cholesterol, LDL-C, VLDL-C, IDL-C, non-HDL-C, triglycerides, small dense LDL particles, and Lp(a) in a subject.

"Lipoprotein", such as VLDL, LDL and HDL, refers to a group of proteins found in the serum, plasma and lymph and are important for lipid transport. The chemical composition of each lipoprotein differs in that the HDL has a higher proportion of protein versus lipid, whereas the VLDL has a lower proportion of protein versus lipid.

"Low density lipoprotein-cholesterol (LDL-C)" means cholesterol carried in low density lipoprotein particles. Concentration of LDL-C in serum or plasma is typically quantified in mg/dL or nmol/L. "serum LDL-C" and "plasma LDL-C" mean LDL-C in the serum and plasma, respectively.

"Low HDL-C" means a concentration of HDL-C in a subject at which lipid-lowering therapy to increase HDL-C is recommended. In certain embodiments, lipid-lowering therapy is recommended when low HDL-C is accompanied by elevations in non-HDL-C and/or elevations in triglyceride. In certain embodiments, HDL-C concentrations of less than 40 mg/dL are considered low. In certain embodiments, HDL-C concentrations of less than 50 mg/dL are considered low.

"Major risk factors" refers to factors that contribute to a high risk for a particular disease or condition. In certain embodiments, major risk factors for coronary heart disease include, without limitation, cigarette smoking, hypertension, low HDL-C, family history of coronary heart disease, age, and other factors disclosed herein.

"Metabolic disorder" or "metabolic disease" refers to a condition characterized by an alteration or disturbance in metabolic function. "Metabolic" and "metabolism" are terms well known in the art and generally include the whole range of biochemical processes that occur within a living organism. Metabolic disorders include, but are not limited to, hyperglycemia, prediabetes, diabetes (type I and type 2), obesity, insulin resistance, metabolic syndrome and dyslipidemia due to type 2 diabetes.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" refers to a non-complementary nucleobase within a complementary oligomeric compound.

"Mixed dyslipidemia" means a condition characterized by elevated cholesterol and elevated triglycerides.

"Modified internucleoside linkage" means substitution and/or any change from a naturally occurring internucleoside linkage.

"Modified nucleobase" means any nucleobase other than adenine, cytosine, guanine, thymidine, or uracil. An "unmodified nucleobase" means the purine bases, adenine (A) and guanine (G), and the pyrimidine bases, thymine (T), cytosine (C) and uracil (U).

"Modified nucleoside" means a nucleoside having, independently, a modified sugar moiety or modified nucleobase.

"Modified nucleotide" means a nucleotide having, independently, a modified sugar moiety, modified internucleoside linkage, or modified nucleobase.

"Modified sugar" means substitution and/or any change from a natural sugar moiety.

"Modified oligonucleotide" means an oligonucleotide comprising a modification such as a modified internucleoside linkage, a modified sugar, and/or a modified nucleobase.

"Motif" means the pattern of unmodified and modified nucleosides in an antisense compound.

"MTP inhibitor" means an agent inhibits the enzyme, microsomal triglyceride transfer protein.

"Naturally occurring internucleoside linkage" means a 3' to 5' phosphodiester linkage.

"Natural sugar moiety" means a sugar moiety found in DNA (2'-H) or RNA (2'-OH).

"Non-alcoholic fatty liver disease" or "NAFLD" means a condition characterized by fatty inflammation of the liver that is not due to excessive alcohol use (for example, alcohol consumption of over 20 g/day). In certain embodiments, NAFLD is related to insulin resistance and the metabolic syndrome. NAFLD encompasses a disease spectrum ranging from simple triglyceride accumulation in hepatocytes (hepatic steatosis) to hepatic steatosis with inflammation (steatohepatitis), fibrosis, and cirrhosis.

"Nonalcoholic steatohepatitis (NASH)" occurs from progression of NAFLD beyond deposition of triglycerides. A second-hit capable of inducing necrosis, inflammation, and fibrosis is required for development of NASH. Candidates for the second-hit can be grouped into broad categories: factors causing an increase in oxidative stress and factors promoting expression of proinflammatory cytokines. It has been suggested that increased liver triglycerides lead to increased oxidative stress in hepatocytes of animals and humans, indicating a potential cause-and-effect relationship between hepatic triglyceride accumulation, oxidative stress, and the progression of hepatic steatosis to NASH (Browning and Horton, J. Clin. Invest., 2004, 114, 147-152). Hypertriglyceridemia and hyperfattyacidemia can cause triglyceride accumulation in peripheral tissues (Shimamura et al., Biochem. Biophys. Res. Commun., 2004, 322, 1080-1085). In some embodiments, as described herein, the steatosis is steatohepatitis. In some embodiments, as described herein, the steatosis is NASH.

"Non-complementary nucleobase" refers to a pair of nucleobases that do not form hydrogen bonds with one another or otherwise support hybridization.

"Non-familial hypercholesterolemia" means a condition characterized by elevated cholesterol that is not the result of a single gene mutation.

"Non-high density lipoprotein-cholesterol (Non-HDL-C)" means cholesterol associated with lipoproteins other than high density lipoproteins, and includes, without limitation, LDL-C, VLDL-C, and IDL-C.

"Non-specific RBP4 modulator" or "additional therapy" means an agent that can be administered in combination with a RBP4-specific modulator or inhibitor. In some instances, an additional therapy can be a cholesterol-lowering agent and/or glucose-lowering agent and/or a lipid-lowering agent and/or fat/adipose tissue mass-lowering agent.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleoside" means a nucleobase linked to a sugar.

As used herein the term "nucleoside mimetic" is intended to include those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units.

The term "nucleotide mimetic" is intended to include those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Nucleobase sequence" means the order of contiguous nucleobases independent of any sugar, linkage, and/or nucleobase modification.

"Nucleotide" means a nucleoside having a phosphate group covalently linked to the sugar portion of the nucleoside.

"Oligomeric compound" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleoside" means an oligonucleotide in which the internucleoside linkages do not contain a phosphorus atom.

"Oligonucleotide" refers to an oligomeric compound comprising a plurality of linked nucleotides. In certain embodiment, one or more nucleotides of an oligonucleotide is modified. In certain embodiments, an oligonucleotide contains ribonucleic acid (RNA) or deoxyribonucleic acid (DNA). In certain embodiments, oligonucleotides are composed of naturally- and/or non-naturally-occurring nucleobases, sugars and covalent internucleotide linkages, and may further include non-nucleic acid conjugates.

"Parenteral administration" means administration through injection or infusion. Parenteral administration includes, but is not limited to, subcutaneous administration, intravenous administration, or intramuscular administration.

"Peptide" means a molecule formed by linking at least two amino acids by amide bonds. Without limitation, as used herein, "peptide" refers to polypeptides and proteins.

"Pharmaceutical agent" means a substance that provides a therapeutic benefit when administered to an individual. For example, in certain embodiments, an antisense oligonucleotide targeted to RBP4 is pharmaceutical agent.

"Pharmaceutical composition" means a mixture of substances suitable for administering to a subject. For example, a pharmaceutical composition may comprise an agent, for example a RBP4-specific modulator like an antisense oligonucleotide; and a sterile aqueous solution.

"Pharmaceutically acceptable carrier" means a medium or diluent that does not interfere with the structure of the oligonucleotide. Certain such carriers enable pharmaceutical compositions to be formulated as, for example, tablets, pills, dragees, capsules, liquids, gels, syrups, slurries, suspension and lozenges for the oral ingestion by a subject.

"Polygenic hypercholesterolemia" means a condition characterized by elevated cholesterol that results from the influence of a variety of genetic factors. In certain embodiments, polygenic hypercholesterolemia may be exacerbated by dietary intake of lipids.

"Phosphorothioate internucleoside linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a target nucleic acid. In certain embodiments, a portion is a defined number of contiguous nucleobases of a target nucleic acid. In certain embodiments, a portion is a defined number of contiguous nucleobases of an antisense compound.

"Prevention" or "preventing" refers to delaying or forestalling the onset or development of a condition or disease for a period of time from hours to days, preferably weeks to months.

"Prodrug" means a therapeutic agent that is prepared in an inactive or less active form that is converted to an active or more active form (i.e., drug) within the body or cells thereof by the action of endogenous enzymes or other chemicals and/or conditions. In certain embodiments, a shortened oligonucleotide or oligonucleotide metabolite may be more active than it's parent (e.g. 20mer) oligonucleotide.

"RBP4" means any nucleic acid encoding RBP4 mRNA or RBP4 protein. An exemplary RBP4 includes RBP4 having the amino acid sequence encoded by a nucleic acid sequence, e.g. SEQ ID NO: 1. For example, in certain embodiments, a RBP4 nucleic acid includes, without limitation, a DNA sequence encoding RBP4, an RNA sequence transcribed from DNA encoding RBP4, and an mRNA sequence encoding RBP4. "RBP4 mRNA" means an mRNA encoding a RBP4 protein.

"RBP4 specific-inhibitor" or "RBP4 inhibitor" refers to an agent that inhibits, reduces, impairs or decreases the expression, activity or processing of RBP4. A RBP4-specific inhibitor can also refer to an agent that inhibits the differentiation potential or proliferation of a RBP4-expressing cell directly or indirectly. A RBP4-specific inhibitor can also refer to any agent that inhibits targets up-stream or downstream of RBP4 resulting in the inhibition of RBP4 expression. For example, a RBP4 specific-inhibitor can include, but is not limited to, proteins, peptides, polypeptides, antibodies, antisense compounds, including oligonucleotides and antisense oligonucleotides, ssRNA, dsRNA molecules, ribozymes, triple helix molecules, siRNA and other RNAi compounds, and small molecule modulators. The antisense compounds included herein, can operate by an RNaseH or RNAi mechanism or by other known mechanism, such as splicing. A RBP4-specific modulator can be a RBP4-specific inhibitor.

"RBP4-specific modulator" as used herein, refers to an agent that modulates the expression, activity, or processing of RBP4. A RBP4-specific modulator can also refer to an agent that modulates the differentiation potential or proliferation of a RBP4-expressing cell. A RBP4-specific modulator can also refer to any agent that modulates targets up-stream or down-stream of RBP4 resulting in the modulation of RBP4 expression. For example, a RBP4-specific modulator can include, but is not limited to proteins, peptides, polypeptides, antibodies, antisense compounds, including oligonucleotides and antisense oligonucleotides, ssRNA, dsRNA molecules, ribozymes, triple helix molecules, siRNA and other RNAi compounds and small molecule modulators. The antisense compounds included herein, can operate by an RNaseH or RNAi mechanism or by other known mechanism, such as splicing. As used herein, RBP4-specific modulator also can provide a therapeutic benefit when administered to a subject.

"Ribonucleotide" means a nucleotide having a hydroxy at the 2' position of the sugar portion of the nucleotide. Ribonucleotides may be modified with any of a variety of substituents.

"Ribozymes" refers to enzymatic RNA molecules capable of self-catalyzing the specific cleavage of RNA.

"Single-stranded oligonucleotide" means an oligonucleotide which is not hybridized to a complementary strand.

"Statin" means an agent that inhibits the activity of HMG-CoA reductase.

"Statin-intolerant subject" means a subject who, as a result of statin therapy, experiences one or more symptoms, such as, creatine kinase increases, liver function test abnormalities, muscle aches, or central nervous system side effects.

"Subcutaneous administration" means administration just below the skin.

"Subject" means a human or non-human animal selected for treatment or therapy.

"Target" refers to a molecule, the modulation of which is desired.

"Target gene" or "target nucleic acid" refers to a gene or nucleic acid encoding a target molecule.

"Targeting" or "targeted to" refers to the association of an antisense compound to a particular target nucleic acid molecule or a particular region of nucleobases within a target nucleic acid molecule to induce a desired effect. In certain embodiments, "targeted" means having a nucleobase sequence that will allow hybridization of an antisense compound to a target nucleic acid to induce a desired effect. In certain embodiments, a desired effect is reduction of a target nucleic acid or target molecule. In certain such embodiments, a desired effect is reduction of RBP4, including RBP4 mRNA or RBP4 protein.

"Target nucleic acid," "target RNA," "target RNA transcript" and "nucleic acid target" all mean any nucleic acid capable of being targeted by an antisense compound.

"Target region," refers to a portion of a target nucleic acid to which one or more antisense compounds is targeted.

"Target segment" refers to a smaller or sub-portion of a region within a target nucleic acid.

"Therapeutically effective amount" refers to an amount of an agent that provides therapeutic benefit to an animal.

"Therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

"Triglyceride" means a lipid or neutral fat consisting of glycerol combined with three fatty acid molecules.

"Type 2 diabetes," (also known as "type 2 diabetes mellitus" or "diabetes mellitus, type 2", and formerly called "diabetes mellitus type 2", "non-insulin-dependent diabetes (NIDDM)", "obesity related diabetes", or "adult-onset diabetes") is a metabolic disorder that is primarily characterized by insulin resistance, relative insulin deficiency, and hyperglycemia.

"Very low density lipoprotein-cholesterol (VLDL-C)" means cholesterol associated with very low density lipoprotein particles. Concentration of VLDL-C in serum (or plasma) is typically quantified in mg/dL or nmol/L. "serum VLDL-C" and "plasma VLDL-C" mean VLDL-C in the serum or plasma, respectively.

Certain Embodiments

Retinol binding protein (RBP4) is a transporter protein for retinol. The present invention relates generally to treatment of diseases associated with lipid and/or fat and/or glucose dysregulation. Significantly, as presented herein, treatment with RBP4 specific-inhibitors reduces plasma cholesterol and plasma triglycerides in vivo. This finding is bolstered by a concomitant reduction in fatty acid synthesis, increased fatty acid oxidation, white adipose tissue (WAT) weight or mass and changes in gene expression related to cholesterol metabolism. Additionally, white adipose tissue (WAT) weight or mass was reduced by treatment with a RBP4-specific inhibitor.

It is therefore an objective herein to treat dyslipidemia and obesity. As described herein, lipid deregulation and obesity are significant factors associated with metabolic and/or cardiovascular disease. As such, it is an objective herein to treat metabolic and cardiovascular diseases, having as a component lipid dysregulation and/or obesity, by administering a RBP4-specific modulator.

As identified herein, treatment with a RBP4-specific inhibitor also reduces plasma glucose levels and increases insulin sensitivity. This finding is confirmed by a concomitant reduction in gluconeogenesis as further indicated by expression levels of key gluconeogenic genes.

It is therefore also an objective herein to treat metabolic and/or cardiovascular diseases that have as a component or are characterized by combined lipid and glucose dysregulation and/or insulin resistance.

Another significant finding provided herein is improved hepatic insulin sensitivity achieved by administering a RBP4-specific inhibitor. Reducing RBP4 by a RBP4-specific inhibitor, particularly an antisense oligonucleotide results in the benefit of improved hepatic insulin sensitivity It is therefore an objective herein to treat hepatic insulin resistance or disease characterized by hepatic insulin resistance and/or hepatic lipid content such as NAFLD and NASH. Also, because NAFLD associated hepatic insulin resistance is a major factor contributing to hyperglycemia in Type 2 diabetes; it is a specific objective herein to treat type 2 diabetes and/or type 2 diabetes with dyslipidemia with a RBP4-specific inhibitor such as, for example, an antisense oligonucleotide targeting RBP4.

Another significant finding provided herein is lowered free fatty acids in plasma achieved by administering a RBP4-specific inhibitor.

The RBP4-specific inhibition with an antisense oligonucleotide reduced RBP4 mRNA and protein levels including specifically in both adipose tissue and liver tissue. Thus, antisense oligonucleotide inhibitors of RBP4 are useful agents for the treatment of disorders characterized by RBP4 expression in adipose (such as adipogenesis and obesity) and liver tissues (such as hepatic steatosis, NAFLD and NASH). Additionally, unlike other RBP4-specific inhibitors, specifically small molecule inhibitors, the added benefit of using antisense compounds for example, antisense oligonucleotide inhibitors of RBP4 includes the ability to target both adipose and liver tissues simultaneously, both of which play key roles in metabolic disorders like obesity and diabetes.

The present invention also provides herein, methods of modulating the levels of RBP4 in a cell, or tissue by contacting the cell or tissue with a RBP4 specific modulator. The levels can include but are not limited to RBP4 mRNA levels and RBP4 protein levels. In a certain embodiment the cell or tissue is in an animal. In certain embodiments, the animal or subject is a human. In some aspects, RBP4 levels are reduced. Such reduction can occur in a time-dependent manner or in a dose-dependent manner or both.

Another aspect of the invention provides methods of treating an animal having a disease or disorder comprising administering to said animal a therapeutically effective amount of a RBP4-specific modulator, including, more specifically, wherein the RBP4 specific modulator is a RBP4-specific inhibitor, as described herein. In various aspects, the disease or disorder is a cardiovascular and/or metabolic disease or disorder, as described herein. In particular embodiments, the disease or disorder is characterized by dyslipidemia, including, more specifically hyperlipidemia, including, even more specifically hypercholesterolemia and/or hypertriglyceridemia, as described herein. In particular embodiments, the disease or disorder is atherosclerosis. In another embodiment, the disease or disorder is diabetes, including, more specifically Type 2 diabetes, as described herein. In a further embodiment, the disease or disorder is obesity, as described herein. As many of these diseases and disorders are interrelated and as the RBP4-specific modulators demonstrate therapeutic benefit with regard to such diseases and disorders, it is also an object herein, to treat a combination of the above diseases and disorder by administering a RBP4-specific modulator, as described herein.

In some embodiments, the RBP4-specific modulator is a RBP4-specific inhibitor, as described herein, which reduces lipid accumulation or lipid levels, as described herein. The lipid levels can be cholesterol levels or triglyceride levels or both. In a particular embodiment such inhibitor is useful for treating dyslipidemia or conditions characterized by dyslipidema, as described herein, such as cardiovascular diseases, such as atherosclerosis and coronary heart disease, obesity, lipoma, non-alcoholic fatty liver disease (NAFLD), hyperfattyacidemia, as described herein. The reduction in lipid levels can be in combination with a reduction in glucose levels and/or insulin resistance, as described herein. In a particular embodiment, such inhibitor is useful for treating conditions characterized by both dyslipidemia and glucose dysregulation such as metabolic disorder including diabetes and metabolic syndrome, as described herein.

In other embodiments, the RBP4-specific inhibitor reduces adiposity, lipogenesis, lipogenic genes, adipose tissue mass, body weight and/or body fat, as described herein. In a particular embodiment such inhibitor is useful for treating obesity and/or obesity related diseases and disorders. Such reduction can be in combination with a reduction in glucose levels and/or insulin resistance. In a particular embodiment, such inhibitor is useful for treating metabolic syndrome and other disorders associated with diabesity, as described herein.

In a particular embodiment, the RBP4-specific inhibitor reduces lipid levels, adipocyte size, and glucose levels. In a particular embodiment such inhibitor is useful for treating any number of cardiovascular, metabolic and obesity related diseases and disorders as further provided herein.

In some embodiments, are methods of identifying or selecting a subject having dyslipidemia and administering to the subject a RBP4-specific modulator, as described herein.

In other embodiments, are methods of identifying or selecting a subject having obesity or a condition of localized increase in adipogenesis and administering to the subject a RBP4-specific inhibitor, as described herein.

In another embodiment provided herein, are methods of identifying or selecting a subject having or at risk of having a cardiovascular disorder and administering to the subject a RBP4-specific modulator.

In particular embodiments are methods of identifying or selecting a subject having a metabolic disease characterized by dyslipidemia or a change in fat accumulation and administering to the subject a RBP4-specific modulator, as described herein.

In another embodiment provided herein, are methods of identifying or selecting a subject having elevated cholesterol levels and administering to the subject a RBP4-specific inhibitor, thereby reducing cholesterol levels.

In a particular embodiment provided herein, are methods of identifying or selecting a subject having elevated triglyceride levels and administering to the subject a RBP4-specific inhibitor, thereby reducing triglyceride levels.

In another embodiment provided herein, are methods of identifying or selecting a subject having reduced hepatic insulin sensitivity and administering to the subject a RBP4-specific inhibitor, thereby improving hepatic insulin sensitivity.

Further provided herein are methods for treating or preventing metabolic or cardiovascular disorder in a subject comprising selecting a subject having elevated lipid levels, increased fat accumulation, reduced hepatic insulin sensitivity or a combination thereof; and administering to the subject a RBP4-specific modulator.

The invention also provides methods of preventing or delaying the onset of or reducing the risk-factors for a cardiovascular-related or metabolic-related disease or disorder in an animal comprising administering a therapeutically or prophylactically effective amount of a RBP4-specific modulator. In one aspect, the animal is a human. In other aspects, the metabolic and cardiovascular-related disease or disorder includes, but is not limited to obesity, lipoma, lipomatosis, diabetes (including Type 1 diabetes, Type 2 diabetes and Type 2 diabetes with dyslipidemia), dyslipidemia (including hyperlipidemia, hypertriglyceridemia, and mixed dyslipidemia), non-alcoholic fatty liver disease (NAFLD) (including hepatic steatosis and steatohepatitis), hyperfattyacidemia, metabolic syndrome, hyperglycemia, insulin resistance, hypercholesterolemia (including polygenic hypercholesterolemia), coronary heart disease (early onset coronary heart disease), elevated ApoB, or elevated cholesterol (including elevated LDL-cholesterol, elevated VLDL-cholesterol, elevated IDL-cholesterol, and elevated non-HDL cholesterol).

Methods of administration of the RBP4-specific modulators of the invention to a subject are intravenously, subcutaneously, or orally. Administrations can be repeated.

In a further embodiment, the RBP4-specific modulator is a RBP4-specific inhibitor, for example an antisense compound targeted to a nucleic acid encoding RBP4 to inhibit RBP4 mRNA levels or protein expression.

In a further embodiment, the RBP4-specific antisense compound is selected from: an oligonucleotide and antisense oligonucleotide, a ssRNA, a dsRNA, a ribozyme, a triple helix molecule and an siRNA or other RNAi compounds.

In some embodiments, a RBP4-specific modulator can be co-administered with at least one or more additional therapies, as described herein. In related embodiments, the RBP4-specific modulator and additional therapy are administered concomitantly. In a separate embodiment, the RBP4-specific modulator and additional therapy are administered in a single formulation. In some embodiments, the RBP4-specific modulator is administered in combination with one or more of a non-specific modulator of RBP4 or additional therapy that does not modulate RBP4. In some embodiments, the RBP4-specific modulator is administered in combination with a cholesterol-lowering agent and/or glucose-lowering agent and/or a lipid-lowering agent and/or a anti-obesity agent.

The present invention also provides a RBP4-specific modulator as described herein for use in treating or preventing a cardiovascular and/or metabolic disease or disorder as described herein. For example, the invention provides a RBP4-specific modulator as described herein for use in treating or preventing dyslipidemia, atherosclerosis, coronary heart disease, hyperfattyacidemia, or hyperlipoprotenemia, obesity, lipoma, diabetes, atherosclerosis, coronary heart disease, type 2 diabetes, non-alcoholic fatty liver disease (NAFLD), hyperfattyacidemia, or metabolic syndrome.

The present invention also provides the use of a RBP4-specific modulator as described herein in the manufacture of a medicament for treating or preventing a cardiovascular and/or metabolic disease or disorder as described herein. For example, the invention provides the use of a RBP4-specific modulator as described herein in the manufacture of a medicament for treating or preventing dyslipidemia, atherosclerosis, coronary heart disease, hyperfattyacidemia, or hyperlipoprotenemia, obesity, lipoma, diabetes, atherosclerosis, coronary heart disease, type 2 diabetes, non-alcoholic fatty liver disease (NAFLD), hyperfattyacidemia, or metabolic syndrome.

The invention also provides a RBP4-specific modulator as described herein for reducing lipid levels, e.g. for reducing lipid levels in a subject having elevated lipid levels. The present invention also provides the use of a RBP4-specific modulator as described herein in the manufacture of a medicament for reducing lipid levels, e.g. for reducing lipid levels in a subject having elevated lipid levels.

The invention also provides a RBP4-specific modulator as described herein for reducing cholesterol levels, e.g. for reducing cholesterol levels in a subject having elevated cholesterol levels. The present invention also provides the use of a RBP4-specific modulator as described herein in the manufacture of a medicament for reducing cholesterol levels, e.g. for reducing cholesterol levels in a subject having elevated cholesterol levels.

The invention also provides a RBP4-specific modulator as described herein for reducing triglyceride levels, e.g. for reducing triglyceride levels in a subject having elevated triglyceride levels. The present invention also provides the use of a RBP4-specific modulator as described herein in the manufacture of a medicament for reducing triglyceride levels, e.g. for reducing triglyceride levels in a subject having elevated triglyceride levels.

The invention also provides a RBP4-specific modulator as described herein for improving hepatic insulin sensitivity, e.g. for improving hepatic insulin sensitivity in a subject having reduced hepatic insulin sensitivity. The present invention also provides the use of a RBP4-specific modulator as described herein in the manufacture of a medicament for improving hepatic insulin sensitivity, e.g. for improving hepatic insulin sensitivity in a subject having reduced hepatic insulin sensitivity.

The invention also provides a RBP4-specific modulator as described herein for reducing adipogenesis, e.g. for reducing adipogenesis in a subject having elevated adipocyte levels. The present invention also provides the use of a RBP4-specific modulator as described herein in the manufacture of a medicament for reducing adipogenesis, e.g. for reducing adipogenesis in a subject having elevated adipocyte levels.

The invention also provides a RBP4-specific modulator as described herein for treating diabetes, e.g. for treating diabetes in a subject having type 2 diabetes with dyslipidemia. The present invention also provides the use of a RBP4-specific modulator as described herein in the manufacture of a medicament for treating diabetes, e.g. for treating diabetes in a subject having type 2 diabetes with dyslipidemia.

The invention also provides a RBP4-specific modulator as described herein for treating metabolic syndrome, e.g. for treating metabolic syndrome in a subject having metabolic syndrome or one or more risk factors of metabolic syndrome. The present invention also provides the use of a RBP4-specific modulator as described herein in the manufacture of a medicament for treating metabolic syndrome, e.g. for treating metabolic syndrome in a subject having metabolic syndrome or one or more risk factors of metabolic syndrome.

The invention also provides a RBP4-specific modulator as described herein for use in treating or preventing a cardiovascular and/or metabolic disease or disorder as described herein by combination therapy with an additional therapy as described herein.

The invention also provides a pharmaceutical composition comprising a RBP4-specific modulator as described herein in combination with an additional therapy as described herein.

The invention also provides the use of a RBP4-specific modulator as described herein in the manufacture of a medicament for treating or preventing a cardiovascular and/or metabolic disease or disorder as described herein by combination therapy with an additional therapy as described herein.

The invention also provides the use of a RBP4-specific modulator as described herein in the manufacture of a medicament for treating or preventing a cardiovascular and/or metabolic disease or disorder as described herein in a patient who has previously been administered an additional therapy as described herein.

The invention also provides the use of a RBP4-specific modulator as described herein in the manufacture of a medicament for treating or preventing a cardiovascular and/or metabolic disease or disorder as described herein in a patient who is subsequently to be administered an additional therapy as described herein.

The invention also provides a kit for treating or preventing a cardiovascular and/or metabolic disease or disorder as described herein, said kit comprising:
(i) a RBP4-specific modulator as described herein; and optionally
(2) an additional therapy as described herein.

A kit of the invention may further include instructions for using the kit to treat or prevent a cardiovascular and/or metabolic disease or disorder as described herein by combination therapy as described herein.

The antisense compounds targeting RBP4 may have the nucleobase sequence of any of SEQ ID NOs: 8-83.

In another embodiment, the method comprises identifying or selecting an animal having a metabolic or cardiovascular disease and administering to the animal having a metabolic or cardiovascular disease a therapeutically effective amount of a compound comprising a modified oligonucleotide consisting of 12 to 30 linked nucleosides, wherein the modified oligonucleotide is complementary to human RBP4.

In one such embodiment, the metabolic or cardiovascular disease is obesity, diabetes, atherosclerosis, coronary heart disease, non-alcoholic fatty liver disease (NAFLD), hyperfattyacidemia or metabolic syndrome, or a combination thereof.

In another such embodiment, the administering results in a reduction of lipid levels, including triglyceride levels, cholesterol levels; insulin resistance; glucose levels or a combination thereof.

In another such embodiment, the disease wherein the levels are reduced by 5%, 10%, 20%, 30%, 35%, or 40%.

In one such embodiment, the disease is dyslipidemia.

In another such embodiment, the disease of dyslipidemia is hyperlipidemia.

In yet another such embodiment, the hyperlipidemia is hypercholesterolemia, hypertriglyceridemia, or both hypercholesterolemia and hypertriglyceridemia.

In one such embodiment, the disease of NAFLD is hepatic steatosis or steatohepatitis.

In another such embodiment, the disease the diabetes is type 2 diabetes or type 2 diabetes with dyslipidemia.

In one embodiment, the method results in a reduction of triglyceride levels.

In one such embodiment, the method results in a reduction of triglyceride levels of at least 20, 30, 35, or 40%.

In another embodiment, the method results in a reduction of cholesterol levels.

In one such embodiment, the method results in a reduction of cholesterol levels by at least 10, 20, 30, 35 or 40%.

In another embodiment, the method results in a reduction of glucose levels.

In one such embodiment, the method results in a reduction of glucose levels by at least 5 or 10%.

In another embodiment, the method results in a reduction of body weight.

In one such embodiment, the method results in a reduction of body weight by at least 10 or 15%.

In another embodiment, the method results in a reduction of body fat.

In one such embodiment, the method results in a reduction of body fat by at least 10, 20, 30, or 40%.

In another embodiment, the method results in a reduction of triglyceride levels, cholesterol levels, glucose levels, body weight, fat content, insulin resistance, or any combination thereof, wherein levels are independently reduced by 5%, 10%, or 15%.

In another embodiment, the method comprises identifying or selecting an obese animal and administering to the obese animal a therapeutically effective amount of a RBP4 inhibitor.

In one such embodiment, the method results in a reduction of body fat.

In another such embodiment, the method results in a reduction of body fat by at least 10, 20, 30, or 40%.

In another embodiment, the method comprises identifying or selecting a diabetic animal and administering to the diabetic animal a therapeutically effective amount of a RBP4 inhibitor.

In one such embodiment, the method results in a reduction of glucose levels.

In another such embodiment, the method results in a reduction of glucose level by at least 10 or 15%.

In certain embodiments, RBP4 inhibitors can be antisense oligomeric compounds targeted to transthyretin (TTR), as described herein.

Certain Indications

In certain embodiments, the invention provides methods of treating an individual comprising administering one or more pharmaceutical compositions of the present invention. In certain embodiments, the individual has a metabolic disorder or cardiovascular disorder, as described herein. In certain embodiments, the disorder is dyslipidemia, atherosclerosis, coronary heart disease, hyperfattyacidemia, or hyperlipoprotenemia, obesity, lipoma, diabetes, atherosclerosis, coronary heart disease, type 2 diabetes, non-alcoholic fatty liver disease (NAFLD), hyperfattyacidemia, or metabolic syndrome.

In one embodiment, administration of a therapeutically effective amount of an antisense compound targeted to a RBP4 nucleic acid is accompanied by monitoring plasma glucose, plasma triglycerides, and plasma cholesterol levels in the serum of an individual, to determine an individual's response to administration of the antisense compound. In another embodiment, body weight is monitored. An individual's response to administration of the antisense compound is used by a physician to determine the amount and duration of therapeutic intervention.

In one embodiment, administration of an antisense compound targeted to a RBP4 nucleic acid results in reduction of RBP4 expression by at least 15, 20, 25, 30, 35, 40, 45, 50, 55, 60, 65, 70, 75, 80, 85, 90, 95 or 99%, or a range defined by any two of these values. In one embodiment, administration of an antisense compound targeted to a RBP4 nucleic acid results in a change in plasma glucose, plasma triglycerides, plasma cholesterol, and/or body weight. In some embodiments, administration of a RBP4 antisense compound decreases plasma glucose, plasma triglycerides, plasma cholesterol, and/or body weight by at least 15, 20, 25, 30, 35, 40, 45, or 50%, or a range defined by any two of these values.

In certain embodiments, a pharmaceutical composition comprising an antisense compound targeted to RBP4 is used for the preparation of a medicament for treating a patient suffering or susceptible to a metabolic disorder.

Metabolic Disorders

Conditions associated with and included in metabolic disorders encompass, but are not limited to obesity, lipoma, lipomatosis, diabetes (including Type 1 diabetes, Type 2 diabetes and Type 2 diabetes with dyslipidemia), dyslipidemia (including hyperlipidemia, hypertriglyceridemia, and mixed dyslipidemia), non-alcoholic fatty liver disease (NAFLD) (including hepatic steatosis and steatohepatitis), hyperfattyacidemia, metabolic syndrome, hyperglycemia, and insulin resistance.

Blood sugar regulation is the process by which the levels of blood sugar, primarily glucose, are maintained by the body. Blood sugar levels are regulated by negative feedback in order to keep the body in homeostasis. If the blood glucose level falls glucagon is released. Glucagon is a hormone whose effects on liver cells act to increase blood glucose levels. They convert glycogen storage into glucose, through a process is called glycogenolysis. The glucose is released into the bloodstream, increasing blood sugar levels. When levels of blood sugar rise, whether as a result of glycogen conversion, or from digestion of a meal, insulin is released, and causes the liver to convert more glucose into glycogen (glycogenesis), and forces about ⅔ of body cells to take up glucose from the blood, thus decreasing blood sugar levels. Insulin also provides signals to several other body systems, and is the chief regulatory metabolic control in humans.

Diabetes mellitus type 2 is caused by insulin resistance which, if untreated, results in hyperglycemia. Insulin resistance is the condition in which normal amounts of insulin are inadequate to produce a normal insulin response from fat, muscle and liver cells. Insulin resistance in fat cells reduces the effects of insulin and results in elevated hydrolysis of stored triglycerides in the absence of measures which either increase insulin sensitivity or which provide additional insulin. Increased mobilization of stored lipids in these cells elevates free fatty acids in the blood plasma. Insulin resistance in muscle cells reduces glucose uptake and causes local storage of glucose as glycogen, whereas insulin resistance in liver cells reduces storage of glycogen, making it unavailable for release into the blood when blood insulin levels fall. High plasma levels of insulin and glucose due to insulin resistance often lead to metabolic syndrome and type 2 diabetes, and other related complications.

RBP4-specific inhibitors are shown herein to increase insulin sensitivity, reduce glucose and generally improve diabetic state indicated, for, example, by a reduction in ketogenesis and plasma free fatty acids. These studies support the use of RBP4-specific inhibitors for the treatment of diabetes, metabolic syndrome and other disorders characterized by glucose dysregulation.

Nonalcoholic fatty liver disease (NAFLD) is strongly associated with hepatic insulin resistance in patients with poorly controlled type 2 diabetes mellitus (OB/OB) (Petersen, K. F., et al., 2005, *Diabetes* 54:603-608; Petersen, K. F., et al. 2002, *J Clin Invest* 109:1345-1350; Yki-Jarvinen, H., Helve, E., et al., 1989. *Am J Physiol* 256:E732-739). Modest weight reduction in these subjects has been described to reduce hepatic steatosis and normalize fasting plasma glucose concentrations by decreasing hepatic gluconeogenesis and improving hepatic insulin sensitivity (Petersen, K. F., et al., 2005, *Diabetes* 54:603-608). Furthermore, preventing hepatic steatosis in high-fat fed rodents by either increasing mitochondrial oxidation by knockdown of acetyl-CoA carboxylase (ACC) (Savage, D. B., et al. 2006. *J Clin Invest* 116:817-824.), or decreasing lipid synthesis by decreasing the expression of key lipogenic enzymes mitochondrial acyl-CoA glycerol-sn-3-phosphate transferase 1 (mtGPAT) (Neschen, S., et al. 2005, *Cell Metab* 2:55-65), stearoyl-CoA desaturase-1 (SCD1) (Gutierrez-Juarez, R., et al., 2006. *J Clin Invest* 116:1686-1695) or diacylglycerol acyltransferase-2 (DGAT2) (Choi, C. S., et al. 2007. *J Biol Chem* 282:22678-22688) has been described to prevent hepatic insulin resistance.

Metabolic syndrome is the clustering of lipid and non-lipid cardiovascular risk factors of metabolic origin. It has been closely linked to the generalized metabolic disorder known as insulin resistance. The National Cholesterol Education Program (NCEP) Adult Treatment Panel III (ATPIII) established criteria for diagnosis of metabolic syndrome when three or more of five risk determinants are present. The five risk determinants are abdominal obesity defined as waist circumference of greater than 102 cm for men or greater than 88 cm for women, triglyceride levels greater than or equal to 150 mg/dL, HDL cholesterol levels of less than 40 mg/dL for men and less than 50 mg/dL for women, blood pressure greater than or equal to 130/85 mm Hg and fasting glucose levels greater than or equal to 110 mg/dL. These determinants can be readily measured in clinical practice (JAMA, 2001, 285: 2486-2497).

The World Health Organization definition of metabolic syndrome is diabetes, impaired fasting glucose, impaired glucose tolerance, or insulin resistance (assessed by clamp studies) and at least two of the following criteria: waist-to-hip ratio greater than 0.90 in men or greater than 0.85 in women, triglycerides greater than or equal to 1.7 mmol/l or HDL cholesterol less than 0.9 mmol in men and less then 1.0 mmol in women, blood pressure greater than or equal to 140/90 mmHg, urinary albumin excretion rate greater than 20 .mu.g/min or albumin-to-creatinine ratio greater than or equal to 30 mg/g (Diabetes Care, 2005, 28(9): 2289-2304).

A statement from the American Diabetes Association and the European Association for the Study of Diabetes comments on the construct of metabolic syndrome to denote risk factor clustering. In addition to suggestions for research of the underlying pathophysiology, the recommendations include separately and aggressively treating all cardiovascular disease risk factors (Diabetes Care, 2005, 28(9): 2289-2304).

Significantly, it has been described herein that an increase of insulin sensitivity and decrease in glucose levels as well as a decrease in lipid levels can be achieved through the modulation of RBP4 expression. Therefore, another embodiment is a method of treating metabolic and cardiovascular disease or disorders or risks thereof, with RBP4-specific modulating agents.

Unlike the understanding of the mechanism of fat-induced hepatic insulin resistance, the pathogenesis of increased hepatic gluconeogenesis in ob/ob is less well understood. Gluconeogenesis is a metabolic pathway that results in the generation of glucose from non-carbohydrate carbon substrates such as pyruvate, lactate, glycerol, and glucogenic amino acids. The vast majority of gluconeogenesis takes place in the liver and, to a smaller extent, in the cortex of kidneys, and is triggered by the action of insulin. Gluconeogenesis is a target of therapy for metabolic disorders such as hyperglycemia and type 2 diabetes.

RBP4-specific inhibitors are shown herein to reduce hepatic gluconeogenesis. Accordingly, for therapeutics, a subject, preferably an animal, even more preferably a human, suspected of having a metabolic disorder associated with increased gluconeogenesis, can be treated by modulating the expression of RBP4. A subject is treated by administering a RBP4-specific modulator, preferably a RBP4-specific inhibitor, for example an antisense compounds targeting RBP4.

Treatment with ISIS 403527 significantly enhanced the rate of glucose uptake in both muscle and white adipose tissue ($P<0.05$). Furthermore, treatment with ISIS 403527 dramatically increased heart glucose uptake. For the first time, it can be shown that RBP4 antisense inhibition can dramatically improve glucose uptake in the heart, providing a potential therapeutic for glucose uptake related diseases like diabetic cardiomyopathy. This data also demonstrates an improvement in insulin sensitivity not only in liver but also in peripheral tissues. In addition, ISIS 403527 treatment significantly increased whole body glycolysis (treated: 43 vs. saline: 31 mg/kg/min). ISIS 401724 also promoted increased glucose uptake in the gastrocnemius muscle by 48% (treated: 31 vs. saline: 16 mg/kg/min) and in the heart by 65% (treated: 43 vs. saline: 15 mg/kg/min), indicating that ISIS 403527 not only decrease hepatic glucose production but also increase peripheral tissue glucose uptake.

The results shown herein demonstrate that inhibiting RBP4 expression improves whole body insulin sensitivity and decreases hepatic gluconeogenesis. For the first time, these results indicate that antisense inhibitors of RBP4 are candidate therapeutic agents for the treatment of conditions characterized by elevated hepatic glucose production and decreased peripheral glucose uptake, such as metabolic disorders like Type 2 diabetes. In addition, for the first time, these results indicate improved heart glucose uptake, indicating that antisense inhibitors of RBP4 can be used as agents for treatment of cardiomyopathy, which is commonly seen in patients with type 2 diabetes.

For the methods provided herein, the administration of RBP4-specific modulators herein, include, but are not limited to proteins, peptides, polypeptides, antibodies, antisense compounds including oligonucleotides and antisense oligonucleotides, ssRNA, dsRNA molecules, ribozymes, triple helix molecules, siRNA and other RNAi compounds, and small molecule modulators. The antisense compounds included herein, can operate by an RNaseH or RNAi mechanism or by other known mechanism such as splicing.

Further described herein, are RBP4-specific inhibitors, for example antisense compounds targeting RBP4 that reduce RBP4 mRNA and protein.

Also described herein, are RBP4-specific inhibitors, for example antisense compounds targeting RBP4 that reduce liver RBP4 mRNA.

Also described herein, are RBP4-specific inhibitors, for example antisense compounds targeting RBP4 that reduce white adipose tissue (WAT) RBP4 mRNA.

Included herein, are RBP4-specific inhibitors, for example antisense compounds targeting Transthyretin (TTR) that reduce RBP4 expression.

Included herein, are examples of antisense compounds targeting RBP4 and methods of their use prophylactically, for example, to prevent or delay the progression or development of metabolic disorders such as diabetes or elevated blood glucose levels.

Also included herein, are methods for treating or preventing a metabolic disorder, in a subject, comprising administering one or more RBP4-specific modulators. In certain embodiments, the subject has metabolic disorders or conditions including, but not limited obesity, lipoma, lipomatosis, diabetes (including Type 1 diabetes, Type 2 diabetes and Type 2 diabetes with dyslipidemia), dyslipidemia (including hyperlipidemia, hypertriglyceridemia, and mixed dyslipidemia), non-alcoholic fatty liver disease (NAFLD) (including hepatic steatosis and steatohepatitis), hyperfattyacidemia, metabolic syndrome, hyperglycemia, and insulin resistance.

In one embodiment are methods for decreasing blood glucose levels and/or increasing insulin sensitivity, or alternatively methods for treating type 2 diabetes or metabolic syndrome, by administering to a subject suffering from elevated glucose levels or insulin resistance a therapeutically effective amount of a RBP4-specific modulator. In another embodiment, a method of decreasing blood glucose levels and/or increasing insulin sensitivity comprises selecting a subject in need of a decrease in blood glucose or increase in insulin sensitivity, and administering to the subject a therapeutically effective amount of a RBP4-specific modulator. In a further embodiment, a method of reducing risk of development of type 2 diabetes and metabolic syndrome includes selecting a subject having elevated blood glucose levels or reduced insulin sensitivity and one or more additional indicators risk of development of type 2 diabetes or metabolic syndrome, and administering to the subject a therapeutically effective amount of a RBP4-specific modulator, for example a antisense compound.

In one embodiment, administration of a therapeutically effective amount of a RBP4-specific modulator targeted a RBP4 nucleic acid is accompanied by monitoring of glucose levels in the serum of a subject, to determine a subject's response to administration of the RBP4-specific modulator. A subject's response to administration of the RBP4-specific modulator is used by a physician to determine the amount and duration of therapeutic intervention.

In one embodiment, administration of a therapeutically effective amount of an antisense compound targeted a RBP4 nucleic acid is accompanied by monitoring of glucose levels in the serum or insulin sensitivity of a subject, to determine a subject's response to administration of the antisense compound. A subject's response to administration of the antisense compound is used by a physician to determine the amount and duration of therapeutic intervention.

Further described herein, are antisense compounds targeting RBP4 that reduce diet induced obesity in animals. Thus, antisense compounds targeting RBP4 are useful in treating, preventing or delaying obesity.

Further described herein, are antisense compounds targeting RBP4 that reduce white adipose tissue mass or weight in obese animals.

Further described herein, are antisense compounds targeting that reduce plasma insulin in obese animals Further described herein, are antisense compounds targeting RBP4 that reduce plasma glucose in obese animals.

Further described herein, are antisense compounds targeting RBP4 that improve insulin sensitivity.

Further described herein, are antisense compounds targeting RBP4 that reduce fasting plasma insulin concentrations.

Further described herein, are antisense compounds targeting RBP4 that reduce fasting plasma glucose concentrations in obese animals.

Because antisense compounds targeting RBP4 are described herein, to increase insulin sensitivity in normal animals fed a high-fat diet, and to reduce weight gain of these animals, antisense compounds targeting RBP4 is useful in treating, preventing or delaying insulin resistance and weight gain and are therefore useful for the treatment of metabolic disorders such as Type 2 diabetes and obesity.

A physician may determine the need for therapeutic intervention for subjects in cases where more or less aggressive blood glucose or triglyceride-lowering therapy is needed. The practice of the methods herein may be applied to any altered guidelines provided by the NCEP, or other entities that establish guidelines for physicians used in treating any of the diseases or conditions listed herein, for determining coronary heart disease risk and diagnosing metabolic syndrome.

Various RBP4-specific modulators targeting RBP4, such as antisense compounds, can be utilized in pharmaceutical compositions by adding an effective amount of a compound to a suitable pharmaceutically acceptable diluent or carrier. Use of the compounds and methods of the invention may also be useful prophylactically to prevent such diseases or disorders, e.g., to prevent or delay undue weight gain, diabetes, other metabolic disorders, or cardiovascular disorders.

Cardiovascular Disorders

Conditions associated with risk of developing a cardiovascular disorders include, but are not limited to: history of myocardial infarction, unstable angina, stable angina, coronary artery procedures (angioplasty or bypass surgery), evidence of clinically significant myocardial ischemia, noncoronary forms of atherosclerotic disease (peripheral arterial disease, abdominal aortic aneurysm, carotid artery disease), diabetes, cigarette smoking, hypertension, low HDL cholesterol, family history of premature coronary heart disease, obesity, physical inactivity, elevated triglyceride (hypertriglyceridemia), hypercholesterolemia (including polygenic hypercholesterolemia), coronary heart disease (early onset coronary heart disease), elevated ApoB, or elevated cholesterol (including elevated LDL-cholesterol, elevated VLDL-cholesterol, elevated IDL-cholesterol, and elevated non-HDL cholesterol). (Jama, 2001, 285, 2486-2497; Grundy et al., Circulation, 2004, 110, 227-239).

Hypertriglyceridemia (or "hypertriglyceridaemia") denotes high blood levels of triglycerides. A triglyceride is glyceride in which the glycerol is esterified with three fatty acids. Elevated triglyceride levels have been associated with atherosclerosis, even in the absence of hypercholesterolemia (high cholesterol levels). It can also lead to pancreatitis in excessive concentrations. A related term is "hyperglyceridemia" or "hyperglyceridaemia", which refers to a high level of all glycerides, including monoglycerides, diglycerides and triglycerides Triglycerides, as major components of very low density lipoprotein (VLDL) and chylomicrons, play an important role in metabolism as energy sources and transporters of dietary fat. Fat and liver cells can synthesize and store triglycerides. When the body requires fatty acids as an energy source, the hormone glucagon signals the breakdown of the triglycerides by hormone-sensitive lipase to release free fatty acids. The glycerol component of triglycerides can be converted into glucose, via gluconeogenesis, for brain fuel when it is broken down.

Further described herein, are antisense compounds targeting RBP4 that reduce plasma triglycerides in obese animals. The studies show a significant reduction in plasma triglyceride levels after treatment with the RBP4 antisense oligonucleotides. These studies indicate that inhibition of RBP4 expression can provide therapeutic benefit in subjects having metabolic disorders like obesity and Type 2 Diabetes, with the added benefit of preventing or reducing associated dyslipidemia that can also lead to the risk of cardiovascular disorders characterized by hypercholesterolemia and hypertriglyceridemia. Thus, antisense inhibitors of RBP4 could be candidate therapeutic agents for the treatment of conditions characterized by hypercholesterolemia, and hypertriglyceridemia, or conditions of dyslipidemia associated with NAFLD, Type 2 diabetes, obesity and other metabolic disorders.

Hypercholesterolemia (elevated blood cholesterol) is the presence of high levels of cholesterol in the blood. It is not a disease but a metabolic derangement that can be secondary to many diseases and can contribute to many forms of disease, most notably cardiovascular disease. It is closely related to "hyperlipidemia" (elevated levels of lipids) and "hyperlipoproteinemia" (elevated levels of lipoproteins). Conditions with elevated concentrations of oxidized LDL particles, especially "small dense LDL" (sdLDL) particles, are associated with atheroma formation in the walls of arteries, a condition known as atherosclerosis, which is the principal cause of coronary heart disease and other forms of cardiovascular disease. In contrast, HDL particles (especially large HDL) have been identified as a mechanism by which cholesterol and inflammatory mediators can be removed from atheroma. Increased concentrations of HDL correlate with lower rates of atheroma progressions and even regression.

Elevated levels of the lipoprotein fractions, LDL, IDL and VLDL are regarded as atherogenic (prone to cause atherosclerosis). Levels of these fractions correlate with the extent and progress of atherosclerosis. Conversely, the cholesterol can be within normal limits, yet be made up primarily of small LDL and small HDL particles, under which conditions atheroma growth rates would still be high. In contrast, however, if LDL particle number is low (mostly large particles) and a large percentage of the HDL particles are large, then atheroma growth rates are usually low, even negative, for any given cholesterol concentration.

Further, a RBP4-specific inhibitor may cause a significant reduction in plasma cholesterol levels after treatment with the RBP4 antisense oligonucleotides.

Further provided here in are studies that indicate inhibition of RBP4 expression can provide therapeutic benefit in subjects having metabolic disorders like obesity and Type 2 Diabetes, with the added benefit of preventing or reducing associated dyslipidemia that can also lead to the risk of cardiovascular disorders characterized by hypercholesterolemia and hypertriglyceridemia. Thus, antisense inhibitors of RBP4 could be candidate therapeutic agents for the treatment of conditions characterized by hypercholesterolemia, and hypertriglyceridemia, or conditions of dyslipidemia associated with NAFLD, Type 2 diabetes, obesity and other metabolic disorders.

Elevated blood glucose levels, elevated triglyceride levels or elevated cholesterol levels are considered a risk factor in the development and progression of atherosclerosis. Atherosclerosis is a disease affecting arterial blood vessels. It is a chronic inflammatory response in the walls of arteries, in large part due to the accumulation of macrophage white blood cells and promoted by low density (especially small particle) lipoproteins (plasma proteins that carry cholesterol and triglycerides) without adequate removal of fats and cholesterol from the macrophages by functional high density lipoproteins (HDL), (see apoA-1 Milano). It is commonly referred to as a "hardening" or "furring" of the arteries. It is caused by the formation of multiple plaques within the arteries. Atherosclerosis can lead to coronary heart disease, stroke, peripheral vascular disease, or other cardiovascular-related disorders.

Further described herein, are studies that show RBP4-specific modulators, like antisense compounds, reducing blood glucose levels, elevated triglyceride levels and elevated cholesterol levels. Thus RBP4-specific antisense oligonucleotides could be candidate therapeutic agents for the treatment of conditions characterized by the progression of atherosclerosis.

RBP4-specific inhibitors are shown herein to lower lipid levels, accordingly, for therapeutics, a subject, preferably an animal, even more preferably a human, suspected of having a cardiovascular disorder which can be treated by modulating the expression of RBP4. A subject is treated by administering a RBP4-specific modulator, preferably a RBP4-specific inhibitor, for example an antisense compounds targeting RBP4.

A further embodiment is a method of treating cardiovascular disorders wherein, the RBP4-specific modulator is a RBP4-specific inhibitor, for example a RBP4-specific antisense oligonucleotide.

The administration of RBP4-specific modulators herein, include, but are not limited to proteins, peptides, polypeptides, antibodies, antisense compounds including oligonucleotides and antisense oligonucleotides, ssRNA, dsRNA molecules, ribozymes, triple helix molecules, siRNA and other RNAi compounds, and small molecule modulators. The antisense compounds included herein, can operate by an RNaseH or RNAi mechanism or by other known mechanism such as splicing.

Further described herein, are RBP4-specific inhibitors, for example antisense compounds targeting RBP4 that reduce RBP4 mRNA and protein.

Also described herein, are RBP4-specific inhibitors, for example antisense compounds targeting RBP4 that reduce liver RBP4 mRNA.

Also described herein, are RBP4-specific inhibitors, for example antisense compounds targeting RBP4 that reduce white adipose tissue (WAT) RBP4 mRNA.

Included herein, are RBP4-specific inhibitors, for example antisense compounds targeting Transthyretin (TTR) that reduce RBP4 expression.

Included herein, are examples of antisense compounds targeting RBP4 and methods of their use prophylactically, for example, to prevent or delay the progression or development of cardiovascular disorders such as elevated cholesterol and/or triglyceride levels.

The administration of RBP4-specific modulators herein, include, but are not limited to proteins, peptides, polypeptides, antibodies, antisense compounds including oligonucleotides and antisense oligonucleotides, ssRNA, dsRNA molecules, ribozymes, triple helix molecules, siRNA and other RNAi compounds, and small molecule modulators. The antisense compounds included herein, can operate by an RNaseH or RNAi mechanism or by other known mechanism such as splicing.

Various RBP4-specific modulators targeting RBP4, such as antisense compounds, can be utilized in pharmaceutical compositions by adding an effective amount of a compound to a suitable pharmaceutically acceptable diluent or carrier. Use of the compounds and methods of the invention may also be useful prophylactically to prevent such diseases or disorders, e.g., to prevent or delay undue weight gain, diabetes, other metabolic disorders, or cardiovascular disorders.

In one embodiment, a therapeutically effective amount of a RBP4-specific antisense compound is administered to a subject having atherosclerosis. In a further embodiment a therapeutically effective amount of antisense compound targeted to a RBP4 nucleic acid is administered to a subject susceptible to atherosclerosis. Atherosclerosis is assessed directly through routine imaging techniques such as, for example, ultrasound imaging techniques that reveal carotid intimomedial thickness. Accordingly, treatment and/or prevention of atherosclerosis further include monitoring atherosclerosis through routine imaging techniques. In one embodiment, administration of a RBP4-specific antisense compound leads to a lessening of the severity of atherosclerosis, as indicated by, for example, a reduction of carotid intimomedial thickness in arteries.

In a non-limiting embodiment, measurements of cholesterol, lipoproteins and triglycerides are obtained using serum or plasma collected from a subject. Methods of obtaining serum or plasma samples are routine, as are methods of preparation of the serum samples for analysis of cholesterol, triglycerides, and other serum markers.

A physician may determine the need for therapeutic intervention for subjects in cases where more or less aggressive blood glucose or triglyceride-lowering therapy is needed. The practice of the methods herein may be applied to any altered guidelines provided by the NCEP, or other entities that establish guidelines for physicians used in treating any of the diseases or conditions listed herein, for determining coronary heart disease risk and diagnosing metabolic syndrome.

Further described herein, are antisense compounds targeting RBP4 that reduce triglycerides levels in obese animals. Thus, antisense compounds targeting RBP4 are useful in treating, preventing or delaying cardiovascular disease. These findings are in contrast to a previous study showing a dominant-negative RBP4 decreased expression of hairy and enhancer of 1 (HES-1), a transcriptional repressor of peroxisome proliferator-activated receptor gamma (PPARγ) resulting in increased expression of PPARγ and increased hepatic triglyceride content independent of SREBP (Herzig, S., Hedrick, S., Morantte, I., Koo, S. H., Galimi, F., and Montminy, M. 2003. *Nature* 426:190-193). In this study, there was no increase in the level of PPARγ expression possibly reflecting differences in the models used or the method of knockdown.

Further described herein, are antisense compounds targeting RBP4 that reduce total plasma cholesterol in obese animals. In related embodiment, reduced plasma cholesterol through antisense inhibition of RBP4, is mediated by the upregulation of the rate-limiting step of bile acid synthesis catalyzed by Cyp7A1 leading to increased efflux of hepatic cholesterol into bile salts. Moreover, previous studies have described that glucagon signaling inhibits the transcription of Cyp7A1 in cell culture-based systems of rat and human hepatocytes (Song, K. H., and Chiang, J. Y. 2006, *Hepatology*, 43:117-125; Hylemon, P. B., Gurley, E. C., Stravitz, R. T., Litz, J. S., Pandak, W. M., Chiang, J. Y., and Vlahcevic, Z. R. 1992, *J Biol Chem* 267:16866-16871). Embodiments, as described herein, support a link between glucagon action and bile acid synthesis in rat liver since RBP4 inhibition effectively limits glucagon transcriptional signaling therefore increasing the expression of Cyp7A1 and promoting bile salt efflux.

Further described herein, are antisense compounds targeting RBP4 that reduce hepatic lipid content in obese animals. Also incorporated herein, the reduced hepatic lipid content, includes, but is not limited to, a reduction in lipids such as triglycerides, diacylglycerols, and long chain CoAs.

In another embodiment, antisense compounds targeting RBP4 increase rate of fatty acid oxidation in obese animals.

In another embodiment, antisense compounds targeting RBP4 increase rate of hepatic insulin sensitivity in obese animals. In another embodiment, a RBP4-specific modulator that decreases the hepatic expression of RBP4 mRNA improves hepatic insulin sensitivity associated with fatty liver and hepatic insulin resistance.

In another embodiment, the antisense compounds targeting RBP4 reduce hepatic diacylglcerol (DAG) content in obese animals.

Certain Combination Indications

In certain embodiments, the invention provides methods of treating a subject comprising administering one or more RBP4-specific modulators, as described herein. In certain embodiments, the subject has metabolic and cardiovascular-related disorders or conditions including, but not limited to obesity, lipoma, lipomatosis, diabetes (including Type I diabetes, Type 2 diabetes and Type 2 diabetes with dyslipidemia), dyslipidemia (including hyperlipidemia, hypertriglyceridemia, and mixed dyslipidemia), non-alcoholic fatty liver disease (NAFLD) (including hepatic steatosis and steatohepatitis), hyperfattyacidemia, metabolic syndrome, hyperglycemia, insulin resistance, hypercholesterolemia (including polygenic hypercholesterolemia), coronary heart disease (early onset coronary heart disease), elevated ApoB, or elevated cholesterol (including elevated LDL-cholesterol, elevated VLDL-cholesterol, elevated IDL-cholesterol, and elevated non-HDL cholesterol).

In one embodiment are methods for decreasing blood glucose levels or triglyceride levels, or alternatively methods for treating obesity or metabolic syndrome, by administering to a subject suffering from elevated glucose or triglyceride levels a therapeutically effective amount of a RBP4-specific modulator targeted to a RBP4 nucleic acid. In another embodiment, a method of decreasing blood glucose or triglyceride levels comprises selecting a subject in need of a decrease in blood glucose or triglyceride levels, and administering to the subject a therapeutically effective amount of a RBP4-specific modulator targeted to a RBP4 nucleic acid. In a further embodiment, a method of reducing risk of development of obesity and metabolic syndrome includes selecting a subject having elevated blood glucose or triglyceride levels and one or more additional indicators risk of development of obesity or metabolic syndrome, and administering to the subject a therapeutically effective amount of a RBP4-specific modulator targeted to a RBP4 nucleic acid, for example a antisense compound.

In one embodiment, administration of a therapeutically effective amount of a RBP4-specific modulator targeted a RBP4 nucleic acid is accompanied by monitoring of glucose levels or triglyceride levels in the serum of a subject, to determine a subject's response to administration of the RBP4-specific modulator. A subject's response to administration of the RBP4-specific modulator is used by a physician to determine the amount and duration of therapeutic intervention.

In one embodiment are methods for decreasing blood glucose levels or lipid levels, including cholesterol and triglyceride levels, or alternatively methods for treating metabolic disorders, such as obesity, or metabolic syndrome, or cardiovascular disorders, such as hypertriglyceridemia or hypercholesterolemia, by administering to a subject suffering from elevated glucose or triglyceride levels a therapeutically effective amount of a RBP4-specific antisense compound. In another embodiment, a method of decreasing blood glucose or triglyceride levels comprises selecting a subject in need of a decrease in blood glucose or triglyceride levels, and administering to the subject a therapeutically effective amount of a RBP4-specific antisense compound. In a further embodiment, a method of reducing risk of development of metabolic disorders, such as obesity, or metabolic syndrome, or cardiovascular disorders, such as hypertriglyceridemia or hypercholesterolemia includes selecting a subject having elevated blood glucose or triglyceride levels and one or more additional indicators risk of development of obesity or metabolic syndrome, and administering to the subject a therapeutically effective amount of a RBP4-specific antisense compound.

In one embodiment, administration of a therapeutically effective amount of an antisense compound targeted a RBP4 nucleic acid is accompanied by monitoring of glucose levels or triglyceride levels in the serum of a subject, to determine a subject's response to administration of the antisense compound. A subject's response to administration of the antisense compound is used by a physician to determine the amount and duration of therapeutic intervention.

In certain embodiments, a pharmaceutical composition comprising an antisense compound targeted to RBP4 is for use in therapy, as described herein. In certain embodiments, the therapy is the reduction of blood glucose, triglyceride or liver triglyceride in a subject, as described herein. In certain embodiments, the therapy is the treatment of hypercholesterolemia, mixed dyslipidemia, atherosclerosis, a risk of developing atherosclerosis, coronary heart disease, a history of coronary heart disease, early onset coronary heart disease, one or more risk factors for coronary heart disease, type 2 diabetes, type 2 diabetes with dyslipidemia, dyslipidemia, hypertriglyceridemia, hyperlipidemia, hyperfattyacidemia, hepatic steatosis, non-alcoholic steatohepatitis, or non-alcoholic fatty liver disease. In additional embodiments, the therapy is the reduction of CHD risk. In certain the therapy is prevention of atherosclerosis. In certain embodiments, the therapy is the prevention of coronary heart disease.

In certain embodiments, a pharmaceutical composition comprising an antisense compound targeted to RBP4 is used for the preparation of a medicament for reduction of blood glucose, triglyceride or liver triglyceride, as described herein. In certain embodiments, a pharmaceutical composition comprising an antisense compound targeted to RBP4 is used for the preparation of a medicament for reducing coronary heart disease risk. In certain embodiments, an antisense compound targeted to RBP4 is used for the preparation of a medicament for the treatment of hypercholesterolemia, mixed dyslipidemia, atherosclerosis, a risk of developing atherosclerosis, coronary heart disease, a history of coronary heart disease, early onset coronary heart disease, one or more risk factors for coronary heart disease, type 2 diabetes, type 2 diabetes with dyslipidemia, dyslipidemia, hypertriglyceridemia, hyperlipidemia, hyperfattyacidemia, hepatic steatosis, non-alcoholic steatohepatitis, or non-alcoholic fatty liver disease.

Antisense compounds targeting RBP4, described herein, reduce cholesterol levels in normal animals fed a high-fat diet; more particularly reduce LDL-cholesterol. Thus, antisense compounds targeting RBP4 are useful in treating, preventing or delaying cardiovascular disease.

In one embodiment are methods for decreasing blood glucose and triglyceride levels, or alternatively methods for treating metabolic-related disorders and cardiovascular-related disorders, such as metabolic syndrome and atherosclerosis, by administering to a subject suffering from elevated glucose levels or insulin resistance a therapeutically effective amount of a RBP4-specific modulator. In another embodiment, a method of decreasing blood glucose and triglyceride levels comprises selecting a subject in need of a decrease in blood glucose and triglyceride levels, and administering to the subject a therapeutically effective amount of a RBP4-specific modulator. In a further embodiment, a method of reducing risk of development of metabolic-related disorders and cardiovascular-related disorders, such as metabolic syndrome and atherosclerosis, includes selecting a subject having elevated blood glucose and triglyceride levels and one or more additional indicators risk of development of metabolic-related disorders and cardiovascular-related disorders, and administering to the subject a therapeutically effective amount of a RBP4-specific modulator, for example a antisense compound.

In one embodiment are methods for decreasing blood glucose levels or triglyceride levels, or alternatively methods for treating metabolic disorders, such as obesity or metabolic syndrome, and/or cardiovascular disorders, such as hypertriglyceridemia or hypercholesterolemia, by administering to a subject suffering from elevated glucose or triglyceride levels a therapeutically effective amount of a RBP4-specific antisense compound. In another embodiment, a method of decreasing blood glucose or triglyceride levels comprises selecting a subject in need of a decrease in blood glucose or triglyceride levels, and administering to the subject a therapeutically effective amount of a RBP4-specific antisense compound. In a further embodiment, a method of reducing risk of development of metabolic disorders, such as obesity, or metabolic syndrome, or cardiovascular disorders, such as hypertriglyceridemia or hypercholesterolemia includes selecting a subject having elevated blood glucose or triglyceride levels and one or more additional indicators risk of development of obesity or metabolic syndrome, and administering to the subject a therapeutically effective amount of a RBP4-specific antisense compound.

In one embodiment, an antisense compound targeting RBP4 modulates RBP4 expression, processing or activity, wherein, that reduction of RBP4 expression in lowers plasma triglyceride and cholesterol concentrations in an OB/OB animal and protects against fat induced hepatic steatosis and hepatic insulin resistance. In a further embodiment, since OB/OB is often associated with hyperlipidemia and hypercholesterolemia in addition to hepatic insulin resistance, RBP4 reduces or treats OB/OB.

In one embodiment, administration of a therapeutically effective amount of an antisense compound targeted a RBP4 nucleic acid is accompanied by monitoring of glucose levels or triglyceride levels in the serum of a subject, to determine a subject's response to administration of the antisense compound. A subject's response to administration of the antisense compound is used by a physician to determine the amount and duration of therapeutic intervention.

Assays

Assays for certain metabolic and cardiovascular disease markers are known and understood by those of skill in the art to be useful for assessing the therapeutic effect of a pharmaceutical agent. Such markers include, but are not limited to, glucose, lipids, particularly cholesterol and triglycerides, lipoproteins such as LDL and HDL, proteins such as glycosolated hemoglobin, and other relevant cellular products.

Preferably, the cells within said fluids, tissues or organs being analyzed contain a nucleic acid molecule encoding RBP4 protein and/or the RBP4 protein itself. Samples of organs or tissues may be obtained through routine clinical biopsy. Samples of bodily fluid such as blood or urine are routinely and easily tested. For example blood glucose levels can be determined by a physician or even by the patient using a commonly available test kit or glucometer (for example, the Ascensia ELITE™ kit, Ascensia (Bayer), Tarrytown N.Y., or Accucheck, Roche Diagnostics). Alternatively or in addition, glycated hemoglobin (HbA.sub.1c) may be measured. HbA.sub.1c is a stable minor hemoglobin variant formed in vivo via posttranslational modification by glucose, and it contains predominantly glycated NH.sub.2-terminal .beta.-chains. There is a strong correlation between levels of HbA.sub.1c and the average blood glucose levels over the previous 3 months. Thus HbA.sub.1c is often viewed as the "gold standard" for measuring sustained blood glucose control (Bunn, H. F. et al., 1978, Science. 200, 21-7). HbA.sub.1c can be measured by ion-exchange HPLC or immunoassay; home blood collection and mailing kits for HbA.sub.1c measurement are now widely available. Serum fructosamine is another measure of stable glucose control and can be measured by a calorimetric method (Cobas Integra, Roche Diagnostics).

RBP4-Specific Modulators

The modulator agents included herein, will suitably affect, modulate or inhibit RBP4 expression. Suitable agents for reducing or modulating gene expression, processing and activity include, but are not restricted to proteins, peptides, polypeptides, antibodies, antisense compounds including oligonucleotides and antisense oligonucleotides, ssRNA, dsRNA molecules, ribozymes, triple helix molecules, siRNA and other RNAi compounds, and small molecule modulators. The antisense compounds included herein, can operate by an RNaseH or RNAi mechanism or by other known mechanism such as splicing. In a further embodiment, the RBP4-specific modulator is a RBP4-specific inhibitor, for example an antisense compound targeted to RBP4 that function to inhibit the translation, for example, of RBP4- or RBP4-encoding mRNA.

For example, in one non-limiting embodiment, the methods comprise the step of administering to a subject a therapeutically effective amount of a RBP4-specific inhibitor. RBP4-specific inhibitors, as presented herein, effectively inhibit the activity and/or expression of RBP4. In one embodiment, the activity or expression of RBP4 in a subject is inhibited by about 10%. Preferably, the activity or expression of RBP4 in a subject is inhibited by about 30%. More preferably, the activity or expression of RBP4 in a subject is inhibited by 50% or more. Thus, the RBP4-specific modulators, for example oligomeric antisense compounds, modulate expression of RBP4 mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

Accordingly, another embodiment herein provides methods for modulating RBP4 expression, activity, and processing comprising contacting a RBP4 cell with a RBP4-specific modulator, which can also be RBP4-specific inhibitor. Representative RBP4-specific modulators include, but are not limited to proteins, peptides, polypeptides, antibodies, antisense compounds including oligonucleotides and antisense oligonucleotides, ssRNA, dsRNA molecules, ribozymes, triple helix molecules, siRNA and other RNAi compounds, and small molecule modulators. The antisense compounds included herein, can operate by an RNaseH or RNAi mechanism or by other known mechanism such as splicing.

Ribozymes

Ribozyme molecules designed to catalytically cleave RBP4 mRNA transcripts can also be used to prevent translation of RBP4 mRNAs and expression of RBP4 proteins For example, hammerhead ribozymes that cleave mRNAs at locations dictated by flanking regions that form complementary base pairs with the target mRNA might be used so long as the target mRNA has the following common sequence: 5'-UG-3'. See, e.g., Haseloff and Gerlach (1988) Nature 334:585-591. As another example, hairpin and hepatitis delta virus ribozymes may also be used. See, e.g., Bartolome et al. (2004) Minerva Med. 95(1):11-24. To increase efficiency and minimize the intracellular accumulation of non-functional mRNA transcripts, a ribozyme should be engineered so that the cleavage recognition site is located near the 5' end of the target RBP4 mRNA. Ribozymes within the invention can be delivered to a cell using any of the methods, as described herein.

Other methods can also be used to reduce RBP4 gene expression in a cell. For example, RBP4 gene expression can be reduced by inactivating or "knocking out" the RBP4 gene or its promoter using targeted homologous recombination. See, e.g., Kempin et al., Nature 389: 802 (1997); Smithies et al. (1985) Nature 317:230-234; Thomas and Capecchi (1987) Cell 51:503-512; and Thompson et al. (1989) Cell 5:313-321. For example, a mutant, non-functional RBP4 gene variant (or a completely unrelated DNA sequence) flanked by DNA homologous to the endogenous RBP4 gene (either the coding regions or regulatory regions of the RBP4 gene) can be used, with or without a selectable marker and/or a negative selectable marker, to transfect cells that express RBP4 protein in vivo.

Triple-Helix Molecule

RBP4 gene expression might also be reduced by targeting deoxyribonucleotide sequences complementary to the regulatory region of the RBP4 gene (i.e., the RBP4 promoter and/or enhancers) to form triple helical structures that prevent transcription of the RBP4 gene in target cells. See generally, Helene, C. (1991) Anticancer Drug Des. 6(6): 569-84; Helene, C., et al. (1992) Ann. N.Y. Acad. Sci. 660:27-36; and Maher, L. J. (1992) Bioassays 14(12): 807-15. Nucleic acid molecules to be used in this technique are preferably single stranded and composed of deoxyribonucleotides. The base composition of these oligonucleotides should be selected to promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, e.g., containing a stretch of G residues. These molecules will form a triple helix with a DNA duplex that is rich in GC pairs, in which the majority of the purine residues are located on a single strand of the targeted duplex, resulting in CGC triplets across the three strands in the triplex. The potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizable stretch of either purines or pyrimidines to be present on one strand of a duplex.

The antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramide chemical synthesis. RNA molecules may be generated by in vitro and in vivo transcription of DNA sequences encoding the antisense RNA molecule. Such DNA sequences may be incorporated into a wide variety of vectors which incorporate suitable RNA polymerase promoters. Alternatively, antisense cDNA constructs that synthesize antisense RNA constitutively or inducibly, depending on the promoter used, can be introduced stably into cell lines.

siRNA/RNAi/dsRNA

The invention comprises RBP4-specific modulators, for example siRNA, RNAi and dsRNA that modulate RBP4 expression, activity, or processing. The use of short-interfering RNA (siRNA) is a technique known in the art for inhibiting expression of a target gene by introducing exogenous RNA into a living cell (Elbashir et al. 2001. Nature. 411:494-498). siRNA suppress gene expression through a highly regulated enzyme-mediated process called RNA interference (RNAi). RNAi involves multiple RNA-protein interactions characterized by four major steps: assembly of siRNA with the RNA-induced silencing complex (RISC), activation of the RISC, target recognition and target cleavage. Therefore, identifying siRNA-specific features likely to contribute to efficient processing at each step is beneficial efficient RNAi. Reynolds et al. provide methods for identifying such features. A. Reynolds et al., "Rational siRNA design for RNA interference", Nature Biotechnology 22(3), March 2004.

In that study, eight characteristics associated with siRNA functionality were identified: low G/C content, a bias towards low internal stability at the sense strand 3'-terminus, lack of inverted repeats, and sense strand base preferences (positions 3, 10, 13 and 19). Further analyses revealed that application of an algorithm incorporating all eight criteria significantly improves potent siRNA selection. siRNA sequences that contain internal repeats or palindromes may form internal foldback structures. These hairpin-like structures may exist in equilibrium with the duplex form, reducing the effective concentration and silencing potential of the siRNA. The relative stability and propensity to form internal hairpins can be estimated by the predicted melting temperatures ($T_M$). Sequences with high $T_M$ values would favor internal hairpin structures.

siRNA can be used either ex vivo or in vivo, making it useful in both research and therapeutic settings. Unlike in other antisense technologies, the RNA used in the siRNA technique has a region with double-stranded structure that is made identical to a portion of the target gene, thus making inhibition sequence-specific. Double-stranded RNA-mediated inhibition has advantages both in the stability of the material to be delivered and the concentration required for effective inhibition.

The extent to which there is loss of function of the target gene can be titrated using the dose of double stranded RNA delivered. A reduction or loss of gene expression in at least 99% of targeted cells has been described. See, e.g., U.S. Pat. No. 6,506,559. Lower doses of injected material and longer times after administration of siRNA may result in inhibition in a smaller fraction of cells. Quantitation of gene expression in a cell show similar amounts of inhibition at the level of accumulation of target mRNA or translation of target protein.

The RNA used in this technique can comprise one or more strands of polymerized ribonucleotides, and modification can be made to the sugar-phosphate backbone as disclosed above. The double-stranded structure is often formed using either a single self-complementary RNA strand (hairpin) or two complementary RNA strands. RNA containing a nucleotide sequences identical to a portion of the target gene is preferred for inhibition, although sequences with insertions, deletions, and single point mutations relative to the target sequence can also be used for inhibition. Sequence identity may be optimized using alignment algorithms known in the art and through calculating the percent difference between the nucleotide sequences. The duplex region of the RNA could also be described in functional terms as a nucleotide sequence that is capable of hybridizing with a portion of the target gene transcript.

There are multiple ways to deliver siRNA to the appropriate target, RBP4. Standard transfection techniques may be used, in which siRNA duplexes are incubated with cells of interest and then processed using standard commercially available kits. Electroporation techniques of transfection may also be appropriate. Cells or organisms can be soaked in a solution of the siRNA, allowing the natural uptake processes of the cells or organism to introduce the siRNA into the system. Viral constructs packaged into a viral particle would both introduce the siRNA into the cell line or organism and also initiate transcription through the expression construct. Other methods known in the art for introducing nucleic acids to cells may also be used, including lipid-mediated carrier transport, chemical-mediated transport, such as calcium phosphate, and the like.

For therapeutic uses, tissue-targeted nanoparticles may serve as a delivery vehicle for siRNA. These nanoparticles carry the siRNA exposed on the surface, which is then available to bind to the target gene to be silenced. Schiffelers, et al., Nucleic Acids Research 2004 32(19):e149. These nanoparticles may be introduced into the cells or organisms using the above described techniques already known in the art. RGD peptides have been described to be effective at targeting the neovasculature that accompanies the growth of tumors. Designing the appropriate nanoparticles for a particular illness is a matter of determining the appropriate targets for the particular disease.

Other delivery vehicles for therapeutic uses in humans include pharmaceutical compositions, intracellular injection, and intravenous introduction into the vascular system. Inhibition of gene expression can be confirmed by using biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression may be assayed using a reporter or drug resistance gene whose protein product can be easily detected and quantified. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

These techniques are well known and easily practiced by those skilled in the art. For in vivo use in humans, reduction or elimination of symptoms of illness will confirm inhibition of the target gene's expression.

Polyclonal and Monoclonal Antibodies

The invention comprises RBP4-specific modulators, for example, polyclonal and monoclonal antibodies that bind to RBP4 polypeptides of the invention and modulate RBP4 expression, activity, or processing. The term "antibody" as used herein, refers to immunoglobulin molecules and immunologically active portions of immunoglobulin molecules, i.e., molecules that contain a binding site that specifically binds to an epitope (antigen, antigenic determinant). An antibody molecule that specifically binds to a polypeptide of the invention is a molecule that binds to an epitope present in said polypeptide or a fragment thereof, but does not substantially bind other molecules in a sample, e.g., a biological sample, which naturally contains the polypeptide. Examples of immunologically active portions of immunoglobulin molecules include F(ab) and F(ab').sub.2 fragments which can be generated by treating the antibody with an enzyme such as pepsin. Polyclonal and/or monoclonal antibodies that specifically bind one form of the gene product but not to the other form of the gene product are also provided. Antibodies are also provided, that bind a portion of either the variant or the reference gene product that contains the polymorphic site or sites. The term "monoclonal antibody" or "monoclonal antibody composition", as used herein, refers to a population of antibody molecules that are directed against a specific epitope and are produced either by a single clone of B cells or a single hybridoma cell line. A monoclonal antibody composition thus typically displays a single binding affinity for a particular polypeptide of the invention with which it immunoreacts.

Polyclonal antibodies can be prepared as known by those skilled in the art by immunizing a suitable subject with a desired immunogen, e.g., polypeptide of the invention or fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique (Kohler G and Milstein C, 1975), the human B cell hybridoma technique (Kozbor D et al, 1982), the EBV-hybridoma technique (Cole S P et al, 1984), or trioma techniques (Hering S et al, 1988). To produce a hybridoma an immortal cell line (typically a myeloma) is fused to lymphocytes (typically splenocytes) from a mammal immunized with an immunogen, as described herein, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (Bierer B et al, 2002). Moreover, the ordinarily skilled worker will appreciate that there are many variations of such methods that also would be useful. Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide (Hayashi N et al, 1995; Hay B N et al, 1992; Huse W D et al, 1989; Griffiths A D et al, 1993). Kits for generating and screening phage display libraries are commercially available.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate a polypeptide of the invention by standard techniques, such as affinity chromatography or immunoprecipitation. An antibody specific for a polypeptide of the invention can facilitate the purification of a native polypeptide of the invention from biological materials, as well as the purification of recombinant form of a polypeptide of the invention from cultured cells (culture media or cells). Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein and/or metabolite levels in tissues such as blood as part of a risk assessment, diagnostic or prognostic test for cardiovascular, diabetic, metabolic disorder, and obesity or as part of a clinical testing procedure, e.g., to, for example, determine the efficacy of a given treatment regimen. Antibodies can be coupled to various enzymes, prosthetic groups, fluorescent materials, luminescent materials, bioluminescent materials, and radioactive materials to enhance detection. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include .sup.125I, 131I, 35S or 3H.

Highly purified antibodies (e.g. monoclonal humanized antibodies specific to a polypeptide encoded by the RBP4 gene of this invention) may be produced using GMP-compliant manufacturing processes well known in the art. These "pharmaceutical grade" antibodies can be used in novel therapies modulating activity and/or function of a polypeptide encoded by the RBP4 gene of this invention or modulating activity and/or function of a metabolic pathway related to the RBP4 gene of this invention.

Small Molecule and Other RBP4-Specific Modulators and Effects of Modulating RBP4 Expression Examples of small molecules that inhibit RBP4 include, but are not limited to, anthocyanin (cyanidin 3-glucoside; C3G), which ameliorated hyperglycemia and insulin sensitivity due to the reduction of retinol binding protein 4 (RBP4) expression in type 2 diabetic mice; fenretinide, (a specific Rbp4 inhibitor that is currently used in clinical trials as an antineoplastic agent), that was shown to restore insulin sensitivity in rodents fed on a high fat diet; rosiglitazone, an anti-diabetic agent found to lower plasma RBP4 in adipose Glut4−/− mice; DEAB (4-diethylaminobenzaldehyde), an inhibitor of RA synthesis caused reduction of rbp4 expression and inhibited zebra fish liver development; 1-phenyl-2-thiourea (PTU), which strongly down-regulated rbp4 expression in scale development of zebrafish; Retinal dehydrogenase (RALDH) and retinol dehydrogenase (ROLDH) which inhibit adipogenesis and suppresses peroxisome proliferator-activated receptor- and RXR responses, and vitamin A, all-trans-retinoic acid and citral, known inhibitors of Raldh enzymes, which prevent metabolism of Raldh, are also inhibitors of RBP4 action; antibodies to RBP4, which increased insulin sensitivity in ob/ob mice and reduced the EC50 for insulin stimulation of ERK1/2 phosphorylation; exercise and dietary calorie restriction in human subjects led to decrease in plasma levels of RBP4 and adipose tissue.

Antisense Compounds

The invention also provides a method for delivering one or more of the above-described nucleic acid molecules into cells that express RBP4 protein. A number of methods have been developed for delivering antisense DNA or RNA into cells. For example, antisense molecules can be introduced directly into a cell by electroporation, liposome-mediated transfection, CaCl-mediated transfection, or using a gene gun. Modified nucleic acid molecules designed to target the desired cells (e.g., antisense oligonucleotides linked to peptides or antibodies that specifically bind receptors or antigens expressed on the target cell surface) can be used. To achieve high intracellular concentrations of antisense oligonucleotides (as may be required to suppress translation on endogenous mRNAs), one approach utilizes a recombinant DNA construct in which the antisense oligonucleotide is placed under the control of a strong promoter (e.g., the CMV promoter).

Oligomeric compounds include, but are not limited to, oligonucleotides, oligonucleosides, oligonucleotide analogs, oligonucleotide mimetics, antisense compounds, antisense oligonucleotides, and siRNA. An oligomeric compound may be "antisense" to a target nucleic acid, meaning that it is capable of undergoing hybridization to a target nucleic acid through hydrogen bonding.

In certain embodiments, an antisense compound has a nucleobase sequence that, when written in the 5' to 3' direction, comprises the reverse complement of the target segment of a nucleic acid to which it is targeted, as described herein. In certain such embodiments, an antisense oligonucleotide has a nucleobase sequence that, when written in the 5' to 3' direction, comprises the reverse complement of the target segment of a nucleic acid to which it is targeted.

In certain embodiments, a RBP4-specific antisense compound is 8 to 80, 12 to 50, 12 to 30, 10 to 50, 10 to 30, 18 to 24, 19 to 22 or 15 to 30 subunits in length, as described herein. In other words, antisense compounds are from 8 to 80, 12 to 50, 12 to 30, 10 to 50, 10 to 30 or 15 to 30 linked subunits. In certain embodiments, an antisense compound targeted to a RBP4 nucleic acid or RBP4-specific nucleic acid is 12 to 30 subunits in length. In other words, antisense compounds are from 12 to 30 linked subunits. In certain embodiments, the antisense compound is 8 to 80, 12 to 50, 15 to 30, 18 to 24, 19 to 22, or 20 linked subunits. In certain embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In certain embodiments, the antisense compound is an antisense oligonucleotide, and the linked subunits are nucleotides.

In certain embodiments, a RBP4-specific antisense compound nucleic acid is 10 to 30 nucleotides in length. In certain such embodiments, an antisense oligonucleotide targeted to a RBP4 nucleic acid is 10, 11, 12, 13, 14, 15, 16, 17, 18, 19, 20, 21, 22, 23, 24, 25, 26, 27, 28, 29, or 30 nucleotides in length.

In certain embodiments, as described herein, an antisense oligonucleotide targeted to a RBP4 nucleic acid is 10 to 30 nucleotides in length. In certain such embodiments, as described herein, an antisense oligonucleotide targeted to a RBP4 nucleic acid is 10, 11, 12, 13, 14, 15, 16, 17, 18, 19, 20, 21, 22, 23, 24, 25, 26, 27, 28, 29, or 30 nucleotides in length.

In certain embodiments, a RBP4-specific antisense compound nucleic acid is 12 to 30 nucleotides in length, as described herein. In certain such embodiments, an antisense oligonucleotide targeted to a RBP4 nucleic acid is 12, 13, 14, 15, 16, 17, 18, 19, 20, 21, 22, 23, 24, 25, 26, 27, 28, 29, or 30 nucleotides in length.

In certain embodiments, an antisense oligonucleotide targeted to a RBP4 nucleic acid is 12 to 30 nucleotides in length, as described herein. In certain such embodiments, an antisense oligonucleotide targeted to a RBP4 nucleic acid is 12, 13, 14, 15, 16, 17, 18, 19, 20, 21, 22, 23, 24, 25, 26, 27, 28, 29, or 30 nucleotides in length.

In certain embodiments, a RBP4-specific antisense compound nucleic acid is 12 to 50 nucleotides in length, as described herein. In certain such embodiments, an antisense oligonucleotide targeted to a RBP4 nucleic acid is 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In certain embodiments, an antisense oligonucleotide targeted to a RBP4 nucleic acid is 12 to 50 nucleotides in length, as described herein. In certain such embodiments, an antisense oligonucleotide targeted to a RBP4 nucleic acid is 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In certain embodiment, a RBP4-specific antisense compound is 15 to 30 subunits in length, as described herein. In other words, antisense compounds are from 15 to 30 linked subunits. In certain such embodiments, the antisense compounds are 15, 16, 17, 18, 19, 20, 21, 22, 23, 24, 25, 26, 27, 28, 29, or 30 subunits in length.

In certain embodiments, an antisense oligonucleotide targeted to a RBP4 nucleic acid is 15 to 30 nucleotides in length, as described herein. In certain such embodiments, an antisense oligonucleotide targeted to a RBP4 nucleic acid is 15, 16, 17, 18, 19, 20, 21, 22, 23, 24, 25, 26, 27, 28, 29, or 30 nucleotides in length.

In certain embodiments, a RBP4-specific antisense compound is 18 to 24 subunits in length, as described herein. In other words, antisense compounds are from 18 to 24 linked subunits. In one embodiment, the antisense compounds are 18, 19, 20, 21, 22, 23, or 24 subunits in length.

In certain embodiments, an antisense oligonucleotide targeted to a RBP4 nucleic acid is 18 to 24 nucleotides in length, as described herein. In certain such embodiments, an antisense oligonucleotide targeted to a RBP4 nucleic acid is 18, 19, 20, 21, 22, 23, or 24 nucleotides in length.

In certain embodiments, a RBP4-specific antisense compound is 19 to 22 subunits in length, as described herein. In other words, antisense compounds are from 19 to 22 linked subunits. This embodies antisense compounds of 19, 20, 21, or 22 subunits in length.

In certain embodiments, an antisense oligonucleotide targeted to a RBP4 nucleic acid is 19 to 22 nucleotides in length, as described herein. In certain such embodiments, an antisense oligonucleotide targeted to a RBP4 nucleic acid is 19, 20, 21, or 22 nucleotides in length.

In certain embodiments, a RBP4-specific antisense compound is 20 subunits in length, as described herein. In certain such embodiments, antisense compounds are 20 linked subunits in length.

In certain embodiments, an antisense oligonucleotide targeted to a RBP4 nucleic acid is 20 nucleotides in length, as described herein. In certain such embodiments, an antisense oligonucleotide targeted to a RBP4 nucleic acid is 20 linked nucleotides in length. In certain embodiments, a shortened or truncated antisense compound targeted to a RBP4 nucleic acid has a single subunit deleted from the 5' end (5' truncation), or alternatively from the 3' end (3' truncation). A shortened or truncated antisense compound targeted to a RBP4 nucleic acid may have two subunits deleted from the 5' end or, alternatively, may have two subunits deleted from the 3' end of the antisense compound. Alternatively, the deleted nucleosides may be dispersed throughout the antisense compound; for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two are more additional subunits are present, the added subunits may be adjacent to each other; for example, in an antisense compound having two subunits added to the 5' end (5' addition), or alternatively to the 3' end (3' addition), of the antisense compound. Alternatively, the added subunits may be dispersed throughout the antisense compound; for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target-specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and 28 and 42 nucleobase antisense oligonucleotides comprised of the sequence of two or three of the tandem antisense oligonucleotides respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

PCT/US2007/068404 describes incorporation of chemically-modified high-affinity nucleotides into short antisense compounds about 8-16 nucleobases in length and that such compounds are useful in the reduction of target RNAs in animals with increased potency and improved therapeutic index.

In certain embodiments, antisense compounds targeted to RBP4 nucleic acid are short antisense compounds, as described herein. In certain embodiments, such short antisense compounds are oligonucleotide compounds. In certain embodiments, such short antisense compounds are about 8 to 16, preferably 9 to 15, more preferably 9 to 14, more preferably 10 to 14 nucleotides in length and comprise a gap region flanked on each side by a wing, wherein, each wing independently consists of 1 to 3 nucleotides. Preferred motifs include but are not limited to wing-deoxy gap-wing motifs selected from 3-10-3, 2-10-3, 2-10-2, 1-10-1, 2-8-2, 1-8-1, 3-6-3 or 1-6-1.

Antisense compounds targeted to RBP4 nucleic acid are synthesized in vitro and do not include antisense compositions of biological origin, or genetic vector constructs designed to direct the in vivo synthesis of antisense molecules.

In certain embodiments, an antisense compound is targeted to a region of a RBP4 nucleic acid that does not contain a single nucleotide polymorphism (SNPs), as described herein. In certain embodiments, an antisense compound is targeted to a region of a RBP4 nucleic acid that does contain a single nucleotide polymorph (SNPs). A single nucleotide polymorphism refers to polymorphisms that are the result of a single nucleotide alteration or the existence of two or more alternative sequences which can be, for example, different allelic forms of a gene. A polymorphism may comprise one or more base changes including, for example, an insertion, a repeat, or a deletion. In certain embodiments, the compounds provided herein, that target a region of RBP4 nucleic acid that contains one or more SNPs will contain the appropriate base substitution, insertion, repeat or deletion such that the compound is fully complementary to the altered RBP4 nucleic acid sequence.

In certain embodiments, RBP4 inhibitors can be antisense oligomeric compounds targeted to transthyretin (TTR), as described herein. TTR inhibition results in the lowering of RBP4 expression. RBP4 binds to TTR to form a protein complex that reduces renal clearance of RBP4. Circulating TTR levels are elevated in obese, insulin resistant humans in conjunction with increased RBP4 levels. Inhibiting circulating TTR level results in the reduction of serum RBP4 levels. The reduction in TTR, using a TTR inhibitor such as an antisense oligonucleotide, results in the reduction of circulating RBP4 levels, suggesting increased RBP4 renal clearance. In certain embodiments, the use of a TTR antisense oligonucleotide.

Antisense Compound Motifs

In certain embodiments, antisense compounds targeted to RBP4 nucleic acids have chemically modified subunits arranged in patterns, or motifs, to confer to the antisense compounds properties, such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may serve as a substrate for the cellular endonuclease RNase H, which cleaves the RNA strand of a RNA: DNA duplex.

Antisense compounds having a gapmer motif are considered chimeric antisense compounds, as described herein. In a gapmer, an internal position having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. The regions of a gapmer are differentiated by the types of sugar moieties comprising each distinct region. The types of sugar moieties that are used to differentiate the regions of a gapmer may in some embodiments, include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH$_2$)n-O-2' bridge, where n=1 or 2). In general, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region.

In some embodiments, an antisense compound targeted to RBP4 nucleic acids has a gap-widened motif, as described herein. In other embodiments, an antisense oligonucleotide targeted to RBP4 nucleic acids has a gap-widened motif.

PCT/US2006/0063730 describes incorporation of gap-widened antisense oligonucleotides having various wing-gap-wing motifs. In certain embodiments, a gap-widened motif includes, but is not limited to, 5-10-5, 2-13-5, 3-14-3, 3-14-4 gapmer motif.

In one embodiment, a gap-widened antisense oligonucleotide targeted to a RBP4 nucleic acid has a gap segment of fourteen 2'-deoxyribonucleotides positioned between wing segments of three chemically modified nucleosides. In one embodiment, the chemical modification comprises a 2'-sugar modification. In another embodiment, the chemical modification comprises a 2'-MOE sugar modification.

In one embodiment, antisense compounds targeted to RBP4 nucleic acid possess a 5-10-5 gapmer motif.

Target Nucleic Acids, Target Regions and Nucleotide Sequences

Nucleotide sequences that encode RBP4 include, without limitation, the following: GENBANK® Accession No. NM_011255.2, and incorporated herein as SEQ ID NO: 1; nucleotides 31300000 to 31311000 of GENBANK® Accession No. NT_039687.6, and incorporated herein as SEQ ID NO: 2; and GENBANK® Accession No. AK004839.1, and incorporated herein as SEQ ID NO: 3; and GENBANK Accession No. NM_006744.3, incorporated herein as SEQ ID NO: 5, and GENBANK Accession No. NM_013162.1, incorporated herein as SEQ ID NO: 84.

It is noted that some portions of these nucleotide sequences share identical sequence. For example, portions of SEQ ID NO: 1 are identical to portions of SEQ ID NO: 2; portions of SEQ ID NO: 1 are identical to portions of SEQ ID NO: 3; portions of SEQ ID NO: 1 are identical to portions of SEQ ID NO: 5, portions of SEQ ID NO: 1 are identical to portions of SEQ ID NO: 84 and portions of SEQ ID NO: 2 are identical to portions of SEQ ID NO: 3, portions of SEQ ID NO: 2 are identical to portions of SEQ ID NO: 5, portions of SEQ ID NO: 2 are identical to portions of SEQ ID NO: 84, portions of SEQ ID NO: 3 are identical to portions of SEQ ID NO: 5, portions of SEQ ID NO: 3 are identical to portions of SEQ ID NO: 84, and portions of SEQ ID NO: 5 are identical to portions of SEQ ID NO: 84. Accordingly, antisense compounds targeted to SEQ ID NO: 1 may also target SEQ ID NO: 2 and/or SEQ ID NO: 3, and/or SEQ ID NO: 5, and/or SEQ ID NO: 84; antisense compounds targeted to SEQ ID NO: 2 may also target SEQ ID NO: 1 and/or SEQ ID NO: 3, and/or SEQ ID NO: 5, and/or SEQ ID NO: 84; and antisense compounds targeted to SEQ ID NO: 3 may also target SEQ ID NO: 1 and/or SEQ ID NO: 2 and/or SEQ ID NO: 5, and/or SEQ ID NO: 84; compounds targeted to SEQ ID NO: 5 may also target SEQ ID NO: 1 and/or SEQ ID NO: 3, and/or SEQ ID NO: 2, and/or SEQ ID NO: 84; compounds targeted to SEQ ID NO: 84 may also target SEQ ID NO: 1 and/or SEQ ID NO: 3, and/or SEQ ID NO: 5, and/or SEQ ID NO: 2. Examples of such antisense compounds are shown in the following tables.

In certain embodiments, antisense compounds target a RBP4 nucleic acid having the sequence of GENBANK® Accession No. NM_011255.2 and incorporated herein as SEQ ID NO: 1; nucleotides 31300000 to 31311000 of GENBANK Accession No. NT_039687.6, and incorporated herein as SEQ ID NO: 2, and GENBANK® Accession No. AK004839.1, and incorporated herein as SEQ ID NO: 3, and GENBANK Accession No. NM_006744.3, incorporated herein as SEQ ID NO: 5, and GENBANK Accession No. NM_013162.1, incorporated herein as SEQ ID NO: 84. In certain such embodiments, an antisense oligonucleotide targets SEQ ID NO: 1, SEQ ID NO: 2, SEQ ID NO: 3, SEQ ID NO: 5, or SEQ ID NO: 84. In certain such embodiments, an antisense oligonucleotide that is targeted to SEQ ID NO: 1, SEQ ID NO: 2, SEQ ID NO: 3, SEQ ID NO: 5, or SEQ ID NO: 84 is at least 90% complementary to SEQ ID NO: 1, SEQ ID NO: 2, SEQ ID NO: 3, SEQ ID NO: 5, or SEQ ID NO: 84. In certain such embodiments, an antisense oligonucleotide that is targeted to SEQ ID NO: 1, SEQ ID NO: 2, SEQ ID NO: 3, SEQ ID NO: 5, or SEQ ID NO: 84 is at least 95% complementary to SEQ ID NO: 1, SEQ ID NO: 2, SEQ ID NO: 3, SEQ ID NO: 5, or SEQ ID NO: 84. In certain such embodiments, an antisense oligonucleotide that is targeted to SEQ ID NO: 1, SEQ ID NO: 2, SEQ ID NO: 3, SEQ ID NO: 5, or SEQ ID NO: 84 is 100% complementary to SEQ ID NO: 1, SEQ ID NO: 2, SEQ ID NO: 3, SEQ ID NO: 5, or SEQ ID NO: 84. In certain embodiments, an antisense oligonucleotide targeted to SEQ ID NO: 1, SEQ ID NO: 2, SEQ ID NO: 3, SEQ ID NO: 5, or SEQ ID NO: 84 comprises a nucleotide sequence selected from the nucleotide sequences set forth in Tables 1 and 24.

Hybridization

For example, hybridization may occur between an antisense compound disclosed herein, and a RBP4 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In one embodiment, the antisense compounds provided herein, are specifically hybridizable with a RBP4 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a RBP4 nucleic acid).

Non-complementary nucleobases between an antisense compound and a RBP4 nucleic acid may be tolerated provided that the antisense compound remains able to specifically hybridize to a target nucleic acid. Moreover, an antisense compound may hybridize over one or more segments of a RBP4 nucleic acid such that intervening or adjacent segments are not involved in the hybridization event (e.g., a loop structure, mismatch or hairpin structure).

In some embodiments, the antisense compounds provided herein, are at least 70%, at least 75%, at least 80%, at least 85%, at least 90%, at least 95%, at least 96%, at least 97%, at least 98% or at least 99% complementary to a RBP4 nucleic acid, as described herein. Percent complementarity of an antisense compound with a target nucleic acid can be determined using routine methods.

In other embodiments, the antisense compounds provided herein, are fully complementary (i.e, 100% complementary) to a target nucleic acid, as described herein. For example, an antisense compound may be fully complementary to a RBP4 nucleic acid. As used herein, "fully complementary" means each nucleobase of an antisense compound is capable of precise base pairing with the corresponding nucleobases of a target nucleic acid.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In one embodiment, antisense compounds up to 20 nucleobases in length comprise no more than 4, no more than 3, no more than 2 or no more than 1 non-complementary nucleobase(s) relative to a target nucleic acid, such as a RBP4 nucleic acid.

In another embodiment, antisense compounds up to 30 nucleobases in length comprise no more than 6, no more than 5, no more than 4, no more than 3, no more than 2 or no more than 1 non-complementary nucleobase(s) relative to a target nucleic acid, such as a RBP4 nucleic acid.

The antisense compounds provided herein, also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In one embodiment, the antisense compounds are complementary to at least an 8 nucleobase portion of a target segment. In another embodiment, the antisense compounds are complementary to at least a 12 nucleobase portion of a target segment. In yet another embodiment, the antisense compounds are complementary to at least a 15 nucleobase portion of a target segment. Also contemplated are antisense compounds that are complementary to at least 9, 10, 11, 12, 13, 14, 15, 16, 17, 18, 19, or 20 or more nucleobase portion of a target segment, or a range defined by any two or more target segments.

In certain embodiments, an antisense compounds provided herein include those comprising a portion which consists of at least 8, 9, 10, 11, 12, 13, 14, 15, 16, 17, 18, 19, 20, or 21 contiguous nucleobases of the nucleobase sequence as set forth in SEQ ID NOs: 1, 2, 3, 5, 84, or 86. In certain embodiments, the antisense compounds are complementary to an equal-length portion of SEQ ID NO: 1, 2, 3, 5, 84, or 86. In certain embodiments, the antisense compounds are at least 75%, 80%, 85%, 90%, 95%, or 100% complementary to SEQ ID NO 1, 2, 3, 5, 84, or 86.

Antisense oligonucleotides with the following ISIS Nos exhibited at least 65% inhibition of RBP4 mRNA levels: 403570, 403577, 403589, 403531, 403532, 403555, 403602, 403539, 403548, 403571, 403598, 403530, 403536, 403553, 403582, 403528, 403576, 403527, 403549, 403543, 403578, 403563, 403541, 403544, 403538, and 403542. The target segments to which these antisense oligonucleotides are targeted are active target segments. The target regions to which these antisense oligonucleotides are targeted are active target regions.

Antisense oligonucleotides with the following ISIS Nos exhibited at least 70% inhibition of RBP4 mRNA levels: 403582, 403528, 403576, 403527, 403549, 403543, 403578, 403563, 403541, 403544, 403538, and 403542. The target segments to which these antisense oligonucleotides are targeted are active target segments. The target regions to which these antisense oligonucleotides are targeted are active target regions.

Antisense oligonucleotides with the following ISIS Nos exhibited at least 75% inhibition of RBP4 mRNA levels: 403543, 403578, 403563, 403541, 403544, 403538, and 403542. The target segments to which these antisense oligonucleotides are targeted are active target segments. The target regions to which these antisense oligonucleotides are targeted are active target regions.

Antisense oligonucleotides with the following ISIS Nos exhibited at least 80% inhibition of RBP4 mRNA levels: 403563, 403541, 403544, 403538, and 403542. The target segments to which these antisense oligonucleotides are targeted are active target segments. The target regions to which these antisense oligonucleotides are targeted are active target regions.

Antisense oligonucleotides with the following ISIS Nos exhibited at least 85% inhibition of RBP4 mRNA levels: 403541, 403544, 403538, and 403542. The target segments to which these antisense oligonucleotides are targeted are active target segments. The target regions to which these antisense oligonucleotides are targeted are active target regions.

Antisense oligonucleotides with the following ISIS Nos exhibited at least 90% inhibition of RBP4 mRNA levels: 403542. The target segments to which these antisense oligonucleotides are targeted are active target segments. The target regions to which these antisense oligonucleotides are targeted are active target regions.

Identity

The antisense compounds provided herein, may also have a defined percent identity to a particular nucleotide sequence, SEQ ID NO, or compound represented by a specific Isis number. As used herein, an antisense compound is identical to the sequence disclosed herein, if it has the same nucleobase pairing ability. For example, an RNA which contains uracil in place of thymidine in a disclosed DNA sequence would be considered identical to the DNA sequence since both uracil and thymidine pair with adenine. Shortened and lengthened versions of the antisense compounds described herein, as well as compounds having non-identical bases relative to the antisense compounds provided herein, also are contemplated. The non-identical bases may be adjacent to each other or dispersed throughout the antisense compound. Percent identity of an antisense compound is calculated according to the number of bases that have identical base pairing relative to the sequence to which it is being compared.

In one embodiment, the antisense compounds are at least 70%, at least 75%, at least 80%, at least 85%, at least 90%, at least 95% or 100% identical to one or more of the antisense compounds disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties, such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus-containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In one embodiment, antisense compounds targeted to RBP4 nucleic acid comprise one or more modified internucleoside linkages. In some embodiments, a the modified internucleoside linkages are phosphorothioate linkages. In other embodiments, each internucleoside linkage of an antisense compound is a phosphorothioate internucleoside linkage.

Modified Sugar Moieties

Antisense compounds targeted to a RBP4 nucleic acid may contain one or more nucleotides having modified sugar moieties. Sugar modifications may impart nuclease stability, binding affinity or some other beneficial biological property to the antisense compounds. The furanosyl sugar ring of a nucleoside can be modified in a number of ways including, but not limited to, addition of a substituent group, particularly at the 2' position; bridging of two non-geminal ring atoms to form a bicyclic nucleic acid (BNA); and substitution of an atom or group, such as —S—, —N(R)— or —C($R_1$)($R_2$) for the ring oxygen at the 4'-position. Modified sugars include, but are not limited to, substituted sugars, especially 2'-substituted sugars having a 2'-F, 2'-$OCH_2$ (2'-OMe) or a 2'-O($CH_2$)$_2$—$OCH_3$ (2'-O-methoxyethyl or 2'-MOE) substituent group; and bicyclic modified sugars (BNAs), having a 4'-($CH_2$)$_n$—O-2' bridge, where n=1 or n=2, including α-L-Methyleneoxy (4'-CH2-O-2') BNA, β-D-Methyleneoxy (4'-$CH_2$—O-2') BNA and Ethyleneoxy (4'-($CH_2$)$_2$-O-2') BNA. Bicyclic modified sugars also include (6'S)-6' methyl BNA, Aminooxy (4'-CH2-O—N(R)-2') BNA, Oxyamino (4'-CH2-N(R)—O-2') BNA wherein, R is, independently, H, a protecting group, or C1-C12 alkyl. The substituent at the 2' position can also be selected from alyl, amino, azido, thio, O-allyl, O—C1-C10 alkyl, $OCF_3$, O($CH_2$)$_2SCH_3$, O($CH_2$)$_2$—O—N(Rm)(Rn), and O—$CH_2$—C(=O)—N(Rm)(Rn), where each Rm and Rn is, independently, H or substituted or unsubstituted C1-C10 alkyl. In certain embodiments, such BNA-modified nucleotides are high-affinity nucleotides and their incorporation into antisense compounds allows for increased potency and improved therapeutic index. Methods for the preparation of modified sugars are well known to those skilled in the art.

Examples of nucleosides having modified sugar moieties include without limitation nucleosides comprising 5'-vinyl, 5'-methyl (R or S), 4'-S, 2'-F, 2'-$OCH_3$ and 2'—O($CH_2$)$_2OCH_3$ substituent groups. The substituent at the 2' position can also be selected from allyl, amino, azido, thio, O-allyl, O—$C_1$-$C_{10}$ alkyl, $OCF_3$, O($CH_2$)$_2SCH_3$, O($CH_2$)$_2$—O—N($R_m$)($R_n$), and O—$CH_2$—C(=O)—N($R_m$)($R_n$), where each $R_m$ and $R_n$ is, independently, H or substituted or unsubstituted $C_1$-$C_{10}$ alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-($CH_2$)—O-2' (LNA); 4'-($CH_2$)—S-2; 4'-($CH_2$)—O-2' (LNA); 4'-($CH_2$)$_2$—O-2' (ENA); 4'-C($CH_3$)$_2$—O-2' (see PCT/US2008/068922); 4'-CH($CH_3$)—O-2' and 4'-CH($CH_2OCH_3$)—O-2' (see U.S. Pat. No. 7,399,845, issued on Jul. 15, 2008); 4'-$CH_2$—N($OCH_3$)-2' (see PCT/US2008/064591); 4'-$CH_2$—O—N($CH_3$)-2' (see published U.S. Patent Application US2004-0171570, published Sep. 2, 2004); 4'-$CH_2$—N(R)—O-2' (see U.S. Pat. No. 7,427,672, issued on Sep. 23, 2008); 4'-$CH_2$—C($CH_3$)-2' and 4'-$CH_2$—C(=$CH_2$)-2' (see PCT/US2008/066154); and wherein R is, independently, H, $C_1$-$C_{12}$ alkyl, or a protecting group. Each of the foregoing BNAs include various stereochemical sugar configurations including for example α-L-ribofuranose and β-D-ribofuranose (see PCT international application PCT/DK98/00393, published on Mar. 25, 1999 as WO 99/14226).

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

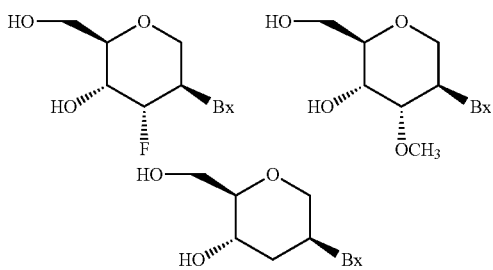

Many other bicyclo and tricyclo sugar surrogate ring systems are also know in the art that can be used to modify nucleosides for incorporation into antisense compounds (see for example review article: Leumann, Christian J.). Such ring systems can undergo various additional substitutions to enhance activity.

In nucleotides having modified sugar moieties, the nucleobase moieties (natural, modified or a combination thereof) are maintained for hybridization with an appropriate nucleic acid target.

In one embodiment, antisense compounds targeted to RBP4 nucleic acid comprise one or more nucleotides having modified sugar moieties. In a suitable embodiment, the modified sugar moiety is 2'-MOE. In other embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been described to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo, particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example, 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In one embodiment, antisense compounds targeted to a RBP4 nucleic acid comprise one or more modified nucleobases. In an additional embodiment, gap-widened antisense oligonucleotides targeted to RBP4 nucleic acid comprise one or more modified nucleobases. In some embodiments, the modified nucleobase is 5-methylcytosine. In further embodiments, each cytosine is a 5-methylcytosine.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties, such as nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of RBP4 nucleic acids can be tested in vitro in a variety of cell types. Cell types used for such analyses are available from commerical vendors (e.g. American Type Culture Collection, Manassus, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, HepB3 cells, and primary hepatocytes.

In Vitro Testing of Antisense Oligonucleotides

Described herein, are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE® (Invitrogen, Carlsbad, Calif.). Antisense oligonucleotides are mixed with LIPOFECTAMINE® in OPTI-MEM®1 reduced medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in replicates, the data are presented as the average of the replicate treatments.

The concentration of antisense oligonucleotides used varies from cell line to cell line. Methods to determine the optimal antisense oligonucleotide concentration for a particular cell line are well known in the art. Antisense oligonucleotides are typically used at concentrations ranging from 1 nM to 300 nM.

RNA Isolation

RNA analysis can be performed on total cellular RNA or poly(A)+ mRNA. RNA is prepared using methods well known in the art, for example, using the TRIZOL® Reagent (Invitrogen, Carlsbad, Calif.), according to the manufacturer's recommended protocols.

Analysis of Inhibition of Target Levels or Expression

Inhibition of the level or expression of RBP4 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.), according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as GAPDH, or by quantifying total RNA using RIBOGREEN® (Invitrogen, Inc., Carlsbad, Calif.). GAPDH expression is quantified by real time PCR, by being run simultaneously with the target, multiplexing, or separately. Methods of RNA quantification by RIBOGREEN® are mentioned in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to RBP4 nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of RBP4 nucleic acids can be assessed by measuring RBP4 protein levels. Protein levels of RBP4 can be evaluated or quantitated in a variety of ways well known in the art, such as immunoprecipitation, Western blot analysis (immunoblotting), enzyme-linked immunosorbent assay (ELISA), quantitative protein assays, protein activity assays (e.g., caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies for the detection of human and rat RBP4 are commercially available.

In Vivo Testing of Antisense Compounds

Antisense compounds, for example, antisense oligonucleotides, are tested in animals to assess their ability to inhibit expression of RBP4 and produce phenotypic changes, such as decreased plasma glucose, plasma triglycerides, plasma cholesterol, and body weight. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from liver tissue and changes in RBP4 nucleic acid expression are measured.

Combination Therapy

The invention also provides methods of combination therapy, wherein, one or more RBP4-specific modulators of the invention and one or more other therapeutic/prophylactic agents are administered treat a condition and/or disease state as described herein. In various aspects, RBP4-specific modulator(s) of the invention and the therapeutic/prophylactic agent (s) are co-administered as a mixture or administered separately. In one aspect, the route of administration is the same for the RBP4-specific modulators (s) of the invention and the therapeutic/prophylactic agent(s), while in other aspects, the RBP4-specific modulators (s) of the invention and the therapeutic/prophylactic agents (s) are administered by different routes. In one embodiment, the dosages of the RBP4-specific modulator(s) of the invention and the therapeutic/prophylactic agent(s) are amounts that are therapeutically or prophylactically effective for each RBP4-specific modulator when administered separately. Alternatively, the combined administration permits use of lower dosages than would be required to achieve a therapeutic or prophylactic effect if administered separately, and such methods are useful in decreasing one or more side effects of the reduced-dose RBP4-specific modulator.

In certain embodiments, one or more RBP4-specific modulators are co-administered with one or more other RBP4-specific modulators, as described herein. In certain embodiments, such one or more other RBP4-specific modulators are designed to treat the same disease or condition as the one or more pharmaceutical compositions of the present invention, as described herein. In certain embodiments, such one or more other RBP4-specific modulators are designed to treat a different disease or condition as the one or more pharmaceutical compositions of the present invention, as described herein. In certain embodiments, such one or more other RBP4-specific modulators are designed to treat an undesired effect of one or more pharmaceutical compositions of the present invention, as described herein. In certain embodiments, one or more pharmaceutical compositions are co-administered with another RBP4-specific modulator to treat an undesired effect of that other RBP4-specific modulator, as described herein. In certain embodiments, one or more RBP4-specific modulators of the present invention and one or more other RBP4-specific modulators are administered at the same time, as described herein. In certain embodiments, one or more pharmaceutical compositions of the present invention and one or more other RBP4-specific modulators are administered at different times, as described herein. In certain embodiments, one or more pharmaceutical compositions of the present invention and one or more other RBP4-specific modulators are prepared together in a single formulation, as described herein. In certain embodiments, one or more pharmaceutical compositions of the present invention and one or more other RBP4-specific modulators are prepared separately, as described herein.

In certain embodiments, RBP4-specific modulators that may be co-administered with a pharmaceutical composition comprising a RBP4-specific antisense compound include glucose-lowering agents and therapies, as described herein. In some embodiments, the glucose-lowering agent is a PPAR agonist (gamma, dual, or pan), a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, a meglitinide, a thiazolidinedione, or a sulfonylurea.

In some embodiments, the glucose-lowering therapeutic is a GLP-1 analog. In some embodiments, the GLP-1 analog is exendin-4 or liraglutide.

In other embodiments, the glucose-lowering therapeutic is a sulfonylurea. In some embodiments, the sulfonylurea is acetohexamide, chlorpropamide, tolbutamide, tolazamide, glimepiride, a glipizide, a glyburide, or a gliclazide.

In some embodiments, the glucose lowering drug is a biguanide. In some embodiments, the biguanide is metformin, and in some embodiments, blood glucose levels are decreased without increased lactic acidosis as compared to the lactic acidosis observed after treatment with metformin alone.

In some embodiments, the glucose lowering drug is a meglitinide. In some embodiments, the meglitinide is nateglinide or repaglinide.

In some embodiments, the glucose-lowering drug is a thiazolidinedione. In some embodiments, the thiazolidinedione is pioglitazone, rosiglitazone, or troglitazone. In some embodiments, blood glucose levels are decreased without greater weight gain than observed with rosiglitazone treatment alone.

In some embodiments, the glucose-lowering drug is an alpha-glucosidase inhibitor. In some embodiments, the alpha-glucosidase inhibitor is acarbose or miglitol.

In a certain embodiment, a co-administered glucose-lowering agent is an antisense oligonucleotide targeted to RBP4.

In a certain embodiment, glucose-lowering therapy is therapeutic lifestyle change.

In certain such embodiments, the glucose-lowering agent is administered prior to administration of a pharmaceutical composition of the present invention, as described herein. In certain such embodiments, the glucose-lowering agent is administered following administration of a pharmaceutical composition of the present invention. In certain such embodiments, the glucose-lowering agent is administered at the same time as a pharmaceutical composition of the present invention. In certain such embodiments, the dose of a co-administered glucose-lowering agent is the same as the dose that would be administered if the glucose-lowering agent was administered alone. In certain such embodiments, the dose of a co-administered glucose-lowering agent is lower than the dose that would be administered if the glucose-lowering agent was administered alone. In certain such embodiments, the dose of a co-administered glucose-lowering agent is greater than the dose that would be administered if the glucose-lowering agent was administered alone.

In certain embodiments, RBP4-specific modulators that may be co-administered with a pharmaceutical composition comprising a RBP4-specific antisense compound include anti-obesity agents. Such anti-obesity agents therapeutics may be administered as described above as fat or body weight or adipose tissue mass reducing agents.

Further provided is a method of administering a RBP4-specific antisense compound via injection and further including administering a topical steroid at the injection site.

In certain embodiments, RBP4-specific modulators that may be co-administered with a pharmaceutical composition of the present invention include lipid-lowering agents. In certain such embodiments, RBP4-specific modulators that may be co-administered with a pharmaceutical composition of the present invention include, but are not limited to atorvastatin, simvastatin, rosuvastatin, and ezetimibe. In certain such embodiments, the lipid-lowering agent is administered prior to administration of a pharmaceutical composition of the present invention. In certain such embodiments, the lipid-lowering agent is administered following administration of a pharmaceutical composition of the present invention. In certain such embodiments, the lipid-lowering agent is administered at the same time as a pharmaceutical composition of the present invention. In certain such embodiments, the dose of a co-administered lipid-lowering agent is the same as the dose that would be administered if the lipid-lowering agent was administered alone. In certain such embodiments, the dose of a co-administered lipid-lowering agent is lower than the dose that would be administered if the lipid-lowering agent was administered alone. In certain such embodiments, the dose of a co-administered lipid-lowering agent is greater than the dose that would be administered if the lipid-lowering agent was administered alone.

In certain embodiments, a co-administered lipid-lowering agent is a HMG-CoA reductase inhibitor. In certain such embodiments, as described herein the HMG-CoA reductase inhibitor is a statin. In certain such embodiments, as described herein the statin is selected from atorvastatin, simvastatin, pravastatin, fluvastatin, and rosuvastatin.

In certain embodiments, a co-administered lipid-lowering agent is a cholesterol absorption inhibitor. In certain such embodiments, cholesterol absorption inhibitor is ezetimibe.

In certain embodiments, a co-administered lipid-lowering agent is a co-formulated HMG-CoA reductase inhibitor and cholesterol absorption inhibitor. In certain such embodiments, the co-formulated lipid-lowering agent is ezetimibe/simvastatin.

In certain embodiments, a co-administered lipid-lowering agent is a microsomal triglyceride transfer protein inhibitor (MTP inhibitor).

In certain embodiments, a co-administered lipid-lowering agent is an oligonucleotide targeted to ApoB.

In certain embodiments, a co-administered RBP4-specific modulator is a bile acid sequestrant. In certain such embodiments, the bile acid sequestrant is selected from cholestyramine, colestipol, and colesevelam.

In certain embodiments, a co-administered RBP4-specific modulator is a nicotinic acid. In certain such embodiments, the nicotinic acid is selected from immediate release nicotinic acid, extended release nicotinic acid, and sustained release nicotinic acid.

In certain embodiments, a co-administered RBP4-specific modulator is a fibric acid. In certain such embodiments, a fibric acid is selected from gemfibrozil, fenofibrate, clofibrate, bezafibrate, and ciprofibrate.

Further examples of RBP4-specific modulators that may be co-administered with a pharmaceutical composition of the present invention include, but are not limited to, corticosteroids, including but not limited to prednisone; immunoglobulins, including, but not limited to intravenous immunoglobulin (IVIg); analgesics (e.g., acetaminophen); anti-inflammatory agents, including, but not limited to non-steroidal anti-inflammatory drugs (e.g., ibuprofen, COX-1 inhibitors, and COX-2, inhibitors); salicylates; antibiotics; antivirals; antifungal agents; antidiabetic agents (e.g., biguanides, glucosidase inhibitors, insulins, sulfonylureas, and thiazolidinediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

In certain embodiments, the pharmaceutical compositions of the present invention may be administered in conjunction with a lipid-lowering therapy. In certain such embodiments, a lipid-lowering therapy is therapeutic lifestyle change. In certain such embodiments, a lipid-lowering therapy is LDL apheresis.

Glucose-Lowering Drugs/Agents/Therapeutics, Anti-Obesity Drugs/Agents/Therapeutics, Lipid-Lowering Drugs/Agents/Therapeutics Compounds of the invention may be used in combination therapies, wherein, an additive effect is achieved by administering one or more compounds of the invention and one or more other suitable therapeutic/prophylactic compounds to treat a condition. Suitable therapeutic/prophylactic compound(s) include, but are not limited to, glucose-lowering agents (also referred to herein, as glucose-lowering drugs or glucose-lowering therapeutics), anti-obesity agents (also referred to herein, as anti-obesity drugs or anti-obesity therapeutics), and lipid lowering agents (also referred to herein, as lipid-lowering drugs or lipid-lowering therapeutics). Glucose lowering agents include, but are not limited to, PPAR agonists, dipeptidyl peptidase (IV) inhibitors, GLP-1 analogs, insulin or insulin analogs, insulin secretagogues, SGLT2 inhibitors, human amylin analogs, biguanides, or alpha-glucosidase inhibitors. Glucose lowering agents include, but are not limited to hormones, hormone mimetics, or incretin mimetics (e.g., insulin, including inhaled insulin, GLP-1 or GLP-1 analogs such as liraglutide, or exenatide), DPP (IV) inhibitors, a sulfonylurea (e.g., acetohexamide, chlorpropamide, tolbutamide, tolazamide, glimepiride, a glipizide, glyburide or a gliclazide), a biguanide (metformin), a meglitinide (e.g., nateglinide or repaglinide), a thiazolidinedione or other PPAR-gamma agonists (e.g., pioglitazone or rosiglitazone) an alpha-glucosidase inhibitor (e.g., acarbose or miglitol), antisense compounds targeted to RBP4, or and antisense compound not targeted to RBP4. Also included are dual PPAR-agonists (e.g., muraglitazar, being developed by Bristol-Myers Squibb, or tesaglitazar, being developed by AstraZeneca). Also included are other diabetes treatments in development (e.g. LAF237, being developed by Novartis; MK-0431, being developed by Merck; or rimonabant, being developed by Sanofi-Aventis). Also included are GLP-1 mimetics in development, including, but not limited to, those being developed by Roche, ConjuChem, Sanofi-Aventis, Teijin Pharma Limited, Ipsen Pharmaceuticals, and Servier Research Institute. Also included are SGLT2 inhibitors in development, including, but not limited to, those being developed by Glaxo Smith Kline or AVE2268 in development at Sanofi-Aventis. Also included are DPP (IV) inhibitors in development, including, but not limited to, those being developed by Novartis (e.g. vildagliptin), Merck, GSK, or BMS. Also included are glucokinase inhibitors in development. Anti-obesity agents include, but are not limited to, appetite suppressants (e.g. phentermine or Meridia™), fat absorption inhibitors such as orlistat (e.g. Xenical™), and modified forms of ciliary neurotrophic factor which inhibit hunger signals that stimulate appetite. Anti-obesity agents include peripheral or CNS-based agents. Lipid lowering agents include, but are not limited to, bile salt sequestering resins (e.g., cholestyramine, colestipol, and colesevelam hydrochloride), HMGCoA-reductase inhibitors (e.g., lovastatin, pravastatin, atorvastatin, simvastatin, and fluvastatin), nicotinic acid, fibric acid derivatives (e.g., clofibrate, gemfibrozil, fenofibrate, bezafibrate, and ciprofibrate), probucol, neomycin, dextrothyroxine, plant-stanol esters, cholesterol absorption inhibitors (e.g., ezetimibe), CETP inhibitors (e.g. torcetrapib, and JTT-705) MTP inhibitors (e.g., implitapide), inhibitors of bile acid transporters (apical sodium-dependent bile acid transporters), regulators of hepatic CYP7a, ACAT inhibitors (e.g. Avasimibe), estrogen replacement therapeutics (e.g., tamoxigen), synthetic HDL (e.g. ETC-216), anti-inflammatories (e.g., glucocorticoids), antisense compounds targeted to RBP4, or an antisense compound not targeted to RBP4. One or more of these drugs may be combined with one or more of the RBP4-specific modulators, such as RBP4 specific inhibitors, to achieve an additive therapeutic effect.

Diabetes agents, including insulin, other hormones and hormone analogs and mimetics, and other glucose lowering agents, including orally administered glucose lowering drugs, may also be combined with antisense inhibitors of RBP4. The term "glucose-lowering agent" includes, but is not limited to, the sulfonylureas, biguanides, meglitinides, peroxisome proliferator-activated receptor-gamma (PPAR-gamma) agonists (e.g., thiazolidinediones) and alpha-glucosidase inhibitors.

Sulfonylureas work by stimulating beta-cell insulin secretion in the pancreas, and may also improve insulin sensitivity in peripheral tissues. Early sulfonylureas such as acetohexamide (Dymelor™), chlorpropamide (Diabinese™, Glucamide™), tolbutamide (Orinase™, Mobenol™), and tolazamide (Tolamide™, Tolinase™) have been generally replaced with newer sulfonureas with better side-effect profiles (specifically lower cardiovascular risk), such as glimepiride (Amaryl™), glipizide (Glucotrol™), glipizide extended release (Glucotrol XL™), glyburide (Micronase™, Euglucon™, Diabeta™), gliclazide (Diamicron™, and micronized glyburide (Glynase™) (Luna & Feinglos; AAC E et al., 2002). Side effects of sulfonylureas include hypoglycemia and weight gain.

Biguanides such as Metformin (Glucophage™) work by decreasing hepatic glucose output and enhancing insulin sensitivity in hepatic and peripheral tissues. Metformin is contraindicated in patients with congestive heart failure or severe liver disease.

Meglitinides work by stimulating the beta cells in the pancreas to produce insulin. Nateglinide (Starlix™) and repaglinide (Prandin™) are examples of this class.

Peroxisome proliferator-activated receptor-gamma (PPAR-gamma) agonists such as the thiazolidinediones enhance insulin sensitivity in muscle and adipose tissue and, to a lesser extent, inhibit hepatic glucose production. Thiazolidinediones include pioglitazone (Actos™) and rosiglitazone (Avandia™; GlaxoSmithKline). The first thiazolidinedione approved for use in the United States, troglitazone (Rezulin™), was withdrawn from the market because of severe liver toxicity. Thiazolidinediones also affect the lipid profiles of patients with type 2 diabetes. Studies have described that rosiglitazone is associated with increases in total, LDL, and HDL cholesterol levels, and either no changes or increases in triglyceride levels. Pioglitazone has been associated with mean decreases in triglyceride levels, mean increases in HDL cholesterol levels, and no consistent mean changes in LDL and total cholesterol levels. Other potential side effects associated with thiazolidinediones include weight gain, slow onset of action, and potential liver toxicity (Luna & Feinglos, 2001).

New PPAR-gamma agonists are being developed; these include isaglitazone (netoglitazone) and the dual-acting PPAR agonists which have affinities for both PPAR-gamma and PPAR-alpha. Examples of dual-acting PPAR agonists are BMS-298585 and tesaglitazar. Agonists of other PPARs (e.g., alpha, delta) or pan-PPAR agonists may also be useful.

Alpha-glucosidase inhibitors inhibit an enzyme found in the lining of the small intestine that is responsible for the breakdown of complex carbohydrates before they are absorbed. Such inhibitors include acarbose (Precose™) and miglitol (Glyset™).

Oral glucose-lowering drugs are often used in combination to treat Type 2 diabetes. While many combinations of the above are possible, several are already marketed as a combined formulation (for example, Avandamet™ (Rosiglitazone+Metformin); Glucovance™ (glyburide/metformin); and Metaglip™ (glipizide/metformin). These and other combined formulations for treatment of diabetes or obesity may be administered in combination with one or more of the RBP4-specific modulators or inhibitors.

Other classes of glucose-lowering, diabetes drugs are being developed. As alternatives to regular insulin, which is administered by injection, insulin analogs such as insulin lispro (Humalog™) and insulin glargine (Lantus™) may be used. Both are given by injection as is regular insulin, but result in fewer hypoglycemic events than regular insulin. In addition the onset and duration of action with these is different from regular insulin. A follow-up analog to insulin glargine, insulin glulisine, is being developed by Aventis. Novo Nordisk is developing insulin detemir, a long-acting analog.

Alternative formulations/delivery methods for regular insulin are also being developed. Both liquid and dry powder inhaled insulin formulations are currently in late-stage development or have been recently approved examples include recently approved Exubera™ (Nektar/Pfizer/Aventis), which is a powder, and AERx™ (Aradigm/Novo Nordisk), which is an aerosolized liquid. While inhaled insulin is expected to be viewed as more convenient and less invasive than injected insulin, the cost is expected to be much greater for inhaled insulin.

Several companies are developing oral formulations of insulin. Oralin™ (Generex Biotechnology) is the farthest along in development but there are others.

Other hormones and hormone mimetics being developed include pramlintide acetate (Symlin™), and GLP-1. GLP-1 receptor agonists and GLP-1 analogs are being evaluated for clinical use as antidiabetic agents. GLP-1 itself has a short half-life due to N-terminal degradation of the peptide by Dipeptidyl Peptidase (DPP-IV)-mediated cleavage at the position 2 alanine. This limits the clinical usefulness of native GLP-1 or synthetic versions thereof. Longer acting analogs have been developed, including Exendin-4 (Exenatide™, Exenatide LAR™), a DP IV-resistant GLP-1 analog and Liraglutide™, an acylated albumin-bound human GLP-1 analog.

DPP-IV inhibitors are also being explored as drugs and one (LAF-237, Novartis) is currently in advanced clinical trials. Glucagon inhibitors may also be useful for diabetes.

Other peptides such as pituitary adenylate cyclase-activating polypeptide (PACAP) and Peptide YY (PYY) (and its subpeptide PYY[3-36]) are also under study for diabetes and/or obesity (Yamamoto et al., 2003, Diabetes 52, 1155-1162; Pittner et al., Int. J. Obes. Relat. Metab. Disord. 2004, 28, 963-71).

Any of the aforementioned glucose-lowering drugs are useful in combination with one or more of the RBP4-specific modulators or inhibitors, such as an antisense inhibitor of RBP4 as described herein. One or more of these drugs may be combined in a single composition with one or more of the RBP4-specific modulators or inhibitors, or used in therapies for combined administration, i.e., sequential or concurrent administration thereof.

Antisense inhibition of RBP4 is described herein, below to reduce weight gain of animals on high-fat diets and may be useful in treatment of obesity. The use of weight loss agents has also been considered useful in diabetes management in general and for delaying or preventing the development or progression of frank Type 2 diabetes in patients with impaired glucose tolerance (Heymsfield S B, 2000, Archives of Internal Medicine, 160, 1321-1326). Thus, anti-obesity drugs are useful in combination with antisense inhibitors of RBP4 expression in pharmaceutical compositions or in combined therapeutic regimens. Examples of anti-obesity drugs (also called "diet drugs") include, without limitation, appetite suppressants such as phentermine and Meridia™, fat absorption inhibitors or lipase inhibitors such as orlistat (Xenical™), and Axokine™, a modified form of ciliary neurotrophic factor, which inhibits hunger signals that stimulate appetite, CB-1 selective agonists such as Rimonabant, 5HT2c agonists, amylin analogues such as pramlintide, sibutramine, GLP-1 agonists such as Byetta. Other drugs or classes of drugs under evaluation for obesity are CB1 inverse agonists, PYY, MCH4 and MTP inhibitors.

In certain embodiments, additional therapies or therapeutic agents may also include, for example, but are not limited to, insulin and insulin analogues; insulin secretagogues including sulphonylureas (for example glibenclamide, glipizide) and prandial glucose regulators (for example repaglinide, nateglinide); insulin sensitising agents including PPARg agonists (for example pioglitazone and rosiglitazone); agents that suppress hepatic glucose output (for example metformin); agents designed to reduce the absorption of glucose from the intestine (for example acarbose); agents designed to treat the complications of prolonged hyperglycemia; anti-obesity agents (for example sibutramine, orlistat, aP2 inhibitors (such as those disclosed in U.S. Ser. No. 09/519,079 filed Mar. 6, 2000); melanocortin receptor (MC4R) agonist, a melanin-concentrating hormone receptor (MCHR) antagonist, a growth hormone secretagogue receptor (GHSR) antagonist, an orexin receptor antagonist, a CCK (cholecystokinin) agonist, a GLP-1 agonists, NPY1 or NPY5 antagonist, a corticotropin releasing factor (CRF) antagonist, a histamine receptor-3 (H3) modulator, a PPAR.gamma. modulator, a PPAR.delta. modulator, a beta 3 adrenergic agonist, a lipase inhibitor, a serotonin (and dopamine) reuptake inhibitor, a erotonin receptor agonist (e.g. BVT-933), an aP2 inhibitor, a thyroid receptor agonist and/or an anorectic agent, anti-dyslipidaemia agents such as, HMG-CoA reductase inhibitors (statins, e.g. pravastatin); PPAR.alpha. agonists (fibrates, e.g. gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations); Antihypertensive agents such as, .beta. blockers (e.g. atenolol, inderal); ACE inhibitors (e.g. lisinopril); calcium antagonists (e.g., nifedipine); angiotensin receptor antagonists (e.g. candesartan), a antagonists and diuretic agents (e.g. furosemide, benzthiazide); Homeostasis modulators such as, antithrombotics, activators of fibrinolysis and antiplatelet agents; thrombin antagonists; factor Xa inhibitors; factor VIIa inhibitors); antiplatelet agents (e.g. aspirin, clopidogrel); anticoagulants (heparin and Low molecular weight analogues, hirudin) and warfarin; and Anti-inflammatory agents, such as non-steroidal anti-inflamatory drugs (e.g. aspirin) and steroidal anti-inflammatory agents (e.g. cortisone).

In certain embodiments, combination therapies with additional therapies, as provided herein, may be combined into a single composition or kept as separate compositions.

In certain embodiments, RBP4-specific modulators or inhibitors may be administered at the same time or at different times with combined additional therapies or therapeutic agents. Examples of combined additional therapies or therapeutic agents that can be administered with a RBP4-specific modulator or inhibitor include, without limitation, Avandamet (GlaxoSmithKline) a combination of Rosiglitazone and Metformin, Glucovance (Bristol-Myers Squibb) a combination of Metformin and Glyburide, Metaglip (Bristol-Myers Squibb) a combination of Metformin and Glipizide, Duetact (Takeda) a combination of Pioglitazone and Glimepirid, Janumet (Merck) a combination of Sitagliptin and Metformin HCl, or ACTOplus met (Takeda) a combination of Metformin and pioglitazone.

Any of the aforementioned is useful in combination with one or more of the RBP4-specific modulator or inhibitor, such as any antisense inhibitor of RBP4 according to this invention. Combined compounds (two or more) may be used together or sequentially.

Cholesterol-lowering Drugs/Agents/Therapeutics and Triglyceride-Lowering Drugs/Agents/Therapeutics The invention also provides methods of combination therapy, wherein, one or more compounds of the invention and one or more other therapeutic/prophylactic compounds are administered treat a condition and/or disease state. In various aspects, the compound(s) of the invention and the therapeutic/prophylactic compound(s) are co-administered as a mixture or administered separately. In one aspect, the route of administration is the same for the compound(s) of the invention and the therapeutic/prophylactic compound(s), while in other aspects, the compound(s) of the invention and the therapeutic/prophylactic compound(s) are administered by different routes. In one embodiment, the dosages of the compound(s) of the invention and the therapeutic/prophylactic compound(s) are amounts that are therapeutically or prophylactically effective for each compound when administered separately. Alternatively, the combined administration permits use of lower dosages than would be required to achieve a therapeutic or prophylactic effect if administered separately, and such methods are useful in decreasing one or more side effects of the reduced-dose compound.

In one aspect, a compound of the present invention and one or more other therapeutic/prophylactic compound(s) effective at treating a condition are administered wherein, both compounds act through the same or different mechanisms. Therapeutic/prophylactic compound(s) include, but are not limited to, bile salt sequestering resins (e.g., cholestyramine, colestipol, and colesevelam hydrochloride), cholesterol biosynthesis inhibitors, especially HMG CoA reductase inhibitors (such as atorvastatin, pravastatin, simvastatin, lovastatin, fluvastatin, cerivastatin, rosuvastatin, and pitivastatin (itavastatin/risivastatin)), nicotinic acid, fibric acid derivatives (e.g., clofibrate, gemfibrozil, fenofibrate, bezafibrate, and ciprofibrate), probucol, neomycin, dextrothyroxine, plant-stanol esters, cholesterol absorption inhibitors (e.g., ezetimibe and pamaqueside), implitapide, squalene synthetase inhibitors, bile acid sequestrants such as cholestyramine, inhibitors of bile acid transporters (apical sodium-dependent bile acid transporters), regulators of hepatic CYP7a, estrogen replacement therapeutics (e.g., tamoxigen), and anti-inflammatories (e.g., glucocorticoids).

Antisense inhibition of RBP4 is described herein, below to reduce plasma lipids of animals on high-fat diets and may be useful in treatment of cardiovascular disease.

Any of the aforementioned is useful in combination with one or more of the RBP4-specific modulators or inhibitors, such as any antisense inhibitor of RBP4 according to this invention. Combined compounds (two or more) may be used together or sequentially.

Pharmaceutical Compositions and Formulations

Another embodiment includes compositions and formulations for RBP4-specific modulators such as, for example, antisense compounds, as described herein. The RBP4-specific modulators, may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein, by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancer surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P (TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein, by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

RBP4-specific modulators include compositions of, but are not limited to, solutions, emulsions, and liposome-containing formulations. These compositions may be generated from a variety of components that include, but are not limited to, preformed liquids, self-emulsifying solids and self-emulsifying semisolids.

The RBP4-specific modulators, as described herein, include formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions, may be formulated into any of many possible dosage forms such as, but not limited to, tablets, capsules, gel capsules, liquid syrups, soft gels, suppositories, and enemas. The compositions, may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

RBP4-specific modulators may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the agents of the present invention.

Antisense oligonucleotides may be admixed with pharmaceutically acceptable active and/or inert substances for the preparation of pharmaceutical compositions or formulations. Compositions and methods for the formulation of RBP4-specific modulators are dependent upon a number of criteria, including, but not limited to, route of administration, extent of disease, or dose to be administered.

Antisense compound targeted to a RBP4 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment employed in the methods described herein, is a pharmaceutical composition comprising a RBP4-specific antisense compound a RBP4-specific antisense compound and a pharmaceutically acceptable diluent. In one embodiment, the pharmaceutically acceptable diluent is PBS. In other embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

In certain embodiments, pharmaceutical compositions comprise one or more oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a RBP4-specific modulator is prepared using known techniques, including, but not limited to, mixing, dissolving, granulating, dragee-making, levigating, emulsifying, encapsulating, entrapping or tabletting processes.

In certain embodiments, a RBP4-specific modulator is a liquid (e.g., a suspension, elixir and/or solution). In certain of such embodiments, a liquid RBP4-specific modulator is prepared using ingredients known in the art, including, but not limited to, water, glycols, oils, alcohols, flavoring agents, preservatives, and coloring agents.

In certain embodiments, a RBP4-specific modulator is a solid (e.g., a powder, tablet, and/or capsule). In certain of such embodiments, a solid RBP4-specific modulator comprising one or more oligonucleotides is prepared using ingredients known in the art, including, but not limited to, starches, sugars, diluents, granulating agents, lubricants, binders, and disintegrating agents.

In certain embodiments, a RBP4-specific modulator is formulated as a depot preparation. Certain such depot preparations are typically longer acting than non-depot preparations. In certain embodiments, such preparations are administered by implantation (e.g., subcutaneously or intravenously) or by intramuscular injection. In certain embodiments, depot preparations are prepared using suitable polymeric or hydrophobic materials (e.g., an emulsion in an acceptable oil) or ion exchange resins, or as sparingly soluble derivatives, for example, as a sparingly soluble salt.

In certain embodiments, a RBP4-specific modulator comprises a delivery system. Examples of delivery systems include, but are not limited to, liposomes and emulsions. Certain delivery systems are useful for preparing certain RBP4-specific modulators, including those comprising hydrophobic compounds. In certain embodiments, certain organic solvents such as dimethylsulfoxide are used.

In certain embodiments, a RBP4-specific modulator comprises one or more tissue-specific delivery molecules designed to deliver the one or more RBP4-specific modulators to specific tissues or cell types. For example, in certain embodiments, RBP4-specific modulators include liposomes coated with a tissue-specific antibody.

In certain embodiments, a RBP4-specific modulator comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied; for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a RBP4-specific modulator comprises a sustained-release system. A non-limiting example of such a sustained-release system is a semi-permeable matrix of solid hydrophobic polymers. In certain embodiments, sustained-release systems may, depending on their chemical nature, release RBP4-specific modulators over a period of hours, days, weeks or months.

In certain embodiments, a RBP4-specific modulator is prepared for oral administration. In certain of such embodiments, a RBP4-specific modulator is formulated by combining one or more oligonucleotides with one or more pharmaceutically acceptable carriers. Certain of such carriers enable RBP4-specific modulators to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, RBP4-specific modulators for oral administration are push-fit capsules made of gelatin. Certain of such push-fit capsules comprise one or more RBP4-specific modulators in admixture with one or more fillers, such as lactose, binders, such as starches, and/or lubricants, such as talc or magnesium stearate and, optionally, stabilizers. In certain embodiments, RBP4-specific modulators for oral administration are soft, sealed capsules made of gelatin and a plasticizer, such as glycerol or sorbitol. In certain soft capsules, one or more RBP4-specific modulators are be dissolved or suspended in suitable liquids, such as fatty oils, liquid paraffin, or liquid polyethylene glycols. In addition, stabilizers may be added.

In certain embodiments, RBP4-specific modulators are prepared for buccal administration. Certain of such RBP4-specific modulators are tablets or lozenges formulated in conventional manner.

In certain embodiments, a RBP4-specific modulator is prepared for administration by injection (e.g., intravenous, subcutaneous, intramuscular, etc.). In certain of such embodiments, a RBP4-specific modulator comprises a carrier and is formulated in aqueous solution, such as water, or physiologically compatible buffers, such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain RBP4-specific modulators for injection are presented in unit dosage form, for example, in ampules or in multi-dose containers. Certain RBP4-specific modulators for injection are suspensions, solutions or emulsions in oily or aqueous vehicles, and may contain formulatory agents such as suspending, stabilizing and/or dispersing agents. Certain solvents suitable for use in RBP4-specific modulators for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the RBP4-specific modulators to allow for the preparation of highly concentrated solutions.

In certain embodiments, a RBP4-specific modulator is prepared for transmucosal administration. In certain of such embodiments, penetrants appropriate to the barrier to be permeated are used in the formulation. Such penetrants are generally known in the art.

In certain embodiments, a RBP4-specific modulator is prepared for administration by inhalation. Certain of such RBP4-specific modulators for inhalation are prepared in the form of an aerosol spray in a pressurized pack or a nebulizer. Certain of such RBP4-specific modulators comprise a propellant, for example, dichlorodifluoromethane, trichlorofluoromethane, dichlorotetrafluoroethane, carbon dioxide or other suitable gas. In certain embodiments, using a pressurized aerosol, the dosage unit may be determined with a valve that delivers a metered amount. In certain embodiments, capsules and cartridges for use in an inhaler or insufflator may be formulated. Certain of such formulations comprise a powder mixture of a RBP4-specific modulator of the invention and a suitable powder base, such as lactose or starch.

In certain embodiments, a RBP4-specific modulator is prepared for rectal administration, such as a suppositories or retention enema. Certain of such RBP4-specific modulators comprise known ingredients, such as cocoa butter and/or other glycerides.

In certain embodiments, a RBP4-specific modulator is prepared for topical administration. Certain of such pharmaceutical compositions comprise bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.).

In certain embodiments, a RBP4-specific modulator comprises an oligonucleotide in a therapeutically effective amount, as described herein. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more oligonucleotides is formulated as a prodrug. In certain embodiments, upon in vivo administration, a prodrug is chemically converted to the biologically, pharmaceutically or therapeutically more active form of the oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances, the carboxylic acid-containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

In certain embodiments, a pharmaceutical composition comprising one or more RBP4-specific modulators is useful for treating conditions or disorders in a mammalian, and particularly, in a human, subject. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., in the renal or cardiac area).

In certain embodiments, a pharmaceutical composition is administered in the form of a dosage unit (e.g., tablet, capsule, bolus, etc.). In certain embodiments, such pharmaceutical compositions comprise an oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition comprises a dose of oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg. In certain embodiments, a pharmaceutical composition comprises a dose of oligonucleotide selected from 50 mg, 100 mg, 150 mg, 200 mg, 250 mg, 300 mg, and 400 mg. In certain embodiments, the dose is administered at intervals ranging from more than once per day, once per day, once per week, twice per week, three times per week, four times per week, five times per week, 6 times per week, once per month to once per three months, for as long as needed to sustain the desired effect.

In a further aspect, a RBP4-specific modulator is a sterile-lyophilized oligonucleotide that is reconstituted with a suitable diluent, for example, sterile water for injection. The reconstituted product is administered as a subcutaneous injection or as an intravenous infusion after dilution into saline. The lyophilized drug product consists of the oligonucleotide which has been prepared in water for injection, adjusted to pH 7.0-9.0 with acid or base during preparation, and then lyophilized. The lyophilized oligonucleotide may be 25-800 mg of the oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of lyophilized oligonucleotide. The lyophilized drug product may be packaged in a 2 mL Type I, clear glass vial (ammonium sulfate-treated), stoppered with a bromobutyl rubber closure and sealed with an aluminum FLIP-OFF® overseal.

The compositions may additionally contain other adjunct components conventionally found in pharmaceutical compositions, at their art-established usage levels. Thus, for example, the compositions may contain additional, compatible, pharmaceutically-active materials, such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, for example, lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation Salts, Prodrugs and Bioequivalents The RBP4-specific modulators of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes or other chemicals and/or conditions. In particular, prodrug versions of the oligonucleotides of the invention are prepared as SATE ((S-acetyl-2-thioethyl) phosphate) derivatives according to the methods described in International Patent Application Publication No. WO 93/24510, published Dec. 9, 1993; and International Patent Application Publication No. WO 94/26764, and U.S. Pat. No. 5,770,713.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, examples of pharmaceutically acceptable salts and their uses are further described in U.S. Pat. No. 6,287,860, which is incorporated herein, in its entirety.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic and inorganic acid salts of the amines. Acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic—acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoc acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides or antisense compounds, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. Sodium salts of antisense oligonucleotides are useful and are well accepted for therapeutic administration to humans. In another embodiment, sodium salts of dsRNA compounds are also provided.

Excipients

In contrast to RBP4-specific modulators that are carrier compounds, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administrations which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Also provided herein, where appropriate, methods as provided herein can be performed both in vitro and/or in vivo.

While the present invention has been described with specificity in accordance with certain embodiments, the following examples serve only to illustrate the invention and are not intended to limit the same.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

The in vivo studies provided herein below are carried out in well characterized models of disease that are recognized by those of skill in the art as being predictive of therapeutic results in other animals, including humans.

Example 1

Antisense Inhibition of Mouse RBP4: Primary Hepatocytes

Antisense oligonucleotides targeted to a RBP4 nucleic acid were tested for their effects on RBP4 mRNA in vitro. Cultured primary mouse hepatocytes were transfected using lipofectin reagent with 70 nM antisense oligonucleotide for 4 hours. After a recovery period of approximately 24 hours, RNA was isolated from the cells and RBP4 mRNA levels were measured by quantitative real-time PCR. RBP4 mRNA levels were adjusted according to total RNA content, as measured by RIBOGREEN®. Results are presented as percent inhibition of RBP4, relative to untreated control cells.

The chimeric antisense oligonucleotides in Table 1 were designed as 5-10-5 MOE gapmers. The gapmers are 20 nucleotides in length, wherein the central gap segment is comprised of 10 2'-deoxynucleotides and is flanked on both sides (in the 5' and 3' directions) by wings comprising 5 nucleotides each. Each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines. "Mouse target start site" indicates the 5'-most nucleotide to which the gapmer is targeted in the mouse sequence. "Mouse target stop site" indicates the 3'-most nucleotide to which the gapmer is targeted in the mouse sequence. Each gapmer listed in Table 1 is targeted to mouse target sequence (GenBank accession number NM_011255.2, incorporated herein as SEQ ID NO: 1; GenBank accession number AK004839.1, incorporated herein as SEQ ID NO: 3; and the complement of residues 31300000_31311000 of GenBank accession number NT_039687.6, representing a partial genomic sequence of RBP4, incorporated herein as SEQ ID NO: 2).

The mouse oligonucleotides also show cross reactivity (i.e. <3 base mismatch) with the human RBP4 mRNA (GEN-BANK Accession No. NM_006744.3), incorporated herein as SEQ ID NO: 5. "Human Target Start Site" indicates the 5'-most nucleotide in the human mRNA to which the antisense oligonucleotide is targeted. "Human Target Stop Site" indicates the 3'-most nucleotide in the human mRNA to which the antisense oligonucleotide is targeted. 'Mismatches' indicates the number of nucleobases by which the mouse oligonucleotide is mismatched with the human gene sequence. "n/a" indicates that there was no cross-reactivity between the mouse oligonucleotide and the human gene sequence.

TABLE 1

Inhibition of mouse RBP4 mRNA levels by chimeric antisense oligonucleotides having 5-10-5 MOE wings and deoxy gap

| ISIS No. | Mouse Target Start Site | Mouse Target Stop Site | Mouse Target sequence | Sequence (5' to 3') | % inhibition | Human Target Start Site | Human Target Stop Site | Mis-Matches | SEQ ID NO. |
|---|---|---|---|---|---|---|---|---|---|
| 403525 | 128 | 147 | NM_011255.2 | AGCCAGCTGCA GTCTTGGGT | 2 | n/a | n/a | n/a | 6 |
|  | 1395 | 1414 | NT_039687.6_ TRUNC_31300000_ 31311000_COMP |  |  |  |  |  |  |
| 403526 | 136 | 155 | NM_011255.2 | CCAGCGGCAGC CAGCTGCAG | 15 | n/a | n/a | n/a | 7 |
|  | 1403 | 1422 | NT_039687.6_ TRUNC_31300000_ 31311000_COMP |  |  |  |  |  |  |
| 403527 | 1112 | 1131 | NM_011255.2 | GGAATCCCAAG CCTCAAACG | 73 | n/a | n/a | n/a | 8 |
| 403528 | 1119 | 1138 | NM_011255.2 | CAAGTTTGGAA TCCCAAGCC | 71 | n/a | n/a | n/a | 9 |
|  | 9845 | 9864 | NT_039687.6_ TRUNC_31300000_ 31311000_COMP |  |  |  |  |  |  |
| 403529 | 335 | 354 | NM_011255.2 | TCCCAGAGCCG CCAGCAGCA | 35 | 107 | 126 | 3 | 10 |
|  | 1909 | 1928 | NT_039687.6_ TRUNC_31300000_ 31311000_COMP |  |  |  |  |  |  |
|  | 95 | 114 | AK004839.1 |  |  |  |  |  |  |
| 403530 | 369 | 388 | NM_011255.2 | TGCTCACCCTG CAGTCGCGC | 69 | 141 | 160 | 2 | 11 |
|  | 1943 | 1962 | NT_039687.6_ TRUNC_31300000_ 31311000_COMP |  |  |  |  |  |  |
|  | 127 | 146 | AK004839.1 |  |  |  |  |  |  |
| 403531 | 403 | 422 | NM_011255.2 | CGAGCCTTGTC GAAGTTCTC | 66 | 175 | 194 | 0 | 12 |
|  | 1977 | 1996 | NT_039687.6_ TRUNC_31300000_ 31311000_COMP |  |  |  |  |  |  |
|  | 161 | 180 | AK004839.1 |  |  |  |  |  |  |
| 403532 | 408 | 427 | NM_011255.2 | AGAAACGAGCC TTGTCGAAG | 67 | 180 | 199 | 1 | 13 |
|  | 166 | 185 | AK004839.1 |  |  |  |  |  |  |
| 403533 | 413 | 432 | NM_011255.2 | CCCAGAGAAAC GAGCCTTGT | 24 | 185 | 204 | 1 | 14 |
|  | 171 | 190 | AK004839.1 |  |  |  |  |  |  |
| 403534 | 421 | 440 | NM_011255.2 | TACCAGAGCCC AGAGAAACG | 23 | 193 | 212 | 3 | 15 |
|  | 179 | 198 | AK004839.1 |  |  |  |  |  |  |
| 403535 | 426 | 445 | NM_011255.2 | TGGCATACCAG AGCCCAGAG | 49 | 198 | 217 | 3 | 16 |
|  | 2086 | 2105 | NT_039687.6_ TRUNC_31300000_ 31311000_COMP |  |  |  |  |  |  |
|  | 184 | 203 | AK004839.1 |  |  |  |  |  |  |
| 403536 | 431 | 450 | NM_011255.2 | GGCGATGGCAT ACCAGAGCC | 69 | n/a | n/a | n/a | 17 |
|  | 2091 | 2110 | NT_039687.6_ TRUNC_31300000_ 31311000_COMP |  |  |  |  |  |  |
|  | 189 | 208 | AK004839.1 |  |  |  |  |  |  |
| 403537 | 439 | 458 | NM_011255.2 | TCCTTTTTGGC GATGGCATA | 55 | 211 | 230 | 3 | 18 |
|  | 2099 | 2118 | NT_039687.6_ TRUNC_31300000_ 31311000_COMP |  |  |  |  |  |  |
|  | 197 | 216 | AK004839.1 |  |  |  |  |  |  |

TABLE 1-continued

Inhibition of mouse RBP4 mRNA levels by chimeric antisense
oligonucleotides having 5-10-5 MOE wings and deoxy gap

| ISIS No. | Mouse Target Start Site | Mouse Target Stop Site | Mouse Target sequence | Sequence (5' to 3') | % inhibition | Human Target Start Site | Human Target Stop Site | Mis- Matches | SEQ ID NO. |
|---|---|---|---|---|---|---|---|---|---|
| 403538 | 460 2120 218 | 479 2139 237 | NM_011255.2 NT_039687.6_ TRUNC_31300000_ 31311000_COMP AK004839.1 | TGCAAAAAGAG ACCCTCGGG | 90 | 232 | 251 | 2 | 19 |
| 403539 | 465 2125 223 | 484 2144 242 | NM_011255.2 NT_039687.6_ TRUNC_31300000 31311000_COMP AK004839.1 | TGTCTTGCAAA AAGAGACCC | 68 | 237 | 256 | 3 | 20 |
| 403540 | 470 2130 228 | 489 2149 247 | NM_011255.2 NT_039687.6_ TRUNC_31300000_ 31311000_COMP AK004839.1 | GATGTTGTCTT GCAAAAAGA | 49 | 242 | 261 | 2 | 21 |
| 403541 | 475 2135 233 | 494 2154 252 | NM_011255.2 NT_039687.6_ TRUNC_31300000_ 31311000_COMP AK004839.1 | GCGATGATGTT GTCTTGCAA | 86 | 247 | 266 | 3 | 22 |
| 403542 | 480 2140 238 | 499 2159 257 | NM_011255.2 NT_039687.6_ TRUNC_31300000_ 31311000_COMP AK004839.1 | ACTCAGCGATG ATGTTGTCT | 91 | 252 | 271 | 3 | 23 |
| 403543 | 485 2145 243 | 504 2164 262 | NM_011255.2 NT_039687.6_ TRUNC_31300000_ 31311000_COMP AK004839.1 | AGAAAACTCAG CGATGATGT | 75 | n/a | n/a | n/a | 24 |
| 403544 | 490 2150 248 | 509 2169 267 | NM_011255.2 NT_039687.6_ TRUNC_31300000_ 31311000_COMP AK004839.1 | TCCACAGAAAA CTCAGCGAT | 87 | n/a | n/a | n/a | 25 |
| 403545 | 545 303 | 564 322 | NM_011255.2 AK004839.1 | GTTGCTCAGAA GACGGACTC | 39 | 317 | 336 | 3 | 26 |
| 403546 | 550 308 | 569 327 | NM_011255.2 AK004839.1 | TCCCAGTTGCT CAGAAGACG | 4 | 322 | 341 | 3 | 27 |
| 403547 | 555 313 | 574 332 | NM_011255.2 AK004839.1 | ACACTTCCCAG TTGCTCAGA | 54 | n/a | n/a | n/a | 28 |
| 403548 | 560 2380 318 | 579 2399 337 | NM_011255.2 NT_039687.6_ TRUNC_31300000_ 31311000_COMP AK004839.1 | TGCACACACTT CCCAGTTGC | 68 | n/a | n/a | n/a | 29 |
| 403549 | 565 2385 323 | 584 2404 342 | NM_011255.2 NT_039687.6_ TRUNC_31300000_ 31311000_COMP AK004839.1 | ATGTCTGCACA CACTTCCCA | 73 | 337 | 356 | 2 | 30 |
| 403550 | 570 2390 328 | 589 2409 347 | NM_011255.2 NT_039687.6_ TRUNC_31300000_ 31311000_COMP AK004839.1 | CCACCATGTCT GCACACACT | 31 | 342 | 361 | 2 | 31 |

TABLE 1-continued

Inhibition of mouse RBP4 mRNA levels by chimeric antisense
oligonucleotides having 5-10-5 MOE wings and deoxy gap

| ISIS No. | Mouse Target Start Site | Mouse Target Stop Site | Mouse Target sequence | Sequence (5' to 3') | % inhibition | Human Target Start Site | Human Target Stop Site | Mis-Matches | SEQ ID NO. |
|---|---|---|---|---|---|---|---|---|---|
| 403551 | 575 | 594 | NM_011255.2 | AGTGCCCACCA TGTCTGCAC | 49 | 347 | 366 | 2 | 32 |
| | 2395 | 2414 | NT_039687.6_ TRUNC_31300000_ 31311000_COMP | | | | | | |
| | 333 | 352 | AK004839.1 | | | | | | |
| 403552 | 581 | 600 | NM_011255.2 | TGTGAAAGTGC CCACCATGT | 45 | 353 | 372 | 1 | 33 |
| | 2401 | 2420 | NT_039687.6_ TRUNC_31300000_ 31311000_COMP | | | | | | |
| | 339 | 358 | AK004839.1 | | | | | | |
| 403553 | 607 | 626 | NM_011255.2 | TTGAACTTGGC AGGATCTTC | 69 | 379 | 398 | 2 | 34 |
| | 2427 | 2446 | NT_039687.6_ TRUNC_31300000_ 31311000_COMP | | | | | | |
| | 365 | 384 | AK004839.1 | | | | | | |
| 403554 | 613 | 632 | NM_011255.2 | TTCATCTTGAA CTTGGCAGG | 59 | 385 | 404 | 0 | 35 |
| | 2433 | 2452 | NT_039687.6_ TRUNC_31300000_ 31311000_COMP | | | | | | |
| | 371 | 390 | AK004839.1 | | | | | | |
| 403555 | 621 | 640 | NM_011255.2 | CCCAGTACTTC ATCTTGAAC | 67 | 393 | 412 | 0 | 36 |
| | 2441 | 2460 | NT_039687.6_ TRUNC_31300000_ 31311000_COMP | | | | | | |
| | 379 | 398 | AK004839.1 | | | | | | |
| 403556 | 627 | 646 | NM_011255.2 | CTACACCCCAG TACTTCATC | 14 | 399 | 418 | 1 | 37 |
| | 2447 | 2466 | NT_039687.6_ TRUNC_31300000_ 31311000_COMP | | | | | | |
| | 385 | 404 | AK004839.1 | | | | | | |
| 403557 | 632 | 651 | NM_011255.2 | GGAGGCTACAC CCCAGTACT | 42 | 404 | 423 | 1 | 38 |
| | 2452 | 2471 | NT_039687.6_ TRUNC_31300000_ 31311000_COMP | | | | | | |
| | 390 | 409 | AK004839.1 | | | | | | |
| 403558 | 637 | 656 | NM_011255.2 | AGAAAGGAGGC TACACCCCA | 54 | 409 | 428 | 1 | 39 |
| | 2457 | 2476 | NT_039687.6_ TRUNC_31300000_ 31311000_COMP | | | | | | |
| | 395 | 414 | AK004839.1 | | | | | | |
| 403559 | 642 | 661 | NM_011255.2 | GCTGGAGAAAG GAGGCTACA | 11 | 414 | 433 | 2 | 40 |
| | 2462 | 2481 | NT_039687.6_ TRUNC_31300000_ 31311000_COMP | | | | | | |
| | 400 | 419 | AK004839.1 | | | | | | |
| 403560 | 651 | 670 | NM_011255.2 | CGTTTCCTCGC TGGAGAAAG | 22 | 423 | 442 | 3 | 41 |
| | 409 | 428 | AK004839.1 | | | | | | |
| 403561 | 669 | 688 | NM_011255.2 | CGATGATCCAG TGGTCATCG | 40 | 441 | 460 | 2 | 42 |
| | 8033 | 8052 | NT_039687.6_ TRUNC_31300000_ 31311000_COMP | | | | | | |
| | 427 | 446 | AK004839.1 | | | | | | |
| 403562 | 699 | 718 | NM_011255.2 | ACTGCAGAGCG AAGGTGTCG | 0 | n/a | n/a | n/a | 43 |
| | 8063 | 8082 | NT_039687.6_ TRUNC_31300000_ 31311000_COMP | | | | | | |
| | 457 | 476 | AK004839.1 | | | | | | |

TABLE 1-continued

Inhibition of mouse RBP4 mRNA levels by chimeric antisense oligonucleotides having 5-10-5 MOE wings and deoxy gap

| ISIS No. | Mouse Target Start Site | Mouse Target Stop Site | Mouse Target sequence | Sequence (5' to 3') | % inhibition | Human Target Start Site | Human Target Stop Site | Mis-Matches | SEQ ID NO. |
|---|---|---|---|---|---|---|---|---|---|
| 403563 | 721 | 740 | NM_011255.2 | AGATTCTGCAG GCGGCAGGA | 81 | 493 | 512 | 3 | 44 |
|  | 8085 | 8104 | NT_039687.6_TRUNC_31300000_31311000_COMP |  |  |  |  |  |  |
|  | 479 | 498 | AK004839.1 |  |  |  |  |  |  |
| 403564 | 727 | 746 | NM_011255.2 | CCATCCAGATT CTGCAGGCG | 30 | n/a | n/a | n/a | 45 |
|  | 8091 | 8110 | NT_039687.6_TRUNC_31300000_31311000_COMP |  |  |  |  |  |  |
|  | 485 | 504 | AK004839.1 |  |  |  |  |  |  |
| 403565 | 736 | 755 | NM_011255.2 | GCACAGGTGCC ATCCAGATT | 51 | 508 | 527 | 2 | 46 |
|  | 8100 | 8119 | NT_039687.6_TRUNC_31300000_31311000_COMP |  |  |  |  |  |  |
|  | 494 | 513 | AK004839.1 |  |  |  |  |  |  |
| 403566 | 741 | 760 | NM_011255.2 | TGTCTGCACAG GTGCCATCC | 50 | 513 | 532 | 2 | 47 |
|  | 8105 | 8124 | NT_039687.6_TRUNC_31300000_31311000_COMP |  |  |  |  |  |  |
|  | 499 | 518 | AK004839.1 |  |  |  |  |  |  |
| 403567 | 874 | 893 | NM_011255.2 | CTTTGACAGTA ACCATTGTG | 64 | n/a | n/a | n/a | 48 |
|  | 632 | 651 | AK004839.1 |  |  |  |  |  |  |
| 403568 | 922 | 941 | NM_011255.2 | CAAACTTCACA TCCTAGACG | 57 | n/a | n/a | n/a | 49 |
|  | 9648 | 9667 | NT_039687.6_TRUNC_31300000_31311000_COMP |  |  |  |  |  |  |
|  | 680 | 699 | AK004839.1 |  |  |  |  |  |  |
| 403569 | 932 | 951 | NM_011255.2 | CAGAAATCTTC AAACTTCAC | 36 | n/a | n/a | n/a | 50 |
|  | 9658 | 9677 | NT_039687.6_TRUNC_31300000_31311000_COMP |  |  |  |  |  |  |
|  | 690 | 709 | AK004839.1 |  |  |  |  |  |  |
| 403570 | 942 | 961 | NM_011255.2 | GAAAGCTAATC AGAAATCTT | 65 | n/a | n/a | n/a | 51 |
|  | 9668 | 9687 | NT_039687.6_TRUNC_31300000_31311000_COMP |  |  |  |  |  |  |
|  | 700 | 719 | AK004839.1 |  |  |  |  |  |  |
| 403571 | 950 | 969 | NM_011255.2 | GACCGGATGAA AGCTAATCA | 68 | n/a | n/a | n/a | 52 |
|  | 9676 | 9695 | NT_039687.6_TRUNC_31300000_31311000_COMP |  |  |  |  |  |  |
|  | 708 | 727 | AK004839.1 |  |  |  |  |  |  |
| 403572 | 964 | 983 | NM_011255.2 | TAAATAGAGAT GAAGACCGG | 48 | 735 | 754 | 3 | 53 |
|  | 9690 | 9709 | NT_039687.6_TRUNC_31300000_31311000_COMP |  |  |  |  |  |  |
|  | 722 | 741 | AK004839.1 |  |  |  |  |  |  |
| 403573 | 972 | 991 | NM_011255.2 | TTCTAAGATAA ATAGAGATG | 28 | 743 | 762 | 2 | 54 |
|  | 9698 | 9717 | NT_039687.6_TRUNC_31300000_31311000_COMP |  |  |  |  |  |  |
|  | 730 | 749 | AK004839.1 |  |  |  |  |  |  |
| 403574 | 1017 | 1036 | NM_011255.2 | TTAATGTCCAC CTAGAGAAG | 40 | n/a | n/a | n/a | 55 |
|  | 9743 | 9762 | NT_039687.6_TRUNC_31300000_31311000_COMP |  |  |  |  |  |  |
|  | 775 | 794 | AK004839.1 |  |  |  |  |  |  |

TABLE 1-continued

Inhibition of mouse RBP4 mRNA levels by chimeric antisense oligonucleotides having 5-10-5 MOE wings and deoxy gap

| ISIS No. | Mouse Target Start Site | Mouse Target Stop Site | Mouse Target sequence | Sequence (5' to 3') | % inhibition | Human Target Start Site | Human Target Stop Site | Mis-Matches | SEQ ID NO. |
|---|---|---|---|---|---|---|---|---|---|
| 403575 | 1028 9754 786 | 1047 9773 805 | NM_011255.2 NT_039687.6_ TRUNC_31300000_ 31311000_COMP AK004839.1 | TGGACGATGGT TTAATGTCC | 17 | n/a | n/a | n/a | 56 |
| 403576 | 1040 798 | 1059 817 | NM_011255.2 AK004839.1 | TCTCATGTACC TTGGACGAT | 71 | n/a | n/a | n/a | 57 |
| 403577 | 1049 807 | 1068 826 | NM_011255.2 AK004839.1 | GTCAGTGACTC TCATGTACC | 65 | n/a | n/a | n/a | 58 |
| 403578 | 1067 9793 825 | 1086 9812 844 | NM_011255.2 NT_039687.6_ TRUNC_31300000_ 31311000_COMP AK004839.1 | TACAGTTGTGT GAACAGAGT | 75 | n/a | n/a | n/a | 59 |
| 403579 | 1079 9805 837 | 1098 9824 856 | NM_011255.2 NT_039687.6_ TRUNC_31300000_ 31311000_COMP AK004839.1 | TTCAGTAAGAC ATACAGTTG | 59 | n/a | n/a | n/a | 60 |
| 403580 | 1092 850 | 1111 869 | NM_011255.2 AK004839.1 | TCCTTCAGGGA CCTTCAGTA | 30 | n/a | n/a | n/a | 61 |
| 403581 | 1106 | 1125 | NM_011255.2 AK004839.1 | CCAAGCCTCAA ACATCCTTC | 60 | n/a | n/a | n/a | 62 |
| 403582 | 879 | 898 | AK004839.1 | CCAAGTTTGGA TACCCCAAG | 70 | n/a | n/a | n/a | 63 |
| 403583 | 894 | 913 | AK004839.1 | CTATATGTTAA TAACCCAAG | 63 | n/a | n/a | n/a | 64 |
| 403584 | 901 | 920 | AK004839.1 | GATGTCACTAT ATGTTAATA | 49 | n/a | n/a | n/a | 65 |
| 403585 | 1216 | 1235 | NT_039687.6_ TRUNC_31300000_ 31311000_COMP | GAGAAGCTTTT TGGCATATT | 44 | n/a | n/a | n/a | 66 |
| 403586 | 1254 | 1273 | NT_039687.6_ TRUNC_31300000_ 31311000_COMP | TTCCCAAGTGG CCCCTGCTT | 20 | n/a | n/a | n/a | 67 |
| 403587 | 21 1288 | 40 1307 | NM_011255.2 NT_039687.6_ TRUNC_31300000_ 31311000_COMP | TGTAGCCTGGA ACATTAGCG | 0 | n/a | n/a | n/a | 68 |
| 403588 | 39 1306 | 58 1325 | NM_011255.2 NT_039687.6_ TRUNC_31300000_ 31311000_COMP | GCGAAAAGGGA CCTATGATG | 22 | n/a | n/a | n/a | 69 |
| 403589 | 57 1324 | 76 1343 | NM_011255.2 NT_039687.6_ TRUNC_31300000_ 31311000_COMP | TGATGGTGGCC TCACTGAGC | 65 | n/a | n/a | n/a | 70 |
| 403590 | 127 | 146 | NM_011255.2 | GTCAGCTGCAG TCTTGGGTG | 25 | n/a | n/a | n/a | 71 |
| 403591 | 177 1444 | 196 1463 | NM_011255.2 NT_039687.6_ TRUNC_31300000_ 31311000_COMP | AGCCCAGAGGA TCCATCGGG | 19 | n/a | n/a | n/a | 72 |

TABLE 1-continued

Inhibition of mouse RBP4 mRNA levels by chimeric antisense oligonucleotides having 5-10-5 MOE wings and deoxy gap

| ISIS No. | Mouse Target Start Site | Mouse Target Stop Site | Mouse Target sequence | Sequence (5' to 3') | % inhibition | Human Target Start Site | Human Target Stop Site | Mis-Matches | SEQ ID NO. |
|---|---|---|---|---|---|---|---|---|---|
| 403592 | 250 1517 | 269 1536 | NM_011255.2 NT_039687.6_ TRUNC_31300000_ 31311000_COMP | GTCAGCCTTGC CGTCCCACG | 14 | n/a | n/a | n/a | 73 |
| 403593 | 1749 | 1768 | NT_039687.6_ TRUNC_31300000_ 31311000_COMP | GGCGGCTCACC AGCAGGAGC | 26 | n/a | n/a | n/a | 74 |
| 403594 | 2211 | 2230 | NT_039687.6_ TRUNC_31300000_ 31311000_COMP | GGCCACTGACC TCAGAAGAC | 59 | n/a | n/a | n/a | 75 |
| 403595 | 3023 | 3042 | NT_039687.6_ TRUNC_31300000_ 31311000_COMP | TAGCTTTCGGA TCTATAATT | 36 | n/a | n/a | n/a | 76 |
| 403596 | 5532 | 5551 | NT_039687.6_ TRUNC_31300000_ 31311000_COMP | TGGTTTCAAAT GTTCAACAG | 38 | n/a | n/a | n/a | 77 |
| 403597 | 5657 | 5676 | NT_039687.6_ TRUNC_31300000_ 31311000_COMP | GTGCCTGAGGC AGAGACTAT | 36 | n/a | n/a | n/a | 78 |
| 403598 | 7535 | 7554 | NT_039687.6_ TRUNC_31300000_ 31311000_COMP | GTGGGCTAGAG GATGCCAAT | 68 | n/a | n/a | n/a | 79 |
| 403599 | 8235 | 8254 | NT_039687.6_ TRUNC_31300000_ 31311000_COMP | ACTTGCTCACC ATTGTGTTC | 62 | n/a | n/a | n/a | 80 |
| 403600 | 9102 | 9121 | NT_039687.6_ TRUNC_31300000_ 31311000_COMP | CTCACTGGTGG AGTATGTAT | 15 | n/a | n/a | n/a | 81 |
| 403601 | 9381 | 9400 | NT_039687.6_ TRUNC_31300000_ 31311000_COMP | ATGAGTCACTA TCCATTTAT | 47 | n/a | n/a | n/a | 82 |
| 403602 | 9597 | 9616 | NT_039687.6_ TRUNC_31300000_ 31311000_COMP | TGACAGTAACC TGAAATACA | 67 | n/a | n/a | n/a | 83 |

Example 2

Antisense Inhibition of RBP4 in Mouse Primary Hepatocytes: A Dose Response Experiment Antisense oligonucleotides targeted to RBP4 were tested at various doses in primary mouse hepatocytes. Cells were plated at densities of 10,000 cells per well and treated with nM concentrations of antisense oligonucleotide, as indicated in Table 2. Cultured primary mouse hepatocytes were transfected using lipofectin reagent with 70 nM antisense oligonucleotide for 4 hours. After a recovery period of approximately 24 hours, RNA was isolated from the cells and RBP4 mRNA levels were measured by quantitative real-time PCR. RBP4 mRNA levels were adjusted according to total RNA content, as measured by RIBOGREEN®. Results are presented as percent inhibition of RBP4, relative to untreated control cells. As illustrated in Table 2, RBP4 mRNA levels were reduced in a dose-dependent manner.

TABLE 2

Percent inhibition of RBP4 expression relative to control cells

| ISIS No. | SEQ ID No: | 6.25 nM | 12.5 nM | 25 nM | 50 nM | 100 nM | 200 nM |
|---|---|---|---|---|---|---|---|
| 403527 | 8 | 13.5 | 21.2 | 42.3 | 63.0 | 82.1 | 93.3 |
| 403536 | 17 | 13.3 | 15.2 | 38.3 | 48.5 | 71.8 | 86.3 |
| 403578 | 59 | 0.0 | 10.1 | 26.2 | 41.6 | 73.8 | 90.7 |

As shown in Table 2, percent inhibition of RBP4 expression in mouse primary hepatocytes is dose dependant. Treatment with at least 100 nM of the RBP4 specific oligonucleotide significantly decreased RBP4 expression relative to the control cells.

This indicates that significant inhibition of RBP4 expression can be achieved by administration of an antisense oligonucleotide targeting RBP4.

Example 3

Antisense Inhibition of RBP4 in Lean Mouse Model

Treatment

To evaluate the effects of RBP4 antisense inhibition on RBP4 mRNA levels in vivo, ISIS 403527, ISIS 403536, and ISIS 403578 were evaluated in normal male BALB/C mice maintained on a 12-hour light/dark cycle and fed ad libitum normal Purina mouse chow. Treatment groups (5 mice per group) were as follows: a group treated with ISIS 403527; a group treated with ISIS 403536; and a group treated with ISIS 403578; a control group treated with saline; and a control group treated with an oligonucleotide not complementary to any known gene sequence (ISIS 141923). Oligonucleotides or saline were administered intraperitoneally twice weekly for a period of 3 weeks; oligonucleotide doses were 50 mg/kg. After the treatment period, whole liver and white adipose tissue was collected for RNA analyses.

The saline-injected group served as the control group to which the oligonucleotide-treated groups were compared.

RNA Analysis

Liver and white adipose tissue RNA was isolated for real-time RT-PCR analysis of RBP4. RNA was extracted using a commercially available kit with DNAase digestion (QIAGEN RNeasy Kit; QIAGEN). RBP mRNA levels was measured with quantitative RT-PCR with custom-made RT-PCR enzymes and reagents kit (Invitrogen Life Technology Inc., Carlsbad, Calif.), primer & probe sets designed with Primer Express Software (PE Applied Bioscience, Foster city, CA) and ABI prism 7700 Sequence Detector (PE Applied Biosciences, Foster City, Calif.).

Antisense oligonucleotides distribute to both liver and fat allowing for the reduction of RBP4 expression in both tissues. Liver mRNA of RBP4 expression was significantly reduced in RBP4 antisense oligonucleotide treated mice compared to the control mice. Treatment with ISIS 403527 resulted in an 87% reduction in liver RBP4 mRNA levels; treatment with ISIS 403536 resulted in a 72% reduction in liver RBP4 mRNA levels; and treatment with ISIS 403578 resulted in a 72% reduction in liver RBP4 mRNA levels. WAT mRNA expression of RBP4 was also reduced in the RBP4 antisense oligonucleotide treated mice compared to the control mice. In WAT, treatment with ISIS 403527 resulted in an 89% reduction in WAT RBP4 mRNA levels; treatment with ISIS 403536 resulted in a 47% reduction in WAT RBP4 mRNA levels; and treatment with ISIS 403578 resulted in a 63% reduction in WAT RBP4 mRNA levels (Table 3). ISIS 141923 (CCTTC-CCTGAAGGTTCCTCC, SEQ ID NO: 4) was used as a second control. In this experiment, the control oligonucleotide ISIS 141923 exhibited inhibition in WAT but not in liver. This inhibitory activity of the control oligonucleotide in WAT was not observed in a subsequent experiment (Table 5a). The RBP4 specific antisense oligonucleotides are expected to have a more highly significant reduction of RBP4 mRNA levels due to their specific nature, as demonstrated in Tables 3 and 5a.

TABLE 3

Percent inhibition of RBP4 in mouse lean model relative to saline control

|  | Liver | WAT |
| --- | --- | --- |
| Saline | 0.0 | 0.0 |
| ISIS 141923 | 0.0 | 41.2 |

TABLE 3-continued

Percent inhibition of RBP4 in mouse lean model relative to saline control

|  | Liver | WAT |
| --- | --- | --- |
| ISIS 403527 | 87.5 | 89.6 |
| ISIS 403536 | 71.9 | 47.5 |
| ISIS 403578 | 72.2 | 63.0 |

Measurement of Plasma Transaminase Levels

Elevated levels of plasma transaminases are often used clinically as potential indicators of liver damage. To evaluate the impact of ISIS 403527, 403536 and 403578 on hepatic function of mice described above, plasma concentrations of transaminases were measured using an automated clinical chemistry analyzer (Hitachi Olympus AU400e, Melville, N.Y.). Measurements of alanine transaminase (ALT), aspartate transaminase (AST) and bilirubin were taken after antisense oligonucleotide treatment, and are shown in Table 4. Bilirubin and transaminase levels are considered accurate markers of hepatic toxicity. Bilirubin levels were not affected by antisense oligonucleotide treatment neither were the transaminase levels, as seen by not having an increase more than 3 fold relative to the saline control levels.

TABLE 4

Effect of antisense inhibition on plasma transaminases and Bilirubin levels

|  | ALT (IU/L) | AST (IU/L) | Bilirubin (mg/dL) |
| --- | --- | --- | --- |
| Saline | 32.4 | 66.4 | 0.20 |
| ISIS 141923 | 33.5 | 67.2 | 0.24 |
| ISIS 403527 | 43.4 | 85.4 | 0.22 |
| ISIS 403536 | 33.8 | 52.4 | 0.2 |
| ISIS 403578 | 45.5 | 130.6 | 0.26 |

Together, these gene expression and transaminase concentration studies reveal that ISIS 403527, ISIS 403536, and ISIS 403578 can specifically inhibit RBP4 gene expression without any hepatic toxicity.

These gene and protein expression studies reveal that antisense oligonucleotides can specifically inhibit RBP4 gene expression in hepatic and adipose tissues in lean models. Treatment with an antisense inhibitor of RBP4 reduced RBP4 mRNA levels in both adipose tissue and liver tissue. Thus, antisense inhibitors of RBP4 are candidate therapeutic agents for the treatment of disorders characterized by overexpression of RBP4 in adipose and/or liver tissues such as diabetes, obesity, dyslipidemia, and cardiovascular diseases.

Example 4

Effects of Antisense Inhibition of RBP4 in the ob/ob Mouse Model of Obesity

Treatment

Leptin is a hormone produced by fat that regulates appetite. Deficiency of this hormone in both humans and in non-human animals, leads to obesity. ob/ob mice have a mutation in the leptin gene which results in obesity and hyperglycemia. As such, these mice are a useful model for the investigation of obesity and diabetes and related conditions provided herein. This mouse model is also useful for testing compounds, compositions and methods designed to treat, prevent or ameliorate such conditions.

In accordance with the present invention, the effects of antisense inhibition of RBP4 were investigated in the ob/ob mouse model of obesity. Male ob/ob (C57Bl/6J-Lep$^{ob}$/Lep$^{ob}$) mice at 7 weeks of age were purchased from Jackson Laboratories (Bar Harbor, Me.). During a 1 week acclimation period and throughout the study, mice were fed a diet with a fat content of 10-15% (Labdiets #5015, Purina, St. Louis, Mo.). Treatment groups (9 mice each) were as follows: a group treated with ISIS 403527, a control group treated with saline, and a control group treated with ISIS 141923. Oligonucleotide or saline was administered intraperitoneally twice weekly, for a period of 5 weeks; oligonucleotide doses were 25 mg/kg. After the treatment period, whole liver and white adipose tissue was collected for RNA analyses.

Measurement of RBP4 mRNA Expression

ISIS 403527 inhibited RBP4 mRNA expression in the liver by 90% and in the white adipose tissue by 97% compared to saline control mice as shown in Table 5a.

TABLE 5a

Percent inhibition of RBP4 mRNA in the WAT and Liver tissue relative to saline control

|  | Liver | WAT |
|---|---|---|
| saline | 0.0 | 0.0 |
| ISIS 141923 | 12.7 | 0.0 |
| ISIS 403527 | 90.1 | 97.4 |

Measurement of RBP4 Protein Expression

The reduction of RBP4 (protein) levels in the plasma was also monitored and is given in Table 5b.

TABLE 5B

Percent inhibition of RBP4 protein in the plasma relative to saline control

|  | Week | | |
|---|---|---|---|
|  | 2 | 4 | 5 |
| saline | 0.0 | 0.0 | 0.0 |
| ISIS 141923 | 0.0 | 0.0 | 7.6 |
| ISIS 403527 | 83.4 | 84.7 | 92.4 |

ISIS 403527 was, therefore, able to inhibit RBP4 expression in the ob/ob mice similar to that seen in lean mice, and is a candidate therapeutic agent for the treatment of disorders characterized by RBP4 expression in white adipose and liver tissues.

Together, these gene and protein expression studies reveal that antisense oligonucleotides can specifically inhibit RBP4 gene expression in liver and WAT tissues, which results in reduction of RBP4 protein levels in plasma. Thus, antisense inhibitors of RBP4 are candidate therapeutic agents for the treatment of disorders characterized by RBP4 overexpression in adipose and liver tissues such as diabetes, obesity, dyslipidemia, and cardiovascular diseases.

Example 5

Effects of Antisense Inhibition of RBP4 in the ob/ob Mouse Model of Obesity on Plasma Glucose and Insulin Levels Plasma glucose in mice treated, as described in Example 4, was determined using an automated clinical chemistry analyzer (Hitachi Olympus AU400e, Melville, N.Y.). Plasma insulin levels were determined using a ELISA kit from ALPCO Diagnostics. The results are shown in Table 6 and 7, illustrating changes in fed and fasted plasma glucose and insulin levels at weeks 0, 2 and 4.

TABLE 6

Effect of antisense oligonucleotides on plasma glucose levels (mg/dL)

|  | 0 week - fed | 2 weeks - fed | 4 weeks - 5 h fasted |
|---|---|---|---|
| saline | 504.6 | 725.9 | 500.4 |
| ISIS 141923 | 505.7 | 706.0 | 458.0 |
| ISIS 403527 | 500.3 | 511.1 | 319.0 |

TABLE 7

Effect of antisense oligonucleotides on plasma insulin levels (ng/mL)

|  | 0 week - fed | 2 weeks - fed | 4 weeks - 5 h fasted |
|---|---|---|---|
| saline | 30.9 | 29.0 | 27.1 |
| ISIS 141923 | 33.6 | 32.3 | 21.3 |
| ISIS 403527 | 31.3 | 27.6 | 13.8 |

In ob/ob mice, treatment with RBP4 antisense oligonucleotides led to a 30% reduction in fed plasma glucose levels only after 2 weeks and 36% reduction in fasted plasma glucose levels after 4 weeks treatment. Treatment with the RBP4 antisense oligonucleotides also led to a 49% reduction in fasted insulin levels after 4 weeks. This data indicates that reduction of RBP4 caused an improvement in insulin sensitivity and lowering of circulating glucose levels.

Example 6

Effects of Antisense Inhibition of RBP4 in the ob/ob Mouse Model of Obesity on Glucose Tolerance Glucose tolerance in mice treated, as described in Example 3, was measured. These animals were hyperglycemic. The mice were fasted overnight and then an intraperitoneal injection of glucose at 0.75 g/kg was given. Blood glucose and insulin levels were measured before the glucose challenge and at different time points after challenge up to 90 min as seen in Tables 8 and 9. A spike in glucose tolerance and reduction in glucose levels at the beginning of the assay can often be related to the hyperglycemic nature of the model.

TABLE 8

Effect of antisense oligonucleotides on glucose tolerance (mg/dL)

|  | 0 min | 30 min | 60 min | 90 min |
|---|---|---|---|---|
| saline | 102.2 | 466.1 | 420.6 | 417.7 |
| ISIS 141923 | 96.3 | 432.2 | 357.7 | 346.8 |
| ISIS 403527 | 77.3 | 296.0 | 219.9 | 207.9 |

TABLE 9

Effect of antisense oligonucleotides on plasma insulin (ng/mL)

|  | 0 min | 30 min |
|---|---|---|
| saline | 14.4 ± 1.8 | 10.6 ± 1.2 |
| ISIS 141923 | 17.2 ± 4.3 | 13.4 ± 1.2 |
| ISIS 403527 | 8.3 ± 1.4 | 14.6 ± 2.7 |

In RBP4 antisense oligonucleotides treated mice, initial glucose levels were lower and the increase in glucose levels during the GTT assay were mitigated compared to the saline control. Insulin levels were not significantly changed during this study, indicating that in the presence of similar insulin levels, antisense oligonucleotide treated mice had better glucose tolerance as compared to the saline controls.

Thus, the mice treated with ISIS 403527 are able to tolerate exogenous glucose better than the control. This finding further confirms the insulin sensitizing and glucose lowering effect after RBP4 antisense oligonucleotide inhibition.

Example 7

Effects of Antisense Inhibition of RBP4 in the ob/ob Mouse Model of Obesity on Insulin Sensitivity Insulin sensitivity in mice treated, as described in Example 3, was measured. The mice were fasted for 4 hours and insulin was injected at 0.7 U/kg. The sensitivity of the mice to insulin was measured.

TABLE 10

Effect of antisense oligonucleotides on blood glucose levels (mg/dL) in response to insulin injections

|  | 0 min | 15 min | 30 min | 60 min | 90 min |
|---|---|---|---|---|---|
| saline | 338.3 ± 34.4 | 428.7 ± 50.1 | 373.4 ± 60.8 | 209.4 ± 49.5 | 154.1 ± 31.3 |
| ISIS 141923 | 302.6 ± 36.4 | 351.4 ± 52.0 | 243.6 ± 51.7 | 131.3 ± 33.2 | 104.8 ± 23.3 |
| ISIS 403527 | 166.5 ± 15.3 | 205.7 ± 14.9 | 120.3 ± 10.6 | 62.2 ± 2.1 | 50.3 ± 4.3 |

At the 15 minute time-point, there was a sharp increase in glucose levels due to stress manifested in the mice because of the injections. At 30 minute, in RBP4 antisense oligonucleotides treated mice, significantly lower glucose levels were observed, which continued during the entire duration of ITT. This finding confirms that RBP4 inhibition by treatment with RBP4 antisense oligonucleotide caused an improvement in insulin sensitivity.

Example 8

Effects of Antisense Inhibition of RBP4 in the ob/ob Mouse Model of Obesity on Fatty Acid Metabolism Plasma ketone body levels, as depicted by 3-hydroxybutyrate (3-HB), were assayed in the mice and are shown in Table 11. After 4 weeks of RBP4 ASO treatment, plasma 3-HB levels were decreased by 58% (treated: 214.8 vs. saline: 510.9 µMol/L); plasma free fatty acids were decreased by 20% (treated: 1.2 vs. saline: 1.5 mEq/L).

Severe diabetes often causes ketosis due to increased ketogenesis. Reduced 3HB levels indicate that ISIS 403527 decreased ketogenesis in these mice; indicating an improvement of diabetic state. At the same time, there was a tendency in the antisense oligonucleotide-treated mice to display lower free fatty acids in the plasma, which also indicated an improvement of diabetes (Table 12).

TABLE 11

Effect of antisense oligonucleotides on 3-HB levels (µMol/L)

|  | 0 week - fed | 4 weeks - 5 h fasted |
|---|---|---|
| saline | 100.9 | 510.9 |
| ISIS 141923 | 112.4 | 552.4 |
| ISIS 403527 | 101.3 | 214.8 |

TABLE 12

Effect of antisense oligonucleotides on plasma free fatty acid levels (mEq/L)

|  | 0 week - fed | 4 weeks - 5 h fasted |
|---|---|---|
| saline | 0.8 | 1.5 |
| ISIS 141923 | 0.8 | 1.4 |
| ISIS 403527 | 0.8 | 1.2 |

Example 9

Effects of Antisense Inhibition of RBP4 in the OB/OB Mouse Model of Obesity on Metabolic Parameters Effect on Body Weight The effect of the treatment of the mice with ISIS 403527 on body weight was monitored over 5 weeks. There was no effect on body weight or lean mass between the saline controls and the ISIS 403527-treated mice.

Effect on Fat Content and Cholesterol Levels

ISIS 403527 was tested for its ability to affect lipid metabolism in ob/ob mice that received antisense oligonucleotide treatment, as described in Example 4. Blood was obtained and analyzed for cholesterol and plasma lipids. The data in Tables 13 and 14 show that there were no significant changes in the fat content or plasma cholesterol levels after treatment with ISIS 403527 or ISIS 141923, however, the total fat content shows a general trend towards reduction and the total plasma cholesterol did not increase as much, relative to the controls in this model.

TABLE 13

Effect of antisense oligonucleotides on total fat content (g)

|  | Total fat | WAT | BAT |
|---|---|---|---|
| saline | 31.6 | 4.6 | 0.97 |
| ISIS 141923 | 32.5 | 4.4 | 1.1 |
| ISIS 403527 | 30.2 | 4.1 | 1.11 |

TABLE 14

Effect of antisense oligonucleotides on total plasma cholesterol levels (mg/dL)

|  | 0 week - fed | 2 weeks - fed | 4 weeks - 5 h fasting |
|---|---|---|---|
| saline | 252.7 | 380.6 | 296.4 |
| ISIS 141923 | 242.1 | 378.3 | 305.6 |
| ISIS 403527 | 241.8 | 354.3 | 282.1 |

Effect on Metabolic Rate

Metabolic rate of the mice was determined by measuring the oxygen consumption rate and respiratory quotient, and was found to be similar in all the groups of mice.

Taken together, the relative unchanged status of a significant reduction in body weight, body fat content, cholesterol levels and metabolic rate signify that the decrease in glucose levels and improved insulin sensitivity in these mice, as a result of treatment with ISIS 403527, is a direct effect of the antisense oligonucleotide treatment and not a secondary effect caused by changes in body weight and body fat content.

Example 10

Effects of Antisense Inhibition of RBP4 in the Diet-Induced Obesity Mouse Model

The C57BL/6 mouse strain is reported to be prone to diet-induced obesity and is accepted as a model for diet-induced obesity for human (C. Gallou-Kabani et al, *Obesity* (2007) 15, 1996-2005). To induce obesity, these mice were fed a high-fat diet and used in the following studies to evaluate the effects of ISIS 403527 on RBP4 expression.

Treatment

Male C57BL/6 mice at 7 weeks of age were placed on a high-fat diet containing 58% calories from fat (Research Diet D12330, Research Diets Inc., New Brunswick, N.J.). The mice were divided into four treatment groups. One group received subcutaneous injections of ISIS 403527 at a dose of 25 mg/kg twice per week for 6 weeks. The second group received subcutaneous injections of ISIS 141923 at a dose of 25 mg/kg twice per week for 6 weeks. The third group received subcutaneous injections of saline twice weekly for 6 weeks. This saline-injected group served as the control group to which the oligonucleotide-treated groups were compared. Saline-injected lean mice were also used as a normal control group.

Inhibition of RBP4 mRNA

At the end of the six week treatment period, the mice were sacrificed and RBP4 mRNA expression was measured in liver and white adipose tissue by real-time RT-PCR.

The results shown in Table 15 are expressed as percent inhibition relative to saline-treated mice. The data show that ISIS 403527 inhibited RBP4 expression by over 71% in the liver and by 67% in the WAT. The control ISIS 141923 did not inhibit RBP4 expression significantly.

TABLE 15

Percent inhibition of RBP4 in DIO mouse model relative to saline control

|  | Liver | WAT |
|---|---|---|
| Saline | 0.0 | 0.0 |
| ISIS 141923 | 2.8 | 0.0 |
| ISIS 403527 | 71.4 | 66.7 |

Therefore ISIS 403527 was able to significantly inhibit RBP4 gene expression in the DIO model.

Example 11

Effects of Antisense Inhibition of RBP4 in the Diet-Induced Obesity Mouse Model on Plasma Glucose and Insulin Levels Plasma glucose treated mice, as described in Example 10, was determined using an automated clinical chemistry analyzer (Hitachi Olympus AU400e, Melville, N.Y.). Plasma insulin levels were determined using an ELISA kit from ALPCO Diagnostics. The results, as shown in Tables 16 and 17, illustrate changes in fed and fasted plasma glucose and insulin levels. Measurements were taken at 0 weeks, 3 weeks, 5 weeks and 6 weeks.

TABLE 16

Effect of antisense oligonucleotides on plasma glucose levels (mg/dL)

|  | 0 week fed | 3 week fed | 5 weeks 6-hr fasted | 6 week fed |
|---|---|---|---|---|
| saline | 218.1 | 227.6 | 236.7 | 244.2 |
| ISIS 141923 | 234.3 | 211.3 | 248.3 | 240.7 |
| ISIS 403527 | 216.2 | 208.1 | 198.7 | 203.0 |

ISIS 403527 treatment in the DIO model decreased fasted plasma glucose concentrations by 16% (treated: 198.7 vs. saline: 236.7 mg/dL) by week 5 and decreased fed plasma glucose levels by 16% by week 6 (treated: 203.0 vs saline: 244.2 mg/dL).

TABLE 17

Effects of antisense oligonucleotides on plasma insulin levels (ng/mL)

|  | 0 week fed | 3 week fed | 5 weeks 6-hr fasted | 6 week fed |
|---|---|---|---|---|
| saline | 5.7 | 4.9 | 3.2 | 4.9 |
| ISIS 141923 | 5.8 | 5.7 | 3.7 | 3.9 |
| ISIS 403527 | 5.8 | 3 | 2.3 | 2.3 |

ISIS 403527 treatment in the DIO model also decreased fasted plasma insulin levels by 28% (treated: 2.3 vs. saline: 3.2 ng/mL) by week 5 and decreased fed plasma insulin levels by 53% by week 6 (treated: 2.3 vs. saline: 4.9 ng/mL). This data indicates an improvement in insulin sensitivity, since hyperinsulinemia is a consequence of insulin resistance in this model.

Example 12

Effect of Antisense Inhibition of RBP4 in the Diet-Induced Obesity Mouse Model on Glucose Tolerance Glucose tolerance in mice treated, as described in Example 10, was measured. The mice were fasted overnight and then an intraperitoneal injection of glucose at a dose of 1.2 g/kg was given. Blood glucose and insulin levels were measured before the glucose challenge and at intervals over 120 minutes.

The blood glucose levels (mg/dL) are shown below in Table 18. The glucose levels (glucose excursion) in ISIS 403527 mice were significantly lower than controls during GTT.

TABLE 18

Effect of antisense oligonucleotides on glucose tolerance (mg/dL)

|  | 0 min | 30 min | 60 min | 90 min | 120 min |
|---|---|---|---|---|---|
| saline | 162.8 | 308 | 285 | 226.7 | 232.5 |
| ISIS 141923 | 197.5 | 324.8 | 300.5 | 262.8 | 234.7 |
| ISIS 403527 | 158.2 | 237.5 | 206.3 | 185.5 | 177.5 |

The data shows that ISIS 403527 improved glucose tolerance in the DIO mice, similar to the data obtained in the ob/ob model.

Example 13

Effects of Antisense Inhibition of RBP4 in the Diet-Induced Obesity Mouse Model on Plasma Resistin Levels Resistin is a hormone secreted by the adipose tissue. Studies show a correlation between resistin and obesity and insulin resistance, with increase in resistin levels being linked to increased insulin resistance. This is further authenticated with studies on subjects of type 2 diabetes mellitus where elevated resistin levels were observed.

Accordingly, plasma resistin levels in DIO mice treated with ISIS 403527 were measured and compared with control mice. Resistin levels in ISIS 403527-treated mice were decreased by 43% (treated: 2.9 vs. controls: 5.1 ng/mL).

Therefore, plasma resistin in the DIO mice was decreased by treatment with ISIS 403527, further indicating that treatment with RBP4 antisense oligonucleotides can decrease insulin resistance.

Example 14

Effect of Antisense Inhibition of RBP4 in the Diet-Induced Obesity Mouse Model on Cholesterol and Triglyceride Levels ISIS 403527 was tested for its ability to affect lipid metabolism in DIO mice that received antisense oligonucleotide treatment, as described in Example 10. Blood was obtained and analyzed for cholesterol and plasma lipids. The data in Tables 19-22 show that there were no significant changes in lipid and cholesterol levels in this particular model. Measurements were taken at 0 weeks, 3 weeks, 5 weeks and 6 weeks.

TABLE 19

Effect of antisense oligonucleotides on plasma cholesterol levels (mg/dL)

|  | 0 week fed | 3 week fed | 5 weeks 6-hr fasted | 6 week fed |
|---|---|---|---|---|
| saline | 215.2 ± 10.3 | 237.0 ± 11.2 | 261.7 ± 13.3 | 284.7 ± 7.1 |
| ISIS 141923 | 222.3 ± 9.2 | 249.1 ± 9.0 | 273.4 ± 6.7 | 266.2 ± 14.3 |
| ISIS 403527 | 216.3 ± 6.0 | 286.7 ± 4.9 | 326.4 ± 20.8 | 320.5 ± 7.4 |

TABLE 20

Effect of antisense oligonucleotides on plasma triglyceride levels (mg/dL)

|  | 0 week fed | 6 week fed |
|---|---|---|
| saline | 130.6 ± 8.4 | 166.7 ± 7.2 |
| ISIS 141923 | 130.2 ± 9.6 | 155.2 ± 11.4 |
| ISIS 403527 | 142.2 ± 11.9 | 185.5 ± 30.2 |

TABLE 21

Effect of antisense oligonucleotides on HDL cholesterol levels (mg/dL)

|  | 0 week fed | 5 weeks 6-hr fasted | 6 week fed |
|---|---|---|---|
| saline | 164.2 ± 10.6 | 123.1 ± 3.4 | 135.8 ± 1.8 |
| ISIS 141923 | 173.8 ± 7.3 | 136.0 ± 2.8 | 129.2 ± 5.4 |
| ISIS 403527 | 165.8 ± 4.5 | 132.1 ± 7.2 | 130.2 ± 4.1 |

TABLE 22

Effect of antisense oligonucleotides on LDL cholesterol levels (mg/dL)

|  | 0 week fed | 5 weeks 6-hr fasted | 6 week fed |
|---|---|---|---|
| saline | 31.3 ± 1.5 | 7.2 ± 0.5 | 5.0 ± 0.5 |
| ISIS 141923 | 29.2 ± 1.2 | 6.1 ± 0.6 | 5.2 ± 0.8 |
| ISIS 403527 | 28.4 ± 0.7 | 11.3 ± 1.7 | 8.7 ± 0.6 |

Similar to the findings obtained in the ob/ob mice, ISIS 403527 had little significance on cholesterol levels compared to the controls. Any reduction in HDL cholesterol levels are not significant and are due to standard error in measurement normally seen in assays.

Example 15

Effect of Antisense Inhibition of RBP4 in the Diet-Induced Obesity Mouse Model on Insulin Sensitivity ISIS 403527 was tested for its ability to affect insulin sensitivity in DIO mice that received antisense oligonucleotide treatment, as described in Example 10. A group of lean mice treated with saline were included as controls.

After the treatment, hepatic and peripheral insulin sensitivity was assessed using hyperinsulinemic-euglycemic clamps. Seven to nine days prior to the clamp, catheters were inserted into the right internal jugular vein extending to the right atrium and the left carotid artery extending into the aortic arch. Subsequently, the mice were fasted for 24 hours, and then infused with 99% [6,6-$^2$H] glucose (1.1 mg/kg prime, 0.1 mg/kg) infusion to assess basal glucose turnover. Ensuing the basal period, the hyperinsulinemic-euglycemic clamp was conducted for 140 minutes with a primed/continuous infusion of insulin (400 mU/kg prime over 5 minutes, 4 mU/kg per minute infusion subsequently) and a variable infusion of 20% dextrose spiked with approximately 2.5% [6,6-$^2$H]glucose to maintain euglycemia. The results are presented in Table 23.

TABLE 23

Effect of antisense oligonucleotides on insulin sensitivity

|  | Saline control | Lean control | ISIS 141923 | ISIS 403527 |
|---|---|---|---|---|
| Hepatic glucose output (mg/kg/min) | 22 | 12 | 22 | 13 |
| Glucose infusion rate (mg/kg/min) | 9 | 124 | 11 | 34 |
| Whole body glucose uptake (mg/kg/min) | 32 | 55 | 34 | 46 |
| Whole body glycolysis (mg/kg/min) | 31 | 30 | 32 | 43 |
| Muscle glucose Uptake (mg/kg/min) | 16 | 45 | 17 | 27 |
| Heart glucose Uptake (mg/kg/min) | 15 | 189 | 18 | 69 |
| WAT glucose Uptake (mg/kg/min) | 0.8 | 2.1 | 0.7 | 1.2 |

ISIS 403527-treated mice, compared to the control, demonstrated a 41% reduction in basal hepatic glucose production (treated: 13 vs. saline: 22 mg/kg/min). The rate with which glucose was infused to maintain euglycemia was 71% higher in the ISIS 403527-treated group compared to the control (treated: 34 vs. saline: 9 mg/kg/min), indicating improved whole body insulin sensitivity in ISIS 403527-treated group. Treatment with ISIS 403527 significantly enhanced the rate of glucose uptake in both muscle and white adipose tissue (P<0.05). Furthermore, treatment with ISIS 403527 dramatically increased heart glucose uptake. For the first time, it can be shown that RBP4 antisense inhibition can dramatically improve glucose uptake in the heart, providing a potential therapeutic for glucose uptake related diseases like diabetic cardiomyopathy. This data also demonstrates an improvement in insulin sensitivity not only in liver but also in peripheral tissues. In addition, ISIS 403527 treatment significantly increased whole body glycolysis (treated: 43 vs. saline: 31 mg/kg/min).

The results shown herein demonstrate that inhibiting RBP4 expression improves whole body insulin sensitivity and decreases hepatic gluconeogenesis. For the first time, these results indicate that antisense inhibitors of RBP4 are candidate therapeutic agents for the treatment of conditions characterized by elevated hepatic glucose production and decreased peripheral glucose uptake, such as metabolic disorders like Type 2 diabetes. In addition, for the first time, these results indicate improved heart glucose uptake, indicating that antisense inhibitors of RBP4 can be used as agents for treatment of cardiomyopathy, which is commonly seen in patients with type 2 diabetes.

Example 16

Antisense Inhibition of RBP4 in Rat Primary Hepatocytes

Antisense oligonucleotides targeted to a RBP4 nucleic acid were tested for their effects on RBP4 mRNA in vitro. Rat primary hepatocytes were transfected using lipofectin reagent with 200 nM antisense oligonucleotide for 4 hours. After a recovery period of approximately 24 hours, RNA was isolated from the cells and RBP4 mRNA levels were measured by quantitative real-time PCR. RBP4 mRNA levels were adjusted according to total RNA content, as measured by RIBOGREEN®. Results are presented as percent inhibition of RBP4, relative to untreated control cells.

The chimeric antisense oligonucleotides in Table 24 were designed as 5-10-5 MOE gapmers. The gapmers are 20 nucleotides in length, wherein the central gap segment is comprised of 10 2'-deoxynucleotides and is flanked on both sides (in the 5' and 3' directions) by wings comprising 5 nucleotides each. Each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines. "Rat target start site" indicates the 5'-most nucleotide to which the gapmer is targeted in the rat sequence. "Rat target stop site" indicates the 3'-most nucleotide to which the gapmer is targeted in the rat sequence. Each gapmer listed in Table 24 is targeted to rat target sequence SEQ ID NO: 84 (GENBANK Accession No. NM_013162.1).

The rat oligonucleotides also show cross reactivity with the human RBP4 mRNA (GENBANK Accession No. NM_006744.3), incorporated herein as SEQ ID NO: 5. "Human Target Start Site" indicates the 5'-most nucleotide in the human mRNA to which the antisense oligonucleotide is targeted. "Human Target Stop Site" indicates the 3'-most nucleotide in the human mRNA to which the antisense oligonucleotide is targeted. 'Mismatches' indicates the number of nucleobases by which the rat oligonucleotide is mismatched with the human gene sequence. "n/a" indicates that there was no cross-reactivity between the rat oligonucleotide and the human gene sequence.

TABLE 24

Inhibition of rat RBP4 mRNA levels by chimeric antisense oligonucleotides having 5-10-5 MOE wings and deoxy gap

| ISIS No. | Rat Target Start Site | Rat Target Stop Site | Rat Target sequence | Sequence (5' to 3') | % inhibition | Human Target Start Site | Human Target Stop Site | Mismatches | SEQ ID NO. |
|---|---|---|---|---|---|---|---|---|---|
| 403527 | 853 | 872 | NM_013162.1 | GGAATCCCAAGCCTCAAACG | 74 | n/a | n/a | n/a | 8 |
| 403528 | 860 | 879 | NM_013162.1 | CAAGTTTGGAATCCCAAGCC | 60 | n/a | n/a | n/a | 9 |
| 403529 | 73 | 92 | NM_013162.1 | TCCCAGAGCCGCCAGCAGCA | 22 | 107 | 126 | 3 | 10 |
| 403530 | 107 | 126 | NM_013162.1 | TGCTCACCCTGCAGTCGCGC | 59 | 141 | 160 | 2 | 11 |
| 403531 | 141 | 160 | NM_013162.1 | CGAGCCTTGTCGAAGTTCTC | 57 | 175 | 194 | 0 | 12 |

TABLE 24-continued

Inhibition of rat RBP4 mRNA levels by chimeric antisense
oligonucleotides having 5-10-5 MOE wings and deoxy gap

| ISIS No. | Rat Target Start Site | Rat Target Stop Site | Rat Target sequence | Sequence (5' to 3') | % inhibition | Human Target Start Site | Human Target Stop Site | Mis-matches | SEQ ID NO. |
|---|---|---|---|---|---|---|---|---|---|
| 403532 | 146 | 165 | NM_013162.1 | AGAAACGAGCCTTGTCGAAG | 38 | 180 | 199 | 1 | 13 |
| 403533 | 151 | 170 | NM_013162.1 | CCCAGAGAAACGAGCCTTGT | 97 | 185 | 204 | 1 | 14 |
| 403534 | 159 | 178 | NM_013162.1 | TACCAGAGCCCAGAGAAACG | 32 | 193 | 212 | 3 | 15 |
| 403535 | 164 | 183 | NM_013162.1 | TGGCATACCAGAGCCCAGAG | 81 | 198 | 217 | 3 | 16 |
| 403536 | 169 | 188 | NM_013162.1 | GGCGATGGCATACCAGAGCC | 90 | n/a | n/a | n/a | 17 |
| 403537 | 177 | 196 | NM_013162.1 | TCCTTTTTGGCGATGGCATA | 82 | 211 | 230 | 3 | 18 |
| 403538 | 198 | 217 | NM_013162.1 | TGCAAAAAGAGACCCTCGGG | 77 | 232 | 251 | 2 | 19 |
| 403539 | 203 | 222 | NM_013162.1 | TGTCTTGCAAAAAGAGACCC | 12 | 237 | 256 | 3 | 20 |
| 403540 | 208 | 227 | NM_013162.1 | GATGTTGTCTTGCAAAAAGA | 0 | 242 | 261 | 2 | 21 |
| 403541 | 213 | 232 | NM_013162.1 | GCGATGATGTTGTCTTGCAA | 58 | 247 | 266 | 3 | 22 |
| 403542 | 218 | 237 | NM_013162.1 | ACTCAGCGATGATGTTGTCT | 47 | 252 | 271 | 3 | 23 |
| 403543 | 223 | 242 | NM_013162.1 | AGAAAACTCAGCGATGATGT | 40 | n/a | n/a | n/a | 24 |
| 403544 | 228 | 247 | NM_013162.1 | TCCACAGAAAACTCAGCGAT | 39 | n/a | n/a | n/a | 25 |
| 403545 | 283 | 302 | NM_013162.1 | GTTGCTCAGAAGACGGACTC | 38 | 317 | 336 | 3 | 26 |
| 403546 | 288 | 307 | NM_013162.1 | TCCCAGTTGCTCAGAAGACG | 21 | 322 | 341 | 3 | 27 |
| 403547 | 293 | 312 | NM_013162.1 | ACACTTCCCAGTTGCTCAGA | 27 | n/a | n/a | n/a | 28 |
| 403548 | 298 | 317 | NM_013162.1 | TGCACACACTTCCCAGTTGC | 54 | n/a | n/a | n/a | 29 |
| 403549 | 303 | 322 | NM_013162.1 | ATGTCTGCACACACTTCCCA | 43 | 337 | 356 | 2 | 30 |
| 403550 | 308 | 327 | NM_013162.1 | CCACCATGTCTGCACACACT | 43 | 342 | 361 | 2 | 31 |
| 403551 | 313 | 332 | NM_013162.1 | AGTGCCCACCATGTCTGCAC | 23 | 347 | 366 | 2 | 32 |
| 403552 | 319 | 338 | NM_013162.1 | TGTGAAAGTGCCCACCATGT | 49 | 353 | 372 | 1 | 33 |
| 403553 | 345 | 364 | NM_013162.1 | TTGAACTTGGCAGGATCTTC | 50 | 379 | 398 | 2 | 34 |
| 403554 | 351 | 370 | NM_013162.1 | TTCATCTTGAACTTGGCAGG | 69 | 385 | 404 | 0 | 35 |
| 403555 | 359 | 378 | NM_013162.1 | CCCAGTACTTCATCTTGAAC | 37 | 393 | 412 | 0 | 36 |

TABLE 24-continued

Inhibition of rat RBP4 mRNA levels by chimeric antisense
oligonucleotides having 5-10-5 MOE wings and deoxy gap

| ISIS No. | Rat Target Start Site | Rat Target Stop Site | Rat Target sequence | Sequence (5' to 3') | % inhibition | Human Target Start Site | Human Target Stop Site | Mis-matches | SEQ ID NO. |
|---|---|---|---|---|---|---|---|---|---|
| 403556 | 365 | 384 | NM_013162.1 | CTACACCCCA GTACTTCATC | 14 | 399 | 418 | 1 | 37 |
| 403557 | 370 | 389 | NM_013162.1 | GGAGGCTACA CCCCAGTACT | 59 | 404 | 423 | 1 | 38 |
| 403558 | 375 | 394 | NM_013162.1 | AGAAAGGAGG CTACACCCCA | 52 | 409 | 428 | 1 | 39 |
| 403559 | 380 | 399 | NM_013162.1 | GCTGGAGAAA GGAGGCTACA | 56 | 414 | 433 | 2 | 40 |
| 403560 | 389 | 408 | NM_013162.1 | CGTTTCCTCG CTGGAGAAAG | 53 | 423 | 442 | 3 | 41 |
| 403561 | 407 | 426 | NM_013162.1 | CGATGATCCA GTGGTCATCG | 0 | 441 | 460 | 2 | 42 |
| 403562 | 437 | 456 | NM_013162.1 | ACTGCAGAGC GAAGGTGTCG | 28 | n/a | n/a | n/a | 43 |
| 403563 | 459 | 478 | NM_013162.1 | AGATTCTGCA GGCGGCAGGA | 34 | 493 | 512 | 3 | 44 |
| 403564 | 465 | 484 | NM_013162.1 | CCATCCAGAT TCTGCAGGCG | 50 | n/a | n/a | n/a | 45 |
| 403565 | 474 | 493 | NM_013162.1 | GCACAGGTGC CATCCAGATT | 67 | 508 | 527 | 2 | 46 |
| 403566 | 479 | 498 | NM_013162.1 | TGTCTGCACA GGTGCCATCC | 50 | 513 | 532 | 2 | 47 |
| 403567 | 612 | 631 | NM_013162.1 | CTTTGACAGT AACCATTGTG | 57 | n/a | n/a | n/a | 48 |
| 403570 | 682 | 701 | NM_013162.1 | GAAAGCTAAT CAGAAATCTT | 0 | n/a | n/a | n/a | 51 |
| 403571 | 690 | 709 | NM_013162.1 | GACCGGATGA AAGCTAATCA | 12 | n/a | n/a | n/a | 52 |
| 403572 | 704 | 723 | NM_013162.1 | TAAATAGAGA TGAAGACCGG | 9 | 735 | 754 | 3 | 53 |
| 403573 | 712 | 731 | NM_013162.1 | TTCTAAGATA AATAGAGATG | 31 | 743 | 762 | 2 | 54 |
| 403574 | 756 | 775 | NM_013162.1 | TTAATGTCCA CCTAGAGAAG | 34 | n/a | n/a | n/a | 55 |
| 403589 | 1510 | 1529 | NW_047565.2_ TRUNC_ 10625000_ 10636000_COMP | TGATGGTGGC CTCACTGAGC | 0 | n/a | n/a | n/a | 70 |
| 403594 | 2402 | 2421 | NW_047565.2_ TRUNC_ 10625000_ 10636000_COMP | GGCCACTGAC CTCAGAAGAC | 1 | n/a | n/a | n/a | 75 |
| 403596 | 5380 | 5399 | NW_047565.2_ TRUNC_ 10625000_ 10636000_COMP | TGGTTTCAAA TGTTCAACAG | 0 | n/a | n/a | n/a | 77 |
| 403597 | 5505 | 5524 | NW_047565.2_ TRUNC_ 10625000_ 10636000_COMP | GTGCCTGAGG CAGAGACTAT | 26 | n/a | n/a | n/a | 78 |

Table 24 demonstrates that rat oligonucleotide activity is indicative of human oligonucleotide activity targeted to a similar region.

Example 17

Effect of Antisense Inhibition of RBP4 in the Zucker Diabetic Fatty (ZDF) Rat Model Treatment The leptin receptor defective Zucker diabetic fatty (ZDF) rat is another useful model for the investigation of type 2 diabetes. Diabetes develops spontaneously in these male rats at ages 8-10 weeks, and is associated with hyperphagia, polyuria, polydipsia, and impaired weight gain, symptoms which parallel the clinical symptoms of diabetes (Phillips M S, et al., 1996, Nat Genet. 13, 18-19).

ZDF/GmiCrl-fa/fa (ZDF) male rats were purchased from Charles River Laboratories (Wilmington, Mass., USA). Six week old ZDF male rats were injected intraperitoneally with oligonucleotides at a dose of 25 mg/kg two times per week for 8.5 weeks. RBP4 antisense oligonucleotides used were ISIS 403527 (SEQ ID NO: 8) and ISIS 403536 (SEQ ID NO: 17). ISIS 141923 (SEQ ID NO: 4) was used as the negative oligonucleotide control. Saline-injected animals also served as controls.

Inhibition of RBP4 mRNA Levels

At the end of the 8.5 week treatment period, the rats were sacrificed and RBP4 mRNA expression was measured in liver and white adipose tissue by real-time RT-PCR. The results are presented in Table 25, and are expressed as a percentage of the saline control.

TABLE 25

Percent inhibition of RBP4 in ZDF rat model relative to saline control

| | Liver | WAT |
|---|---|---|
| ISIS 141923 | 20 | 4 |
| ISIS 403527 | 64 | 39 |
| ISIS 403536 | 83 | 40 |

Therefore, ISIS 403527 and ISIS 403536 were able to significantly inhibit RBP4 gene expression in the DIO model and can be used as candidate therapeutic agents for the treatment of disorders characterized by RBP4 expression in this rat model.

Inhibition of RBP4 Protein Levels

The reduction of RBP4 (protein) levels in the plasma was also measured by an ELISA kit. Plasma levels were monitored in both fed and fasted states. The results are presented in Table 26 and expressed as μg/mL.

TABLE 26

Effect of antisense oligonucleotides on RBP4 plasma protein levels (μg/mL)

| | 0 weeks (fed) | 3.5 weeks (fed) | 6.5 weeks (6 hr fasted) | 8.5 weeks (fed) |
|---|---|---|---|---|
| Saline | 47 | 57 | 45 | 42 |
| ISIS 141923 | 47 | 42 | 45 | 33 |
| ISIS 403527 | 52 | 28 | 24 | 12 |
| ISIS 403536 | 53 | 21 | 15 | 7 |

Example 18

Effect of Antisense Inhibition of RBP4 in Zucker Diabetic Fatty (ZDF) Rat Model on Plasma Glucose Plasma glucose in rats treated, as described in Example 17, was determined using an automated clinical chemistry analyzer (Hitachi Olympus AU400e, Melville, N.Y.). Plasma insulin levels were determined using an ELISA kit from ALPCO Diagnostics. The results, as shown in Tables 27 and 28, illustrate changes in fed and fasted plasma glucose. Measurements were taken at 0 weeks, 3.5 weeks, and 6.5 weeks.

TABLE 27

Effect of antisense oligonucleotides on plasma glucose levels (mg/dL)

| | 0 week (fed) | 3.5 week (fed) | 6.5 week (6 hr fasted) |
|---|---|---|---|
| saline | 224 | 462 | 482 |
| ISIS 141923 | 229 | 400 | 411 |
| ISIS 403527 | 219 | 280 | 248 |
| ISIS 403536 | 218 | 342 | 279 |

ISIS 403527 treatment in the ZDF model decreased fasted plasma glucose concentrations by 49% (treated: 248 vs. saline: 482 mg/dL) by week 6.5 and decreased fed plasma glucose levels by 39% by week 3.5 (treated: 280 vs. saline: 462 mg/dL). ISIS 403536 treatment in the ZDF model decreased fasted plasma glucose concentrations by 42% (treated: 279 vs. saline: 482 mg/dL) by week 6.5 and decreased fed plasma glucose levels by 26% by week 3.5 (treated: 342 vs saline: 462 mg/dL). This data shows, for the first time, that RBP4 inhibition leads to significant glucose lowering in diabetic models.

Example 19

Effect of Antisense Inhibition of RBP4 in Zucker Diabetic Fatty (ZDF) Rat Model on Glucose Tolerance An oral glucose tolerance test (OGTT) was performed. Rats treated, as described in Example 17, were fasted overnight and then received oral administration of glucose of 0.75 mg/kg. Blood glucose levels were measured before the glucose challenge and at intervals over 2 hours. The blood glucose levels (mg/dL) are shown below in Table 28. The glucose levels (glucose excursion) in ISIS 403527 and ISIS 403536 rats were significantly lower than controls during GTT.

TABLE 28

Effect of antisense oligonucleotides on glucose levels (mg/dL) during OGTT

| | 0 min | 15 min | 30 min | 60 min | 90 min | 120 min |
|---|---|---|---|---|---|---|
| saline | 125 | 318 | 367 | 370 | 352 | 324 |
| ISIS 141923 | 93 | 224 | 319 | 313 | 300 | 280 |
| ISIS 403527 | 68 | 183 | 241 | 238 | 153 | 113 |
| ISIS 403536 | 78 | 206 | 269 | 231 | 180 | 153 |

The data shows that ISIS 403527 and ISIS 403536 improved glucose tolerance in the ZDF model.

Example 20

Effect of Antisense Inhibition of RBP4 in Zucker Diabetic Fatty (ZDF) Rat Model on Insulin Sensitivity During the insulin sensitivity tolerance test (ITT), rats treated as described in Example 17, were fasted for 4 hours, injected with insulin at 1.0 U/kg and tested for blood glucose levels over a period of 2 hours. The blood glucose levels (mg/dL) are shown below in Table 29. The glucose levels in ISIS 403527 and ISIS 403536 rats were significantly lower than controls during ITT.

TABLE 29

Effect of antisense oligonucleotides on blood glucose levels (mg/dL) during ITT

|  | 0 min | 30 min | 60 min | 90 min | 120 min |
|---|---|---|---|---|---|
| saline | 393 | 370 | 283 | 209 | 174 |
| ISIS 141923 | 321 | 276 | 231 | 178 | 134 |
| ISIS 403527 | 106 | 96 | 74 | 51 | 47 |
| ISIS 403536 | 184 | 177 | 124 | 97 | 84 |

The data shows that ISIS 403527 and ISIS 403536 improved insulin sensitivity in the ZDF model.

Example 21

Effect of Antisense Inhibition of RBP4 in Zucker Diabetic Fatty (ZDF) Rat Model on Fatty Acid Metabolism Plasma ketone body levels, as depicted by 3-hydroxybutyrate (3-HB) levels, were assayed in the rat groups and are shown in Table 30. Plasma 3HB was decreased by 51% (treated: 60 vs. saline: 123 µMol/L) in ISIS 403527 treated rats at 6.5 weeks after fasting the rats for 6 hrs; plasma free fatty acids were decreased by 27% (treated: 0.71 vs. saline: 0.97 mEq/L). In ISIS 403536 treated rats, 3HB was decreased by 51% (treated: 60 vs. saline: 123 µMol/L) at 6.5 weeks after fasting the rats for 6 hrs; plasma free fatty acids were decreased by 20% (treated: 0.78 vs. saline: 0.97 mEq/L).

Fatty acid metabolism was measured in rats treated as described in Example 17. Free fatty acid levels and 3-hydroxybutyrate (3HB) levels in the plasma were measured after 8.5 weeks of treatment. The data for free fatty acid level analysis is presented in Table 31.

TABLE 30

Effect of antisense oligonucleotides on 3-HB levels (µMol/L)

|  | 0 week (fed) | 3.5 weeks (fed) | 5 weeks (o/n fast) | 6.5 weeks (6 hr fast) |
|---|---|---|---|---|
| saline | 106 | 96 | 133 | 123 |
| ISIS 141923 | 101 | 92 | 159 | 93 |
| ISIS 403527 | 104 | 94 | 113 | 60 |
| ISIS 403536 | 105 | 102 | 115 | 60 |

TABLE 31

Effect of antisense oligonucleotides on plasma free fatty acid levels (mEq/L)

|  | 0 week (fed) | 3.5 weeks (fed) | 5 weeks (o/n fast) | 6.5 weeks (6 hr fast) |
|---|---|---|---|---|
| saline | 1.02 | 0.78 | 0.98 | 0.97 |
| ISIS 141923 | 1.06 | 0.69 | 1.08 | 0.85 |
| ISIS 403527 | 1.06 | 0.61 | 1.04 | 0.71 |
| ISIS 403536 | 1.12 | 0.76 | 1.12 | 0.78 |

Severe diabetes often causes ketosis due to increased ketogenesis. Reduced 3HB levels indicate that ISIS 403527 decreased ketogenesis in these rats due to improvement of diabetic state. At the same time, there was a tendency in the antisense oligonucleotide-treated rats to display lower free fatty acids in the plasma, which also indicated an improvement of diabetes.

Example 22

Effect of Antisense Inhibition of RBP4 in Zucker Diabetic Fatty (ZDF) Rat Model on Cholesterol and Triglyceride Levels ISIS 403527 and ISIS 403536 were tested for their ability to affect lipid metabolism in ZDF rats that received antisense oligonucleotide treatment, as described in Example 17. Blood was obtained and analyzed for cholesterol and plasma lipids. The data in Tables 32-35 show that both ISIS 403527 and ISIS 403536 significantly lowered total cholesterol, HDL and LDL levels but had no effect on plasma triglyceride levels after 6 weeks of treatment.

TABLE 32

Effect of antisense oligonucleotides on plasma cholesterol levels (mg/dL)

|  | 0 week (fed) | 3 week (fed) | 5 weeks (o/n fasted) | 6 week (6 hr fasted) |
|---|---|---|---|---|
| saline | 122 | 152 | 166 | 161 |
| ISIS 141923 | 124 | 143 | 135 | 141 |
| ISIS 403527 | 126 | 116 | 122 | 101 |
| ISIS 403536 | 122 | 143 | 130 | 116 |

TABLE 33

Effect of antisense oligonucleotides on plasma triglyceride levels (mg/dL)

|  | 0 week (fed) | 3 week (fed) | 5 weeks (o/n fasted) | 6 week (6 hr fasted) |
|---|---|---|---|---|
| saline | 474 | 691 | 405 | 346 |
| ISIS 141923 | 457 | 472 | 431 | 332 |
| ISIS 403527 | 438 | 530 | 544 | 365 |
| ISIS 403536 | 458 | 626 | 454 | 407 |

TABLE 34

Effect of antisense oligonucleotides on HDL cholesterol levels (mg/dL)

|  | 0 week (fed) | 3 week (fed) | 5 weeks (o/n fasted) | 6 week (6 hr fasted) |
|---|---|---|---|---|
| saline | 81 | 101 | 121 | 132 |
| ISIS 141923 | 82 | 104 | 93 | 117 |
| ISIS 403527 | 85 | 80 | 69 | 76 |
| ISIS 403536 | 82 | 95 | 88 | 88 |

TABLE 35

Effect of antisense oligonucleotides on LDL cholesterol levels (mg/dL)

|  | 0 week (fed) | 3 week (fed) | 5 weeks (o/n fasted) | 6 week (6 hr fasted) |
|---|---|---|---|---|
| saline | 15 | 22 | 19 | 17 |
| ISIS 141923 | 14 | 15 | 14 | 16 |
| ISIS 403527 | 13 | 14 | 15 | 12 |
| ISIS 403536 | 15 | 19 | 15 | 12 |

Improvement of plasma cholesterol and plasma triglycerides levels, shown herein, demonstrate that treatment with RBP4 antisense inhibitors can be agents for the treatment of dyslipidemia, in particular, subjects having defective leptin receptors and/or type 2 diabetes and other related disorders.

Example 23

Effect of Inhibition of Transthyretin Expression by Antisense Oligonucleotides on RBP4 Levels and Glucose Metabolism RBP4 binds to transthyretin (TTR) to form a protein complex that reduces renal clearance of RBP4 (Naylor H M, et al. Biochemistry. 1999; 38:2647-2653). We therefore predicted that inhibition of TTR expression would prevent formation of the complex with RBP4 and therefore lead to renal clearance of RBP4 and decrease plasma RBP4 levels. ISIS 401724 (TACAAATGGGATGCTACTGC (SEQ ID NO: 85), target start site 506) was designed to target the TTR mRNA sequence (GENBANK Accession No. NM_013697.1), designated herein as SEQ ID NO: 86.

Treatment

C57BL/6 mice were fed a high-fat diet containing 58% calories from fat (Research Diet D12330, Research Diets Inc., New Brunswick, N.J.) for 4 months. The mice were then divided into 3 groups. The first group was administered the TTR antisense oligonucleotide, ISIS 401724 at 25 mg/kg twice a week for 4 weeks. The second group was administered control oligonucleotide ISIS 141923 at 25 mg/kg twice a week for 4 weeks. The third group was administered saline twice a week for 4 weeks. A control group of mice fed a normal diet was also included.

Inhibition of RNA and Protein Levels

At the end of the treatment period, mice were sacrificed and TTR mRNA expression was measured in the liver by real-time RT-PCR, and TTR levels in the plasma was measured by western analysis and subsequent densitometry scanning of the protein bands.

As illustrated in Table 36, TTR gene expression in the liver and plasma TTR levels were significantly reduced. This indicates that the antisense oligonucleotides targeting TTR are able to distribute to liver and reduce TTR gene expression, and thereby causing reduction of TTR secretion from liver to circulation.

TABLE 36

Percentage reduction of TTR expression compared to the high-fat saline control

|  | Liver mRNA | Plasma protein |
|---|---|---|
| Saline | 0 | 0 |
| ISIS 401724 | 98 | 100 |
| Lean saline control | n.d. | 39 |

RBP4 levels in the plasma were also measured and were reduced significantly in the ISIS 401724 treated mice (Table 37). This indicates that the inhibition of TTR expression increased renal clearance of RBP4 due to lack of formation of the protein complex. Thus, indicating that TTR-antisense oligonucleotides can also be used to reduce plasma RBP4 levels.

TABLE 37

Percentage reduction of RBP4 levels compared to the control

|  | % inhibition |
|---|---|
| Saline | 0 |
| ISIS 410724 | 95 |

Effect on Insulin Levels

Plasma insulin levels were determined using an ELISA kit from ALPCO Diagnostics. The levels of insulin in treated and control sets are presented in Table 38 and indicate that TTR inhibition via ISIS 401724 may lead to an improvement in insulin sensitivity. This may be the indirect effect of reduction of RBP4 levels due to inhibition of TTR-RBP4 complex formation.

TABLE 38

Effects of TTR antisense oligonucleotides on TTR-RBP4 complex formation and plasma insulin levels (ng/mL)

|  | Insulin level |
|---|---|
| Saline | 9 |
| ISIS 141923 | 6 |
| ISIS 401724 | 4 |

Effect on Peripheral and Hepatic Insulin Sensitivity

After the treatment with antisense oligonucleotides, hepatic and peripheral insulin sensitivity was assessed using hyperinsulinemic-euglycemic clamps. Seven to nine days prior to the clamp, catheters were inserted into the right internal jugular vein extending to the right atrium and the left carotid artery extending into the aortic arch. Subsequently, the mice were fasted for 24 hours, and then infused with 99% [6,6-$^2$H] glucose (1.1 mg/kg prime, 0.1 mg/kg) infusion to assess basal glucose turnover. Ensuing the basal period, the hyperinsulinemic-euglycemic clamp was conducted for 140 minutes with a primed/continuous infusion of insulin (400 mU/kg prime over 5 minutes, 4 mU/kg per minute infusion subsequently) and a variable infusion of 20% dextrose spiked with approximately 2.5% [6,6-$^2$H]glucose to maintain euglycemia. The results are presented in Table 39.

TABLE 39

Effect of TTR antisense oligonucleotides on TTR-RBP4 complex formation and insulin sensitivity

|  | Saline control | Lean control | ISIS 141923 | ISIS 401724 |
|---|---|---|---|---|
| Hepatic glucose production (mg/kg/min) | 22 | 12 | 22 | 17 |
| Glucose infusion rate (mg/kg/min) | 9 | 43 | 11 | 21 |
| Whole body glucose turnover (mg/kg/min) | 32 | 55 | 34 | 38 |
| Whole body glycolysis (mg/kg/min) | 31 | 30 | 32 | 41 |
| Gastrocnemius muscle glucose Uptake (mg/kg/min) | 16 | 45 | 17 | 31 |
| Heart glucose Uptake (mg/kg/min) | 15 | 189 | 18 | 43 |
| WAT glucose Uptake (mg/kg/min) | 0.8 | 2.1 | 0.7 | 0.9 |

ISIS 401724-treated mice, compared to the control, increased the ability of insulin to suppress hepatic glucose production by 23% (treated: 22 vs. saline: 17 mg/kg/min). The rate with which glucose was infused to maintain euglycemia was 57% higher in the ISIS 403527-treated group compared to the control (treated: 21 vs. saline: 9 mg/kg/min), indicating an improvement in whole body insulin sensitivity. Peripheral glycolysis was improved by 24% (treated: 41 vs. saline: 31 mg/kg/min). ISIS 401724 also promoted increased glucose uptake in the gastrocnemius muscle by 48% (treated: 31 vs. saline: 16 mg/kg/min) and in the heart by 65% (treated: 43 vs. saline: 15 mg/kg/min), indicating that ISIS 403527 not only decrease hepatic glucose production but also increase peripheral tissue glucose uptake.

The results shown herein demonstrate that decreasing RBP4 levels by inhibiting TTR expression improves insulin sensitivity and decreases hepatic glucose production. These results indicate that antisense inhibitors of TTR, prevent TTR-RBP4 complex formation, thereby reducing plasma RBP4, and therefore are considered to be RBP4 inhibitors as well. These RBP4 inhibitors are candidate therapeutic agents for the treatment of conditions characterized by elevated hepatic glucose production and decreased peripheral glucose uptake, such as metabolic disorders like Type 2 diabetes, obesity and associated cardiomyopathy.

Example 24

Measuring Antisense Inhibition of RBP4 in the Zucker fa/fa Rat Model

Treatment

The Zucker (fa/fa) rat is the best-known and most widely used rat model of genetic obesity. Animals homozygous for the fa allele became noticeably obese by 3 to 5 weeks of age, and by 14 weeks of age their body composition was over 40 percent fat. The animals have been established to be hyperinsulinaemic but not hyperglycemic.

Zucker rats can be obtained from Charles River Laboratories (Wilmington, Mass.) and given commercial rat (Purina) chow. The rats can be divided into 3 groups. The first can be injected ISIS 403527 at 25 mg/kg twice a week for 5 weeks. The second group can be administered ISIS 141923 control antisense oligonucleotide at 25 mg/kg twice a week for 5 weeks. The third group can be administered saline twice a week for 5 weeks.

Accordingly, the fa/fa rat model can be used to assess the measuring antisense oligonucleotide treatment on glucose tolerance, insulin sensitivity and fatty acid metabolism.
Inhibition of RBP4 Levels At the end of the treatment period, the rats are sacrificed and RBP4 mRNA expression can be measured in liver and white adipose tissue by real-time RT-PCR, and plasma RBP4 levels can be measured with an ELISA kit. These results would determine the potency of the oligonucleotide as well as the ability to distribute the oligonucleotide effectively in different tissues in this model. Further, significant inhibition of RBP4 levels in this model as a result would confirm that ISIS 403527 can be used as a candidate therapeutic agent for the treatment of disorders characterized by RBP4 expression.

Example 25

Measuring Antisense Inhibition of RBP4 in the Zucker fa/fa Rat Model on Plasma Glucose and Insulin Levels Plasma glucose in rats treated, as described in Example 24, can be determined using an automated clinical chemistry analyzer (Hitachi Olympus AU400e, Melville, N.Y.). Plasma insulin levels can be determined using an ELISA kit from ALPCO Diagnostics. The Zucker fa/fa rats treated with ISIS 403527 can be assessed for fed and fasted glucose and insulin levels biweekly and comparisons with control rats can be done.

The results may illustrate changes in fed and fasted plasma glucose and insulin levels before and after treatment with the RBP4 antisense oligonucleotides.

Example 26

Measuring Antisense Inhibition of RBP4 in the Zucker fa/fa Rat Model on Glucose Tolerance An oral glucose tolerance test (OGTT) can be performed. Rats treated, as described in Example 24, can be fasted overnight and then can receive oral administration of glucose of 0.75 mg/kg. Blood glucose levels can be measured before the glucose challenge and at intervals over 2 hours. Plasma levels of insulin can be simultaneously measured. The results will illustrate the control over glucose level exerted before and after treatment with RBP4 antisense oligonucleotides.

Example 27

Measuring Antisense Inhibition of RBP4 in the Zucker fa/fa Rat Model on Insulin Sensitivity For insulin sensitivity tolerance test (ITT), rats treated as described in Example 24 can be fasted for 4 hours, injected with insulin at 1.0 U/kg and tested for glucose levels over a period of 2 hours. The results can illustrate that the changes in insulin sensitivity are due to treatment with the RBP4 antisense oligonucleotides.

Example 28

Measuring Antisense Inhibition of RBP4 in the Zucker fa/fa Rat Model on Fatty Acid Metabolism Measuring the effect of ISIS 403527 on fatty acid metabolism can be measured in rats treated as described in Example 24. Free fatty acid levels in the plasma as well as hepatic rate of beta-oxidation measured by plasma 3-hydroxybutyrate levels can be measured during the treatment.

Example 29

Measuring Antisense Inhibition of RBP4 in the Zucker fa/fa Rat Model on Metabolic Parameters Effect on Body Weight Measuring the effect of the treatment of the rats described in Example 24 with ISIS 403527 on body weight can be monitored over at least 5 weeks.

Effect on Plasma Triglyceride and Cholesterol Levels

ISIS 403527 can be tested for its ability to affect lipid metabolism in the rats, as described in Example 24. Blood can be obtained at different treatment time points and analyzed for plasma cholesterol other lipids. The results may reflect changes observed between the control rats and rats receiving RBP4 antisense oligonucleotides.

Effect on Body Composition

Measuring the effect of the treatment of the rats described in Example 24 with ISIS 403527 on body composition can be monitored over at least 5 weeks. Specifically, the changes in body fat and lean mass composition can be measured.

Examples 24-29 are prophetic examples which describe experiments that could be performed using other relevant preclinical models.

Reduction in cholesterol, triglycerides, and adiposity has therapeutic benefit to subjects having metabolic and cardiovascular disorders like obesity, type 2 diabetes and dyslipidemia. Agents that display such characteristics in addition to glucose lowering and insulin sensitizing properties are candidate therapeutic agent for the treatment of obesity and Type 2 Diabetes, with the added benefit of preventing or reducing associated dyslipidemia that can also lead to the risk of cardiovascular disorders characterized by hypercholesterolemia and hypertriglyceridemia.

Further confirming, as provided herein, RBP4-specific modulators can modulate or inhibit RBP4 expression, activity, or processing. Such agents are candidate therapeutic agents for the treatment of both metabolic and cardiovascular disorders, such as Type 2 diabetes, obesity and dyslipidemia, or any combination thereof.

The in vivo studies provided herein are carried out in well characterized models of disease that are recognized by those of skill in the art as being predictive of therapeutic results in other animals, including humans

Other Embodiments

The detailed description set-forth above is provided to aid those skilled in the art in practicing the present invention. However, the invention described and claimed herein, is not to be limited in scope by the specific embodiments disclosed herein because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which does not depart from the spirit or scope of the present inventive discovery. Such modifications are also intended to fall within the scope of the appended claims.

References Cited

All publications, patents, patent applications and other references cited in this application are incorporated herein, by reference in their entirety for all purposes to the same extent as if each subject publication, patent, patent application or other reference was specifically and subjectively indicated to be incorporated by reference in its entirety for all purposes. Citation of a reference herein, shall not be construed as an admission that such is prior art to the present invention.

---

What is claimed:

1. A method of treating or ameliorating a cardiovascular disease in an animal diagnosed as having cardiovascular disease, comprising administering to the animal a therapeutically effective amount of a Retinol-Binding Protein 4 (RBP4) inhibitor, wherein the RBP4 inhibitor is a nucleic acid capable of inhibiting RBP4 by at least 24%, thereby treating or ameliorating the cardiovascular disease in the animal.

2. The method of claim 1, wherein the cardiovascular disease is obesity, atherosclerosis, dyslipidemia, coronary heart disease, or a combination thereof.

3. The method of claim 2, wherein the dyslipidemia is hyperlipidemia.

4. The method of claim 3, wherein the hyperlipidemia is hypercholesterolemia.

5. The method of claim 1, wherein the administering results in a reduction of cholesterol levels.

6. A method of decreasing cholesterol levels in a human diagnosed as being in need of decreasing cholesterol levels comprising administering a Retinol-Binding Protein 4 (RBP4) inhibitor to the human diagnosed as being in need of decreasing cholesterol levels, wherein the RBP4 inhibitor is a nucleic acid capable of inhibiting RBP4 by at least 24%, thereby decreasing cholesterol levels in the human.

7. The method of claim 6, wherein the nucleic acid is a modified oligonucleotide.

8. The method of claim 7, wherein the modified oligonucleotide consists of 12 to 30 linked nucleosides.

9. The method of claim 8, wherein said modified oligonucleotide is a single-stranded oligonucleotide.

10. The method of claim 9, wherein the nucleobase sequence of the modified oligonucleotide is 100% complementary to human RBP4.

11. The method of claim 9, wherein at least one internucleoside linkage is a modified internucleoside linkage.

12. The method of claim 11, wherein each internucleoside linkage is a phosphorothioate internucleoside linkage.

13. The method of claim 9, wherein at least one nucleoside contains a modified sugar.

14. The method of claim 13, wherein the modified sugar comprises a 2'-O-methoxyethyl sugar moiety.

15. The method of claim 13, wherein the modified sugar is a bicyclic nucleic acid sugar moiety.

16. The method of claim 9, wherein at least one nucleoside comprises a modified nucleobase.

17. The method of claim 15, wherein the bicyclic nucleic acid sugar moiety comprises a 4'-CH(CH3)-O-2' bridge.

18. The method of claim 1, wherein the administering comprises parenteral administration.

19. The method of claim 18, wherein the parenteral administration comprises subcutaneous or intravenous administration.

20. The method of claim 1, comprising co-administering the RBP4 inhibitor and at least one additional therapy.

21. The method of claim 20, wherein the RBP4 inhibitor and the additional therapy are administered concomitantly.

22. The method of claim 20, wherein the RBP4 inhibitor and the additional therapy are administered in the same formulation.

23. A method comprising identifying an animal having a cardiovascular disease and administering to said animal a therapeutically effective amount of a composition comprising a modified oligonucleotide consisting of 12 to 30 linked nucleosides having a nucleobase sequence complementary to SEQ ID NO: 1, 2, 3, 4, 5, 6 or 7 as measured over the entirety of said modified oligonucleotide, wherein the modified oligonucleotide is capable of inhibiting Retinol-Binding Protein 4 (RBP4) by at least 24%, thereby treating the cardiovascular disease.

24. The method of claim 16, wherein the modified nucleobase is a 5-methylcytosine.

25. The method of claim 9, wherein the modified oligonucleotide comprises:
   a gap segment consisting of linked deoxynucleotides;
   a 5' wing segment consisting of linked nucleosides; and
   a 3' wing segment consisting of linked nucleosides;
   wherein the gap segment is positioned between the 5' wing segment and the 3' wing segment, and wherein each nucleoside of each wing segment comprises a modified sugar.

26. The method of claim 25, wherein the oligonucleotide comprises:
   a gap segment consisting of ten linked deoxynucleosides;
   a 5' wing segment consisting of five linked nucleosides; and
   a 3' wing segment consisting of five linked nucleosides;
   wherein the gap segment is positioned between the 5' wing segment and the 3' wing segment, wherein each nucleoside of each wing segment comprises a 2'-O-methoxyethyl sugar, wherein each internucleoside linkage of said modified oligonucleotide is a phosphorothioate linkage, and wherein each cytosine in said modified oligonucleotide is a 5-methylcytosine.

27. The method of claim 1, wherein the animal is a human.

28. The method of claim 23, wherein at least one internucleoside linkage of the modified oligonucleotide is a modified internucleoside linkage.

29. The method of claim 28, wherein each internucleoside linkage is a phosphorothioate internucleoside linkage.

30. The method of claim 23, wherein at least one nucleoside of the modified oligonucleotide contains a modified sugar.

31. The method of claim 30, wherein the modified sugar comprises a 2'-O-methoxyethyl sugar moiety.

32. The method of claim 31, wherein the modified sugar is a bicyclic nucleic acid sugar moiety.

33. The method of claim 32, wherein the bicyclic nucleic acid sugar moiety comprises a 4'-CH(CH3)-O-2' bridge.

34. The method of claim 23, wherein at least one nucleoside of the modified oligonucleotide comprises a modified nucleobase.

35. The method of claim 1, wherein the nucleic acid comprises a modification selected from the group consisting of a modified internucleoside linkage, a modified sugar moiety, and a modified nucleobase.

\* \* \* \* \*